US008454582B2

(12) United States Patent
deJuan et al.

(10) Patent No.: US 8,454,582 B2
(45) Date of Patent: Jun. 4, 2013

(54) METHODS AND DEVICES FOR THE TREATMENT OF OCULAR CONDITIONS

(75) Inventors: Eugene deJuan, LaCanada, CA (US);
Signe E. Varner, Los Angeles, CA (US);
Laurie R. Lawin, New Brighton, MN (US)

(73) Assignee: Surmodics, Inc., Eden Prairie, MN (US)

( * ) Notice: Subject to any disclaimer, the term of this patent is extended or adjusted under 35 U.S.C. 154(b) by 2 days.

(21) Appl. No.: 12/981,038

(22) Filed: Dec. 29, 2010

(65) Prior Publication Data

US 2011/0159073 A1   Jun. 30, 2011

Related U.S. Application Data

(63) Continuation of application No. 11/175,850, filed on Jul. 5, 2005, now abandoned.

(60) Provisional application No. 60/585,236, filed on Jul. 2, 2004, provisional application No. 60/669,701, filed on Apr. 8, 2005.

(51) Int. Cl.
*A61K 9/22* (2006.01)
*A61M 31/00* (2006.01)

(52) U.S. Cl.
USPC ........ 604/891.1; 604/506; 604/206; 604/294; 604/264; 604/270

(58) Field of Classification Search
USPC .................. 424/427, 428, 487; 604/290, 521, 604/890.1, 891.1, 892.1
See application file for complete search history.

(56) References Cited

U.S. PATENT DOCUMENTS

| 3,598,119 | A | 8/1971 | White |
|---|---|---|---|
| 3,659,610 | A | 5/1972 | Cimber |
| 4,300,557 | A | 11/1981 | Refojo et al. |
| 4,645,491 | A | 2/1987 | Evans |
| 4,710,171 | A | 12/1987 | Rosenberg |
| 4,781,691 | A | 11/1988 | Gross |
| 4,869,717 | A | 9/1989 | Adair |
| 4,909,784 | A | 3/1990 | Dubroff |
| 4,978,334 | A | 12/1990 | Toye et al. |
| 5,098,443 | A | 3/1992 | Parel et al. |
| 5,207,660 | A | 5/1993 | Lincoff |
| 5,238,481 | A | 8/1993 | Takagi et al. |
| 5,266,562 | A | 11/1993 | Mukherjee et al. |
| 5,273,530 | A | 12/1993 | del Cerro et al. |
| 5,326,345 | A | 7/1994 | Price, Jr. |
| 5,328,481 | A | 7/1994 | Wang |
| 5,378,475 | A | 1/1995 | Smith et al. |
| 5,395,618 | A | 3/1995 | Darougar et al. |
| 5,409,457 | A | 4/1995 | del Cerro et al. |
| 5,443,505 | A * | 8/1995 | Wong et al. ............. 623/4.1 |
| 5,466,233 | A | 11/1995 | Weiner et al. |
| 5,476,511 | A | 12/1995 | Gwon et al. |
| 5,487,725 | A | 1/1996 | Peyman |
| 5,665,769 | A | 9/1997 | Kato et al. |
| 5,723,530 | A | 3/1998 | Zanzig et al. |
| 5,725,514 | A | 3/1998 | Grinblat et al. |
| 5,770,589 | A | 6/1998 | Billson et al. |
| 5,773,019 | A | 6/1998 | Ashton et al. |
| 5,792,099 | A | 8/1998 | DeCamp et al. |
| 5,824,685 | A | 10/1998 | Campochiaro et al. |
| 5,827,236 | A | 10/1998 | Takahashi |
| 5,869,079 | A | 2/1999 | Wong et al. |
| 5,871,470 | A | 2/1999 | McWha |
| 5,902,598 | A | 5/1999 | Chen et al. |
| 5,904,144 | A | 5/1999 | Hammang et al. |
| 5,941,250 | A | 8/1999 | Aramant et al. |
| 5,972,027 | A | 10/1999 | Johnson |
| 6,001,386 | A | 12/1999 | Ashton et al. |
| 6,025,329 | A | 2/2000 | Utsumi et al. |
| 6,036,678 | A | 3/2000 | Giungo |
| 6,075,032 | A | 6/2000 | Campochiaro et al. |
| 6,159,218 | A | 12/2000 | Aramant et al. |
| 6,214,901 | B1 | 4/2001 | Chudzik et al. |
| 6,217,895 | B1 | 4/2001 | Guo et al. |
| 6,251,090 | B1 | 6/2001 | Avery et al. |
| 6,254,587 | B1 | 7/2001 | Christ et al. |

(Continued)

FOREIGN PATENT DOCUMENTS

| EP | 0 322 319 | 6/1989 |
|---|---|---|
| EP | 0 417 764 | 3/1991 |

(Continued)

OTHER PUBLICATIONS

PCT Search Report for International Application No. PCT/US2005/023972; mailed on Apr. 27, 2006.
Myles M.E., et al., (2003) *Ocular Iontophoresis*, Ophthalmic Drug Delivery Systems, 2nd, Ed.: 365-400.
Slakter J.S., (2004) *Drug delivery to back of eye challenging for retinal diseases*, Ophthalmology Times/Special Report.
Gragoudas E.S., et al., (2004) *Pegaptanib for Neovascular Age-Related Macular Degeneration*, New England Journal of Medicine 351: 2805-2816.
Gragoudas E.S., et al., (2004) *Pegaptanib for Neovascular Age-Related Macular Degeneration*, Supplementary Appendix: 1-9.
Aiello L.P, et al., (2004) *Evolving Guidelines for Intravitreous Injections*, Retina, The Journal of Retinal and Vitreous Diseases, 24: S3-S19.

(Continued)

*Primary Examiner* — Michael G Hartley
*Assistant Examiner* — Jagadishwar Samala
(74) *Attorney, Agent, or Firm* — Kagan Binder, PLLC

(57) ABSTRACT

Featured is a method for instilling one or more bioactive agents into ocular tissue within an eye of a patient for the treatment of an ocular condition, the method comprising concurrently using at least two of the following bioactive agent delivery methods (A)-(C): (A) implanting a sustained release delivery device comprising one or more bioactive agents in a posterior region of the eye so that it delivers the one or more bioactive agents into the vitreous humor of the eye; (B) instilling (e.g., injecting or implanting) one or more bioactive agents subretinally; and (C) instilling (e.g., injecting or delivering by ocular iontophoresis) one or more bioactive agents into the vitreous humor of the eye.

20 Claims, 22 Drawing Sheets

U.S. PATENT DOCUMENTS

| | | | |
|---|---|---|---|
| 6,299,603 | B1 | 10/2001 | Hecker et al. |
| 6,309,374 | B1 | 10/2001 | Hecker et al. |
| 6,331,313 | B1 | 12/2001 | Wong et al. |
| 6,358,935 | B1 | 3/2002 | Beck et al. |
| 6,375,972 | B1 | 4/2002 | Guo et al. |
| 6,378,526 | B1 | 4/2002 | Bowman et al. |
| 6,397,849 | B1 | 6/2002 | Bowman et al. |
| 6,402,734 | B1 | 6/2002 | Weiss |
| 6,413,245 | B1 | 7/2002 | Yaacobi et al. |
| 6,413,540 | B1 | 7/2002 | Yaacobi |
| 6,436,427 | B1 | 8/2002 | Hammang et al. |
| 6,462,071 | B1 | 10/2002 | Castillejos |
| 6,537,253 | B1 | 3/2003 | Haindl |
| 6,544,249 | B1 | 4/2003 | Yu et al. |
| 6,548,078 | B2 | 4/2003 | Guo et al. |
| 6,579,256 | B2 | 6/2003 | Hughes |
| 6,669,950 | B2 | 12/2003 | Yaacobi |
| 6,669,980 | B2 | 12/2003 | Hansen |
| 6,699,493 | B2 | 3/2004 | Wong |
| 6,713,081 | B2 | 3/2004 | Robinson et al. |
| 6,719,750 | B2 | 4/2004 | Varner et al. |
| 6,750,196 | B1 | 6/2004 | Reh et al. |
| 7,077,848 | B1 | 7/2006 | de Juan, Jr. et al. |
| 2001/0008961 | A1 | 7/2001 | Hecker et al. |
| 2002/0026176 | A1* | 2/2002 | Varner et al. ............... 604/891.1 |
| 2002/0042652 | A1 | 4/2002 | Peyman |
| 2002/0055724 | A1 | 5/2002 | Hughes |
| 2002/0061327 | A1 | 5/2002 | Hammang et al. |
| 2002/0115959 | A1 | 8/2002 | Lloyd et al. |
| 2002/0127250 | A1 | 9/2002 | Guo et al. |
| 2002/0139378 | A1 | 10/2002 | Trese et al. |
| 2002/0188037 | A1 | 12/2002 | Chudzik et al. |
| 2002/0198511 | A1* | 12/2002 | Varner et al. ............... 604/521 |
| 2003/0014036 | A1 | 1/2003 | Varner et al. |
| 2003/0021828 | A1 | 1/2003 | Guo et al. |
| 2003/0064088 | A1 | 4/2003 | Carvalho et al. |
| 2003/0069560 | A1 | 4/2003 | Adamis et al. |
| 2003/0073597 | A1 | 4/2003 | Gallotti et al. |
| 2003/0158521 | A1 | 8/2003 | Ameri |
| 2003/0232087 | A1* | 12/2003 | Lawin et al. ............... 424/487 |
| 2004/0009222 | A1 | 1/2004 | Chou et al. |
| 2004/0022853 | A1 | 2/2004 | Ashton et al. |
| 2004/0047911 | A1 | 3/2004 | Lyu et al. |
| 2004/0062875 | A1 | 4/2004 | Chappa et al. |
| 2004/0121014 | A1 | 6/2004 | Guo et al. |
| 2004/0133155 | A1 | 7/2004 | Varner et al. |
| 2004/0175410 | A1 | 9/2004 | Ashton et al. |
| 2004/0208910 | A1 | 10/2004 | Ashton et al. |
| 2004/0215133 | A1 | 10/2004 | Weber et al. |
| 2005/0008695 | A1 | 1/2005 | Ashton et al. |
| 2005/0019371 | A1 | 1/2005 | Anderson et al. |
| 2005/0025834 | A1 | 2/2005 | Guo et al. |
| 2005/0059956 | A1 | 3/2005 | Varner et al. |
| 2005/0186279 | A1 | 8/2005 | Guo et al. |
| 2005/0196424 | A1 | 9/2005 | Chappa |
| 2005/0220839 | A1 | 10/2005 | DeWitt et al. |
| 2005/0220840 | A1 | 10/2005 | DeWitt et al. |
| 2005/0220841 | A1 | 10/2005 | DeWitt et al. |
| 2005/0220842 | A1 | 10/2005 | DeWitt et al. |
| 2005/0220843 | A1 | 10/2005 | DeWitt et al. |
| 2005/0244459 | A1 | 11/2005 | DeWitt et al. |
| 2006/0182783 | A1* | 8/2006 | Hughes et al. ............... 424/427 |

FOREIGN PATENT DOCUMENTS

| | | |
|---|---|---|
| EP | 1 484 054 | 12/2004 |
| JP | 9-136830 | 5/1997 |
| JP | 2003-171315 | 6/2003 |
| JP | 2003-313119 | 11/2003 |
| WO | 95/28984 | 11/1995 |
| WO | 00/40089 | 7/2000 |
| WO | 02/17884 | 3/2002 |
| WO | 03/105918 | 12/2003 |
| WO | 2004/028477 | 4/2004 |
| WO | 2005/097228 | 10/2005 |
| WO | 2005/099786 | 10/2005 |
| WO | 2005/099787 | 10/2005 |

OTHER PUBLICATIONS

Smith T.J., et al., (1992) *Intravitreal Sustained-Release Ganciclovir*, Arch Ophthalmol. 110: 255-258.

Sanborn G.E., et al., (1992) *Sustained-Release Ganciclovir Therapy for Treatment of Cytomegalovirus Retinitis; Use of an Intravitreal Device*, Arch Ophthalmol. 110: 188-195.

Pitt C.G., (1990) *Poly-ϵ-Caprolactone and Its Copolymers*, Biodegradable Polymers as Drug Delivery Systems, New York: Preface & 71-120.

* cited by examiner

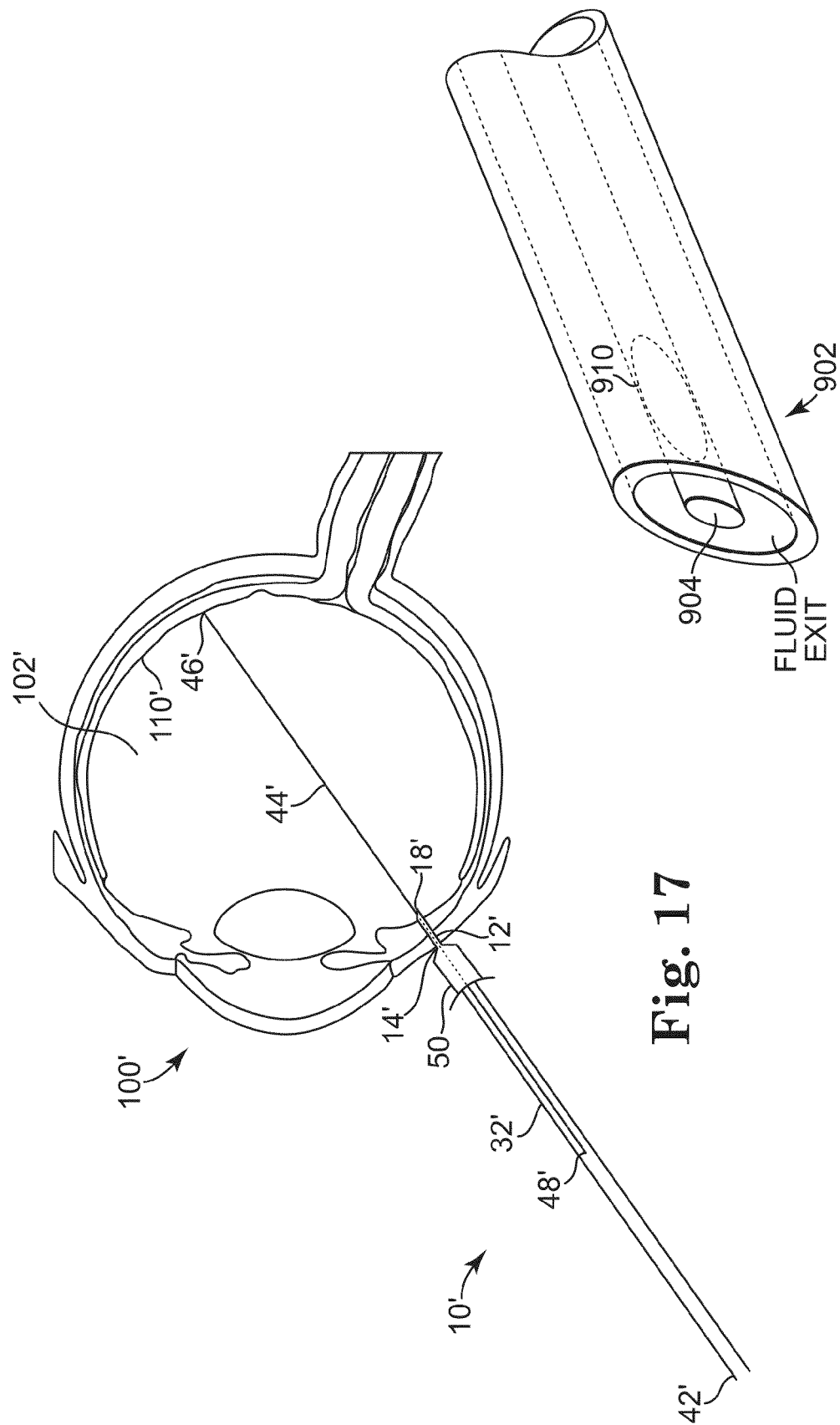

50mm

METHODS AND DEVICES FOR THE TREATMENT OF OCULAR CONDITIONS

CROSS-REFERENCE TO RELATED APPLICATIONS

This application is a continuation of U.S. application Ser. No. 11/175,850, filed Jul. 5, 2005 now abandoned, entitled "METHODS AND DEVICES FOR THE TREATMENT OF OCULAR CONDITIONS," which claims the benefit of U.S. Provisional Application Ser. No. 60/585,236, filed Jul. 2, 2004, entitled "METHODS, DEVICES AND SYSTEMS FOR TREATMENT OF OCULAR DISEASES AND CONDITIONS," and U.S. Provisional Application Ser. No. 60/669,701, filed Apr. 8, 2005, entitled "SUSTAINED DELIVERY DEVICES FOR THE CHOROID AND RETINA AND METHODS FOR SUBRETINAL ADMINISTRATION OF BIOACTIVE AGENTS TO TREAT AND/OR PREVENT RETINAL DISEASES," which applications are incorporated herein by reference in their entirety.

FIELD

The invention relates to methods and devices for the treatment of ocular conditions.

BACKGROUND

There are a number of vision-threatening disorders or diseases of the eye of a mammal including, but not limited to diseases of the retina, retinal pigment epithelium (RPE) and choroid. Such vision threatening diseases include ocular neovascularization, ocular inflammation and retinal degenerations. Examples of these disease states include diabetic retinopathy, chronic glaucoma, retinal detachment, sickle cell retinopathy, age-related macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy-2 and lensectomy, vascular diseases, retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, and retinal artery occlusion, and neovascularization due to penetration of the eye or ocular injury.

Age-related macular degeneration (AMD) is the leading cause of irreversible severe central vision loss in Caucasians fifty years old and older in the United States. According to the 1990 U.S. census, approximately 750,000 people over 65 years of age were estimated as severe visual impairment in one or both eyes from AMD. Also, the number of cases of AMD has been predicted to increase from 2.7 million in 1970 to 7.5 million by the year 2030.

Roughly 80 percent of the AMD cases involve non-neovascular conditions, for which there are no effective treatments. For the remaining cases involving neovascularization, currently available treatments are sub-optimal. Perhaps the best known therapy is photodynamic therapy (PDT), however, while this therapy has received significant attention in both the ophthalmic and financial investment communities, it is useful in only about 20 percent of neovascular AMD cases. In addition, this particular therapy is not a simple or inexpensive treatment. The procedure generally needs to be repeated every three months for at least two years, with approximate total cost of $12,250.

A number of angiostatic agents are currently under investigation for the treatment of AMD. Thalidomide, for example, is known to be a powerful angiostatic agent. Its systemic side effects, however, include peripheral neuropathy, central nervous system depression, and embryotoxicity. In addition, these systemic side effects have limited the dosage administered to patients for the treatment of subretinal neovascularization. Systemic inhibition of angiogenesis in older patients can also interfere with the development of collateral circulation, which has a role in the prevention of central nervous system as well as cardiac ischemic events.

A number of techniques or methodologies have been developed to deliver drugs to the various tissues or structure that make up the mammalian eye, as described hereinafter, to treat a wide range of disorders or diseases of the eye. However, delivery of drugs, proteins and the like to the eye(s) of mammals in order to achieve the desired therapeutic or medical effect, especially to the retina and/or the choroid, has proved to be challenging, owing in large part to the geometry, delicacy and/or behavior of the eye and its components. A brief description of various conventional methods or techniques for delivering drugs to the tissues of the eye and the shortcomings thereof is summarized.

Oral ingestion of a drug or injection of a drug at a site other than the eye can provide a drug systemically, however such a systemic administration does not provide effective levels of the drug specifically to the eye. In many ophthalmic disorders involving the retina, posterior tract, and optic nerve, adequate levels of the drug cannot be achieved or maintained by oral or parenteral routes of administration. Thus, further and repeated administration of the drug would be necessary to achieve the desired or adequate levels of concentration of the drug. Such further and repeated administrations of such drugs may produce undesired systemic toxicity.

Ophthalmic conditions have also been treated using drugs applied directly to the eye in either liquid or ointment form. This route of administration (i.e., topical administration) is only effective in treating problems involving the superficial surface of the eye and diseases that involve the cornea and anterior segment of the eye, such as conjunctivitis. Topical administration of drugs is not effective in achieving adequate concentrations of a drug(s) in the sclera, vitreous, or posterior segment of the eye. In addition, topical eye drops may drain from the eye through the nasolacrimal duct and into the systemic circulation, further diluting the medication and risking unwanted systemic side effects. Furthermore, delivery of drugs in the form of topical eye drops is also of little utility because the drug cannot cross the cornea and be made available to the vitreous, retina, or other subretinal structures such as the retinal pigment epithelium ("RPE") or choroidal vasculature. Some drugs are highly unstable and therefore not easily formulated for topical delivery. Moreover, data also indicate that it is not unusual for up to 85% of topically applied agents to he removed by the eye's blink mechanism/reflex.

Direct delivery of drugs to the eye by a topical insert has also been attempted, however, this method is not desirable. Such topical inserts require patient self-administration and thus education on their insertion into and removal from the eye. Consequently, this technique demands a certain degree of manual dexterity that can be problematic for geriatric patients who are particularly susceptible to certain eye disorders that appear age related (e.g., age related macular degeneration). In many instances such topical inserts may cause eye irritation and such inserts are prone to inadvertent loss due to eyelid laxity. In addition, these devices provide a source of drug only to the cornea and anterior chamber, and thus do not provide any pharmacologic advantage over topical eye drops or ointments. Such devices therefore have limited, if any at all, utility for providing an effective source of drugs to the vitreous or tissues located in the posterior segment of the eye.

Consequently, most methods for treating eye disorders or diseases in the posterior segment, or the back-of-the-eye, involve intravitreal delivery of the drug. One such technique for intravitreal delivery is accomplished by intraocular injection of the drug or microspheres containing the drug directly into the vitreous or by locating a device or capsule containing the drug in the vitreous, such as that described in U.S. Pat. No. 5,770,589. Intravitreal injection of a drug is an effective means of delivering the drug to the posterior segment of the eye in high concentrations, but it is not without its shortcomings. It is well known that drugs that are initially located within the vitreous are removed from the vitreous over time via the anterior segment of the eye. If the ocular condition is anything other than acute, this technique necessarily requires follow-up injections in order to maintain an adequate therapeutic concentration within the vitreous. This, in turn, presents problems because each additional intraocular injection carries with it a realistic risk of infection, hemorrhage and/or retinal detachment.

It also is well known that many therapeutic drugs cannot easily diffuse across the retina. The dose being administered and maintained in the vitreous has to take into account the amount that can diffuse across the retinal boundary as well as how long the drug is retained in effective amounts within the vitreous. It has been observed from animal studies that 72 hours after injection of triamcinolone, less than 1% of the triamcinolone present in the vitreous is associated with other tissues including the retina, pigment epithelium, and sclera.

In addition to concerns relating to the relative effectiveness of drug delivery across the barrier, complications or side effects have been observed when using a direct injection into vitreous technique with some therapeutics. For example, corticosteroid compounds, such as triamcinolone, can effectively treat some forms of neovascularization such as corneal neovasularization. When these compounds are used to treat neovascularization of the posterior segment by direct injection, undesirable side effects can be caused in many patients. The adverse affects or undesirable side effects included elevations in intraocular pressure and the formation of, or acceleration of, the development of cataracts. Elevations in intraocular pressure are of particular concern in patients who are already suffering from elevated intraocular pressure, such as glaucoma patients. Moreover, there is a risk in using corticosteroids in patients with normal intraocular pressure because of elevations in pressure that can result in damage to ocular tissue. Since therapy with corticosteroids is frequently long term, i.e., several days or more, a potential exists for significant damage to ocular tissue as a result of prolonged elevations in intraocular pressure attributable to that therapy.

Consequently, investigations in the area of intravitreal delivery also have focused on developing a sustained release implant, capsule or other such device or mechanism that is in communication with the vitreous and which is configured so as to provide a release over time into the vitreous of the contained drug. Examples of such controlled release devices are described in U.S. Pat. Nos. 6,217,895; 5,773,019; 5,378,475; and U.S. Patent Application Publication No. 2002/0061327.

A common feature of the techniques/instruments described in these references, is that a surgical incision is required at the outset of a procedure so that the implant, capsule or other such device can be inserted through the eye and located in the vitreous. These methods and techniques also necessarily involve the use of sutures following completion of the procedure to seal or close the incision in order to prevent loss of vitreous material. As is known to those skilled in the art, maintaining the volume of the posterior segment or vitreous is necessary to maintaining the shape and optical arrangement of the eye. Such a course of treatment also increases the duration and cost as well as the realistic risks of corneal ulceration, cataract formation, intraocular infection, and/or vitreous loss that accompany these procedures.

U.S. Pat. Nos. 5,273,530 and 5,409,457 describe an instrument and methodology to transplant donor cells, more specifically donor retina cells, in the subretinal space. The instrument is also described as useful for injecting or removing material from the vitreous. According to the described methodology, the instrument is shaped and dimensioned so it can be inserted into an eye orbit along an insertion path that extends along the periphery of the eye in order to place the tip adjacent to the retina or sub-retinal region. The tip is then moved generally in the medial direction so that the tip pierces the exterior of the eye and resides in the sub-retinal region or in the vitreous, depending upon how much the tip is moved. In order to prevent over-insertion of the tip, a collar is provided about the tip in order to limit the distance the tip can be inserted into the eye.

U.S. Patent Application Publication 2002/0055724 describes an instrument for sub-retinal transplantation of retinal cells, epithelium and choroid within their normal planar configuration as a graft into the sub-retinal region of an eye. The described instrument is inserted into an opening in the eye using either a transcorneal surgical approach or a transchoroidal and scleral surgical approach. According to this technique, the instrument is advanced under the retina to detach the retina so that the graft can be inserted. As noted in U.S. Pat. No. 5,273,530, the penetration of the anterior part or segment of the eye, using the transcorneal or the transscleral route creates the risk of corneal ulceration, cataract formation and other anterior penetration problems. Also using either approach, a surgical incision is created at the outset of a procedure so that the instrument can be inserted and sutures are used following completion of the procedure to seal or close the incision inn order to prevent loss of vitreous material (i.e., aqueous humor).

The delivery of drugs to the eye presents significant challenges. The ocular absorption of systemically administered pharmacologic agents is limited by the blood ocular barrier, namely the tight junctions of the retinal pigment epithelium and vascular endothelial cells. High systemic doses of therapeutic drugs can penetrate this blood ocular barrier in relatively small amounts, but may expose the patient to the risk of systemic toxicity. Topical delivery of drugs often results in limited ocular absorption due to the complex hydrophobic/hydrophilic properties of the cornea and sclera. Additionally, topical agents are mechanically removed by the blink mechanism such that only approximately 15% of a single drop is absorbed. Diffusion of topically administered drugs to the posterior chamber occurs, but often at sub-therapeutic levels. Intravitreal injection of drugs is an effective means of delivering a drug to the posterior segment in high concentrations. However, repeated intraocular injections carry the risk of infection, hemorrhage and retinal detachment. Patients also find this procedure somewhat difficult to endure, resulting in high rates of noncompliance.

Local sustained delivery of therapeutics to the posterior chamber is particularly critical in managing several chronic diseases of the eye. In attempts to address this need, several drug delivery devices have been developed for intraocular insertion into the vitreous region of the eye.

U.S. Pat. No. 4,300,557, for example, describes an intraocular implant in the form of a silicone capsule, which can be filled with a drug to be delivered. The implant is inserted through an incision into the vitreous region of the eye. After insertion of the implant, the incision is closed and the capsule remains in place for a period of time. Attached to the implant is a tube that passes through the surface of the eye. The tube may be used for subsequent injection of a drug while the implant is in the eye. The implant may be removed by making a second surgical incision into the eye and retrieving the implant. While in the vitreous, the device is not anchored and may move about freely. Because the overall shape of the capsule is linear, the amount of drug held by the device and delivered over the surface area of the device is limited. If the width of the capsule is increased, excessive sized incisions will be required for insertion of the device. If the length of the capsule is increased to greater than 1 cm, the implant will pass into the central visual field of the eye, causing blind spots in the patient's eye as well as increased risk of damage to the retinal tissue and lens capsule.

U.S. Pat. No. 5,378,475 describes a device which has been developed for insertion in the vitreous region of the eye, and is described in T. J. Smith et al., Sustained Release Ganciclovir, *Arch. Ophthalmol,* 110, 255-258 (1992) and G. E. Sanborn, et al., Sustained-Release Ganciclovir Therapy for Treatment of Cytomegalovirus Retinitis; Use of an Intravitreal Device, *Arch. Ophthalmol,* 110, 188-195 (1992). This device consists of an inner core of pharmacologic agent surrounded by two coatings with different permeabilities. Drug diffuses through a small opening in one of these coatings achieving near zero-order release kinetics. It is implanted in the region of the pars plana through a 3.55.0 mm scleral incision. The implant must be removed and replaced every 6 months in the operating room as the drug becomes depleted. There is an approximately 25% complication rate from these procedures. The device is a membrane diffusion drug delivery system that relies on EVA/PVA polymers to mediate release rate. However, many agents cannot be effectively delivered from such a system because their permeation rate through the rate controlling material of the system is too small to produce a useful effect. Other agents cannot be satisfactorily delivered by diffusional devices because of a particular chemical characteristic of the agent. This includes salts, because of their ionic character, and unstable polar compounds that cannot be formulated into a composition suitable for storage and delivery from such systems.

U.S. Pat. No. 5,098,443 describes certain specific implants that are inserted through incisions made in the eye wall or sutured around the globe of the eye. These rings may be formed from biodegradable polymers containing microparticles of drug. Alternatively, the implant may be in the form of a hollow flexible polymeric cocoon with the drug disposed therewithin for slow release by osmosis. No anchoring device is described.

U.S. Pat. No. 5,466,233 describes a certain tack for intraocular drug delivery. This device has an end that is positioned in the vitreous cavity while the head remains external to the eye and abuts the scleral surface. The tack contains a fixation portion to attempt to retain attachment within the eye. Because the overall shape of the capsule is linear, the amount of drug that may be held by the device and the surface area through which the drug may be delivered is limited. If the width of the capsule is increased, excessive sized incisions will be required for insertion of the device. If the length of the capsule is increased to greater than 1 cm, the implant will pass into the central visual field of the eye, thereby causing blind spots in the patient's eyes well as increase risk of damage to the retinal tissue and lens capsule.

In view of the above, it would be desirable to provide additional methods and devices for treating the eye, particularly treating retinal and/or choroidal conditions.

SUMMARY

In one aspect, the invention provides a method for instilling one or more bioactive agents into ocular tissue within an eye of a patient for the treatment of an ocular condition, the method comprising concurrently using at least two of the following bioactive agent delivery methods (A)-(C):

(A) implanting a sustained release delivery device comprising one or more bioactive agents in a posterior region of the eye so that it delivers the one or more bioactive agents into the vitreous humor of the eye;

(B) instilling (e.g., injecting or implanting) one or more bioactive agents subretinally; and (C) instilling (e.g., injecting or delivering by ocular iontophoresis) one or more bioactive agents into the vitreous humor of the eye.

In one embodiment of the method, method (A) is used concurrently with method (B). In this embodiment, one or more bioactive agents are released to the vitreous humor of the eye from a sustained release delivery device implanted in the posterior region of the eye; and one or more bioactive agents are instilled (e.g., injected or implanted) subretinally. The one or more bioactive agents delivered by the sustained release delivery device may be the same as or may be different than the one or more bioactive agents delivered subretinally. In another embodiment of the method, method (A) is used concurrently with method (C). In this embodiment, one or more bioactive agents are released to the vitreous humor of the eye from a sustained release delivery device implanted in the posterior region of the eye; and one or more bioactive agents are instilled (e.g., injected or delivered by ocular iontophoresis) into the vitreous humor of the eye. In this embodiment, the one or more bioactive agents released by the sustained release delivery device of method (A) may be the same as or different than the one or more bioactive agents instilled (e.g., injected or delivered by ocular iontophoresis) by method (C). In yet another embodiment, method (B) is used concurrently with method (C). In this embodiment, one or more bioactive agents are instilled (e.g., injected or implanted) subretinally and one or more bioactive agents are instilled (e.g., injected or delivered by ocular iontophoresis) into the vitreous humor of the eye. In this embodiment, the one or more bioactive agents delivered by method (B) may be the same as or different than the one or more bioactive agents delivered by method (C). In yet another embodiment, method (A) is used concurrently with both method (B) and method (C) to instill one or more bioactive agents into ocular tissue in the eye. In this embodiment, the one or more bioactive agents delivered by one method may be the same as or different than the one or more bioactive agents delivered by the other methods.

In some embodiments, method (B) comprises instilling (e.g., injecting or implanting) one or more bioactive agents subretinally. The bioactive agent(s) may be injected subretinally when provided, for example, in the form of a liquid or it may be implanted subretinally when provided in the form of a solid (e.g., a sustained release delivery device). In some embodiments, method (B) comprises (a) forming a localized retinal detachment to define a subretinal space; and instilling one or more bioactive agents in the subretinal space formed by localized retinal detachment.

In some embodiments, method (C) comprises injecting one or more bioactive agents into the vitreous humor of the eye using a needle. In another embodiment, the one or more bioactive agents are instilled by ocular iontophoresis, for example, transscleral iontophoresis.

In some embodiments, the one or more bioactive agents are provided in a sustained release delivery device that is configured for implantation in the subretinal space. The sustained release delivery device may be a solid in the form of a capsule, pellet, rod, sheet, or film. In some embodiments, the sustained release delivery device may be in the form of a flexible rod, thin film, foldable disc, biodegradable polymer with the bioactive agent embedded within, bioactive agent-eluting polymer coating over a rigid scaffold, compressed pellet of one or more bioactive agents, or one or more bioactive agents encapsulated in a semi-permeable membrane. The sustained release delivery device may be tapered at a proximal end, a distal end, or both the proximal and distal ends.

In another embodiment, the sustained release delivery device is in the form of a biocompatible polymer capsule comprising (a) a core comprising one or more bioactive agents; and (b) a jacket surrounding the core comprising a membrane that is biocompatible and that permits diffusion of the one or more bioactive agents.

In another embodiment, the sustained release delivery device comprises a core having an outer surface; and a coating layer of a polymer matrix and at least one bioactive agent applied over at least a portion of the outer surface of the core. The coating layer may be provided on a portion of the outer surface of the core (e.g., an intermediate portion) or it may cover the entire outer surface of the core. The coating layer may include a proximal transition segment, a distal transition segment, or both a proximal and a distal transition segment. Representative examples of core materials include titanium alloys, nickel-cobalt base alloys, stainless steel, cobalt-chromium alloys, and biodegradable magnesium alloys.

In some embodiments, the polymer matrix comprises a first polymer and a second polymer wherein the first polymer is a poly(alkyl(meth)acrylate) or a poly(aromatic (meth)acrylate) and wherein the second polymer is poly(ethylene-co-vinyl acetate). Poly(aromatic(meth)acrylates) include poly(aryl (meth)acrylates), poly(aralkyl(meth)acrylates), poly(alkaryl (meth)acrylates), poly(aryloxyalkyl(meth)acrylates), and poly(alkoxyaryl (meth)acrylates). Poly(alkyl(meth)acrylates) include poly(n-butyl methacrylate), poly(n-butyl methacrylate-co-methyl methacrylate), poly(n-butyl methacrylate-co-isobutyl methacrylate), and poly(t-butyl methacrylate). In one embodiment, the first polymer is poly (butylmethacrylate) and the second polymer is poly(ethylene-co-vinyl acetate).

In some embodiments, the intraocular sustained release delivery device of method (A) comprises a nonlinear body member having a direction of extension, a longitudinal axis along the direction of extension, and a proximal end and a distal end, wherein at least a portion of the body member deviates from the direction of extension, and wherein the body member includes the one or more bioactive agents, and a polymer matrix. The body member may be coil-shaped. In some embodiments, the sustained delivery device includes a cap positioned at the proximal end of the body member. In some embodiments the body member includes a lumen.

In some embodiments, the sustained release delivery device has a total diameter of no greater than about 1000 μm and a length of no greater than about 6 mm.

In some embodiments, the sustained release delivery devices have a bioactive agent elution rate of at least 0.0001 μg per day or greater.

Methods of the invention may deliver one or more bioactive agents, for example, antiproliferative agents, anti-inflammatory agents, anti-angiogenic agents, antibiotics, neurotrophic factors, or combinations thereof.

As used herein, a "coating composition" refers to one or more vehicles (for example, solutions, mixtures, emulsions, dispersions, blends, and the like) used to effectively coat a surface. A "coated composition" refers to the combination of one or more bioactive agent and a polymer on a surface of the device. The coated composition can be formed from one or more coating compositions, or in one or more layers, as will be apparent from the teaching herein.

As used herein, "biocompatible" means the ability of an object to be accepted by and to function in a recipient without eliciting a significant foreign body response (such as, for example, an immune, inflammatory, thrombogenic, or the like response). For example, when used with reference to one or more of the polymers of the invention, biocompatible refers to the ability of the polymer (or polymers) to be accepted by and to function in its intended manner in a recipient.

As used herein, "therapeutically effective amount" refers to that amount of a bioactive agent alone, or together with other substances (as described herein), that produces the desired effect (such as treatment of a medical condition such as a disease or the like, or alleviation of pain) in a patient. During treatment, such amounts will depend upon such factors as the particular condition being treated, the severity of the condition, the individual patient parameters including age, physical condition, size and weight, the duration of the treatment, the nature of the particular bioactive agent thereof employed and the concurrent therapy (if any), and like factors within the knowledge and expertise of the health practitioner. A physician or veterinarian of ordinary skill can readily determine and prescribe the effective amount of the bioactive agent required to treat and/or prevent the progress of the condition.

The term "implantation site" refers to the site within a patient's body at which the implantable device is placed according to the invention. In turn, a "treatment site" includes the implantation site as well as the area of the body that is to receive treatment directly or indirectly from a device component. For example, bioactive agent can migrate from the implantation site to areas surrounding the device itself, thereby treating a larger area than simply the implantation site. The term "incision site" refers to the area of the patient's body (the skin and transdermal area) at which an incision or surgical cut is made to implant the device according to the invention. The incision site includes the surgical cut, as well as the area in the vicinity of the surgical cut, of the patient.

The term "instill" means to deliver one or more bioactive agents using various delivery means and/or mechanisms.

The term "treatment course" refers to the dosage rate over time of one or more bioactive agents, to provide a therapeutically effective amount to a patient. Thus, factors of a treatment course include dosage rate and time course of treatment (total time during which the bioactive agent(s) is administered).

BRIEF DESCRIPION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 17 is a schematic view illustrating the subretinal instillation of a bioactive agent using a subretinal bioactive agent delivery device.

FIG. 18 is a detail view of an embodiment of an operable end of the subretinal bioactive agent delivery device of FIG. 16.

DETAILED DESCRIPTION

Figure 1:
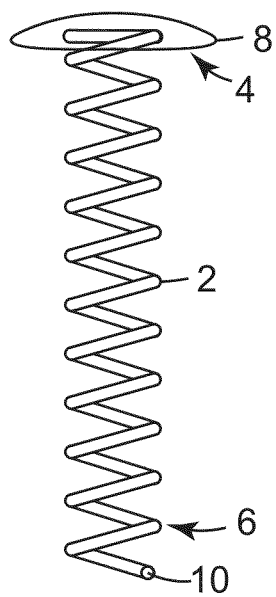
FIG. 1 shows a perspective view of an implantable device configured for intraocular placement according to one embodiment of the invention.

The present invention is directed to methods and devices for treating ocular conditions (e.g., ocular diseases and disorders). The methods and devices provide flexibility in treatment of ocular conditions, including flexibility in the combination of bioactive agent(s) and delivery methods employed.

In one aspect, the invention provides a method for instilling one or more bioactive agents to ocular tissue within an eye of a patient for the treatment of an ocular condition, the method comprising concurrently using at least two of the following bioactive agent delivery methods (A)-(C):

(A) implanting a sustained release delivery device comprising one or more bioactive agents in a posterior region of the eye so that it delivers the one or more bioactive agents into the vitreous humor of the eye;

(B) instilling (e.g., injecting or implanting) one or more bioactive agents subretinally; and (C) instilling one or more bioactive agents into the vitreous humor.

In one embodiment of the invention, the method comprises using method A concurrently with method B. In another embodiment, the method of the invention comprises using method A concurrently with method C. In another embodiment, the method comprises using method B concurrently with method C. In yet another embodiment, the method of the invention comprises using method A concurrently with both method B and method C.

In each of the above-described embodiments, the individual methods may be used to deliver the same bioactive agent(s) or to deliver different bioactive agent(s) to the eye. For example, if method A is used in conjunction with method C, the bioactive agent(s) delivered by method A may be the same or different than the bioactive agent(s) delivered by method C.

Advantageously, the method of the invention may be used to simultaneously instill bioactive agents that may not be readily delivered by one method and/or by one device. For example, bioactive agents that are different in molecular weight, hydrophobicity, polarity, physical state (e.g., solid or liquid) and/or stability may be simultaneously instilled using the method of the present invention. In one embodiment, a first bioactive agent is delivered subretinally from a sustained release delivery device and a second bioactive agent that is different from the first bioactive agent in molecular weight, hydrophobicity, polarity, and/or stability is delivered to the vitreous humor. In addition, the method of the invention may be used to provide a bioactive agent delivery profile that may not be readily obtainable using a single delivery method. For example, a sustained release delivery device of method A or B may be used concurrently with method C in order to provide both a high initial concentration of a bioactive agent in the vitreous humor and sustained delivery (e.g., vitreal or subretinal) of the bioactive agent over an extended period of time. In another embodiment, methods A and B may be used concurrently to provide sustained vitreal and subretinal delivery of one or more bioactive agents.

Methods and devices of the invention can be used to instill one or more bioactive agents to the eye for the treatment of ocular conditions, for example, retinal detachment; occlusions; proliferative retinopathy; proliferative vitreoretinopathy; diabetic retinopathy; inflammations such as uveitis, choroiditis, and retinitis; degenerative disease (such as age-related macular degeneration, also referred to as AMD); vascular diseases; and various tumors including neoplasms.

The methods and devices useful to deliver one or more bioactive agents according to the method of the invention are now described in detail below.

Method A: Intraocular Sustained Release Delivery Device:

Embodiments of the invention comprise the use an intraocular sustained release delivery device in order to controllably release one or more bioactive agents to the vitreous humor of the eye. Representative examples of intraocular sustained release delivery devices are described, for example, in U.S. Pat. No. 6,719,750 B2 ("Devices for Intraocular Drug Delivery," Varner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and related applications.

Referring now to FIGS. 1-5, a sustained release delivery device according to one embodiment is illustrated. Generally speaking, the device illustrated in FIGS. 1-5 provides a controlled release bioactive agent delivery device comprising a body member having a direction of extension, a longitudinal axis along the direction of extension, and a proximal end and a distal end, wherein at least a portion of the body member deviates from the direction of extension, the body member including a polymer matrix comprising a bioactive agent. As shown in FIG. 1, the device includes a body member 2 having a proximal end 4 and a distal end 6. FIG. 1 illustrates the body member in a coil configuration.

Figure 2:
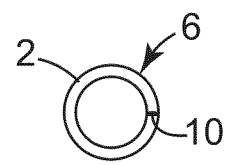
FIG. 2 shows a view from the bottom of the embodiment illustrated in FIG. 1.

The distal end 6 of the body member 2 can be positioned at any desirable location relative to the longitudinal axis of the body member. As shown in FIGS. 1-2, the distal end 6 of the body member according to one embodiment of the invention can include a tip 10 that is spaced from the longitudinal axis. This configuration is similar to a standard "cork screw" type configuration. In use, the device is inserted through the incision site and then twisted until the controlled delivery device is properly positioned at the treatment site.

Figure 3:
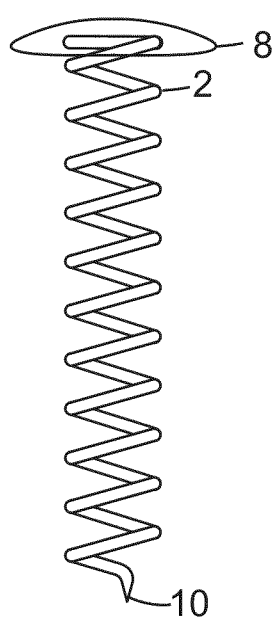
FIG. 3 shows a perspective view of an implantable device configured for intraocular placement according to another embodiment of the invention.
Figure 4:
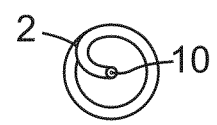
FIG. 4 shows a view form the bottom of the embodiment illustrated in FIG. 3.

Another embodiment is shown in FIGS. 3-4, wherein the distal end 6 of the body member includes tip 10 that is positioned at the longitudinal axis of the body member 2. In some embodiments, placement of the tip 10 of the body member 2 at the longitudinal axis can provide advantages, such as ease of insertion of the device at the distal end. It will be readily apparent that various other configurations of the distal end of the body member can be provided, depending upon the desired application.

Further, the proximal end 4 of the body member 2 can also be positioned at any desirable location relative to the longitudinal axis of the body member. FIGS. 1 and 3 illustrate the proximal end 4 of the body member as spaced from the longitudinal axis. However, the proximal end 4 of the body member can be provided at the longitudinal axis as well (not shown in the FIGS.). In some embodiments, placement of the proximal end 4 of the body member 2 at the longitudinal axis can provide advantages, such as ease of fabrication of the device, increased mechanical strength, improved translation of force (since a uniform force can be applied and translated to the body member, with less risk of bending or other deformation of the body member), and the like.

According to the intraocular embodiments of the invention, the coil shape of the body member allows the device to be screwed or twisted into the body through an incision approximately the same size as the outer diameter of the material forming the body member 2. Still further, the coil shape of the body member can act as an anchoring mechanism to maintain the controlled delivery device within the implantation site, and can prevent unwanted movement of the device and unwanted ejection of the device from the implantation site and/or the body. As a result of the coil shape, the controlled delivery device is twisted and unscrewed out of the body during removal of the device.

Generally speaking, the body member of the implantable device is the portion of the controlled release device that is inserted into a patient. The body member can be described as including a proximal end (which is located, upon implantation, towards the exterior of the body), a distal end (which is located, upon implantation, towards the interior of the body), and a longitudinal axis. In use, at least a portion of the body member is inserted into a patient's body. For example, in some embodiments, it can be preferable to position less than 100% of the body member inside the patient's body. The amount of the body member positioned within the body can be determined by the interventionalist, based upon such factors as desired treatment parameters, the particular configuration of the device, the implantation site, and the like.

The body member further includes a direction of extension, and in preferred embodiments, at least a portion of the body member deviates from the direction of extension. In preferred embodiments, the body member includes at least two, three, four, five, six, seven, eight, nine, ten, or more deviations from the direction of extension. In some alternative embodiments, where the body does not include multiple deviations from the direction of extension, the body member can be provided in a "J" or a hook-type configuration.

The deviations from the direction of extension can be provided in any suitable configuration. Exemplary embodiments of such deviations will be described herein for illustrative purposes only, and without intending to be bound by any particular embodiment described herein. The deviations need not be rounded or arcuate. For example, in some embodiments, the body member is provided with a Z-shaped configuration, such that the deviations are angular. Moreover, the deviations need not be in a regular pattern, but can alternatively be provided in a random manner, such that the body member contains random curls or turns. In some embodiments, the deviations are provided in a patterned configuration about the longitudinal axis. Examples of these patterned embodiments include coils, spirals, or patterned Z-shaped turns in the body. Alternatively, the deviations can be provided in a random or non-patterned configuration about the longitudinal axis. According to these particular non-patterned embodiments, the distance of the individual deviations from the longitudinal axis to the outermost periphery of the body member can be selected to provide a desired overall profile of the body member, depending upon the application of the device. For example, it can be desirable, in some applications, to provide an overall profile of the body member having an hourglass shape, alternating ring circumference shapes, and the like.

In some embodiments, the deviations from the direction of extension can be provided in the form of rings. Such individual rings can be concentric (that is, having a common axis, or being coaxial about the longitudinal axis) or eccentric (deviating from a circular path). According to these embodiments, the individual rings are noncontiguous along the body member length, thereby forming individual ribs at positions along the direction of extension of the body member.

Preferred configurations of the body member are coiled or spiral. Generally, in a coil configuration, the individual rings of the coil rotate about the longitudinal axis, and the overall coil is substantially symmetrical about the longitudinal axis. A preferred coil is composed of multiple rings that are substantially similar in circumference along the length, from proximal to distal, of the device. In some preferred embodiments, the rings form a spiral pattern, wherein the circumference of the rings changes over the length of the device. Preferably, the circumference of the rings decreases toward the distal direction of the device, so that the largest ring circumference is located at the proximal region of the device, and the smallest ring circumference is located at the distal region of the device.

Inclusion of deviating portions of the body member provides an increased surface area for delivery of a bioactive agent to an implantation site as compared to a linear device having the same length and/or width. This can provide advantages during use of the device, since this configuration allows a greater surface area to be provided in a smaller length and/or width of the device. For example, in some applications, it can be desirable to limit the length of the device. For example, as will be discussed in more detail herein, it is desirable to limit the length of implants in the eye to prevent the device from entering the central visual field of the eye and to minimize risk of damage to the eye tissues. By providing a body member that has at least a portion of the body member deviating from the direction of extension, the device of the invention has greater surface area (and thus can hold a greater volume of bioactive agent) per length of the device without having to make the cross section of the device, and thus the size of the insertion incision, larger.

Still further, in certain embodiments, the shape of the body member can provide a built-in anchoring system that reduces unwanted movement of the device and unwanted ejection of the device out of the patient's body, since the shape of the body member requires manipulation to remove it from an incision. For example, for a coil-shaped body member, the device would require twisting, and a Z-shaped body member would require back and forth movement, to remove the device from the implantation site. According to some preferred embodiments, the device does not require additional anchoring mechanisms (such as suturing) to the body tissues, as a result of the self-anchoring characteristics of the device itself. As described in more detail herein, inclusion of a cap 8 on the device can provide further anchoring features of the device.

In some embodiments, when the body member includes two or more deviations from the direction of extension, the spacing of the individual deviations can be selected to provide an optimum combination of such features as increased surface area available for coating, overall dimensions of the device, and the like. For example, when the body member is provided in the form of a coil that includes two or more deviations from the direction of extension, the distance between the individual coils can be selected to be equal to or greater than the diameter of the material forming the body member. In some aspects, if the distance between coils is less than the diameter of the material forming the body member, the amount of surface area available for coating of the body member can decrease, since it can be more difficult to access portions of the surface area of the body member with the coating compositions. In one illustrative embodiment of this aspect of the invention, the body member is formed of a material having a diameter of 0.5 mm, and the distance between each coil of the body member is at least 0.5 mm. These principals can be applied to any configuration of the body member and is not limited to coiled configurations.

The overall dimensions of the implantable device can be selected according to the particular application. For example, the length and/or width of the device can be selected to accommodate the particular implantation site. Some factors that can affect the overall dimensions of the implantable device include the potency of any bioactive agent to be delivered (and thus the volume of bioactive agent required, which impacts the surface area of the device, as discussed herein), the location of the implantation site within the body (for example, how far within the body the implantation site is located), the size of the implantation site (for example, a small area such as the eye or inner ear, or a larger area, such as a joint or organ area), the tissue surrounding the implantation site (for example, vascular tissue or hard, calcinous tissue, such as bone), and the like.

By way of example, the device is preferably designed for insertion through a small incision that requires few or no sutures for scleral closure at the conclusion of the surgical procedure. As such, the device is preferably inserted through an incision that is no more than about 1 mm in cross-section, for example, in the range of about 0.25 mm to about 1 mm in diameter, preferably in the range of about 0.25 mm to about 0.5 mm in diameter. As such, the cross-section of the material forming the body member 2 is preferably no more than about 1 mm, for example, in the range of about 0.25 mm to about 1 mm in diameter, preferably in the range of about 0.25 mm to about 0.5 mm in diameter. When the material forming the body member 2 is not cylindrical, the largest dimension of the cross-section can be used to approximate the diameter of the body member for this purpose, for example, when the body member cross-section is square.

The body member of the controlled release device preferably has a total length from its proximal end to its distal end that is less than about 1 cm, for example, in the range of about 0.25 cm to about 1 cm. Upon implantation, the body member is positioned within the eye, such that the portion of the controlled delivery device that delivers bioactive agent to the eye chamber is positioned near the posterior segment of the eye. When the controlled delivery device includes a cap 8, the cap is preferably provided with a thickness of less than about 1 mm, more preferably less than about 0.5 mm. According to this particular embodiment, the total length of the controlled delivery device is less than about 1.1 cm, preferably less than about 0.6 cm.

The distal end 6 of the body member can include any suitable configuration, depending upon the application of the device and the site of the body at which the device is to be implanted. For example, in some embodiments, the distal end 6 can be blunt or rounded. In preferred embodiments, the distal end 6 of the body member is configured to pierce the body during implantation of the device into the body. For example, the distal end 6 of the body member can include a sharp or pointed tip. In one preferred embodiment, the distal end 6 of the body member has a ramp-like angle. Preferably, the device according to this embodiment can be utilized to make an incision in the body, rather than requiring separate equipment and/or procedures for making the incision site. If the distal end 6 of the body member 2 is used to pierce the body during insertion, at least the distal end 6 is preferably fabricated of a rigid, non-pliable material suitable for piercing the body. Such materials are well known and can include, for example, polyimide and similar materials. In one such preferred embodiment, the distal end 6 of the body member 2 is utilized to pierce the eye for insertion of the controlled delivery device in the interior of the eye.

In another preferred embodiment, the distal end 6 of the body member 2 can be shaped or bent to form a portion (for example, the distal-most portion of the body member) that is parallel to the longitudinal axis. In one embodiment illustrated in FIGS. 3 and 4, for example, the distal end 6 includes a sharp or pointed tip that is parallel to the longitudinal axis. According to this particular embodiment, the tip located at the distal end 6 of the body member is perpendicular to the plane of incision, thus providing a self-starting tip of the device. While the figures illustrate a sharp tip of the body member, it is understood that any suitable configuration of the distal tip can be provided, utilizing the teaching herein.

The body member 2 can be fabricated from a solid material (a material that does not contain a lumen) or a material containing a lumen, as desired. In the embodiment illustrated in FIGS. 1 to 4, for example, the body member 2 is fabricated from a solid material that is shaped into a coil. Alternatively, the body member 2 can be fabricated from a tubular material that includes a lumen. The choice of a solid or lumen-containing material is not critical to the invention and can be determined based upon availability of materials and processing considerations.

When included, the lumen(s) can extend along the length of the body member 2 or only a portion of the length of the body member 2, as desired. In some embodiments, the lumen(s) can serve as a delivery mechanism for delivery of a desired substance to the implantation site. The substance delivered via the lumen can comprise any of the bioactive agents described herein. The substance delivered via the lumen can be the same or different bioactive agent(s) from that included in the polymer matrix. Further, the substance can be provided in addition to the bioactive agent of the polymer matrix, or in place of the bioactive agent. For example, in one embodiment, one or more substances can be delivered via the lumen, and one or more bioactive agents can be provided to the implantation site from the polymer matrix.

In some embodiments, the lumen can contain a polymer matrix as described herein. According to these particular embodiments, the body member of the device can be provided with or without a coating on its external surface. In some such embodiments, the lumen can be utilized to deliver the bioactive agent(s) to the implantation site. For example, the lumen can contain the polymer matrix, including bioactive agent. According to this particular embodiment, the body member can be provided with a coating on an external surface comprising a suitable polymer only (that is, lacking any bioactive agent). Thus, the bioactive agent is provided to the implantation site in this embodiment principally via the lumen of the body member. In other embodiments, the lumen can include the inventive polymer matrix (including biodegradable polymer and bioactive agent), and the body member is not provided with a coated composition on its external surface.

The lumen can contain any combination of elements, as desired. For example, in some embodiments, the lumen can include only the substance to be delivered. In other embodiments, the lumen can include the substance to be delivered, as well as the polymer matrix. The particular combination of elements to be included in the lumen can be selected depending upon the desired application of the device.

When the lumen is to be provided with a substance and/or polymer matrix, the lumen can be filled with the desired substance and/or polymer matrix prior to inserting the device into the body, or after the device has been inserted into the body. When it is desired to fill the device with the substance after insertion into the body, a port can be provided near the proximal end 4 of the body member 2 for such purpose. The port is in fluid communication with the lumen(s) of the body member and can also be used for refilling the device with the substance and/or polymer matrix before and/or after implantation, when desired.

When the device includes a port, the port is preferably designed such that the needle of an injection mechanism (for example, a syringe) can be inserted into the port and the material to be included in the lumen injected by the injection mechanism. Thus, the material can travel through the port and into the lumen(s) of the body member. The port preferably forms a snug seal about the needle of the injection mechanism to prevent leakage of the material out of the port around the injection mechanism and to provide sterile injection of material into the lumen(s). If desired, fittings or collars (not shown), through which an injection mechanism can be inserted and which form a snug seal about the injection mechanism, can be mounted on the port. Upon injection of the material into the delivery device, the needle of the injection mechanism is removed from the port and the port sealed. Sealing can be accomplished by providing a removable cover (not shown) on the port that can be removed for injection of the substance and replaced when the material has been injected. In a preferred embodiment, the port is fabricated of a self-sealing material through which the injection mechanism can be inserted and which seals off automatically when the injection mechanism is removed. Such materials are known and include, for example, silicone rubber, silicone elastomers, polyolefin, and the like.

In further embodiments, when the device includes more than one lumen, the device can include more than one port. For example, each lumen can be in fluid communication with a plurality of ports. These ports are similar to the single port described above. If desired, the lumens and ports can be arranged such that each lumen can be filled with a different material through a corresponding port (for example, each lumen has its own dedicated port). It can be desirable to include more than one lumen when it is desirable to deliver more than one additional material to the implantation site.

In embodiments where it is desired to deliver one or more additional substances to the implantation site via one or more lumens, the individual lumens can include one or more apertures to allow such delivery. In one embodiment, such apertures are provided at the distal end 6 of the device. In other embodiments, the apertures are provided along the length of the body member 2. The number and size of the apertures can vary depending upon the desired rate of delivery of the substance (when provided) and can be readily determined by one of skill in the art. The apertures are preferably designed such that the substance to be delivered is slowly diffused rather than expelled as a fluid stream from the device. For example, when the device is implanted in the eye, it is preferable to deliver the substance through slow diffusion rather than expulsion of the substance as a fluid stream, which can damage the delicate tissues of the eye. In some embodiments, the polymer matrix in contact with the body can provide a particular porosity to the substance and can assist in controlling the rate of diffusion of the substance from the lumen. When included in the device, the particular location of the apertures can be situated so as to deliver the substance at a particular location once the device is implanted into the body.

In another embodiment, when the body member 2 includes a lumen for delivery of an additional substance to the implantation site, the material forming the body member 2 can be chosen to be permeable (or semi-permeable) to the substance to be delivered from the lumen. According to this particular embodiment, the material can be chosen depending upon the particular application of the device and the substance to be delivered and can be readily determined by one of skill in the art. Examples of suitable permeable materials include polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers, porous fibers, and the like.

According to these particular embodiments, the material used to fabricate the body member 2 can be chosen to provide a particular rate of delivery of the substance, which can be readily determined by one of skill in the art. Further, the rate of delivery of the substance can be controlled by varying the percentage of the body member 2 formed of the permeable (or semi-permeable) material. Thus, for example, to provide a slower rate of delivery, the body member 2 can be fabricated of 50% or less permeable material. Conversely, for a faster rate of delivery, the body member 2 can be fabricated of greater than 50% of permeable material. When one or more portions of the body member 2, rather than the whole body member 2, is fabricated of a permeable or semi-permeable material, the location of the permeable or semi-permeable material can be situated so as to deliver the substance at a particular location once the device is implanted at the implantation site.

In another embodiment, the lumen of the body member 2 can include impermeable dividers located along the length of the lumen. Thus, the lumen of the body member can contain a plurality of compartments, each of which can be filled with a different substance, as desired. These compartments could be filled prior to insertion through an injection port located, for example, in the side of each compartment. In another embodiment, the device can be filled after it is implanted by providing a plurality of conduits, each conduit in fluid communication with a corresponding compartment. These conduits can be provided within the wall of the body member 2, along the circumference of the body member 2. The substances could then be injected through a plurality of ports, each port in fluid communication with a corresponding conduit. Thus, a substance could be injected into the first compartment just below the cap 8 by a port in the center of the cap 8, which delivers the substance directly into the first compartment. A substance injected into the second port, would flow through conduit and would flow through an aperture in the wall of body member 2 into second compartment, and so on. The substance(s) to be delivered can be delivered to the implantation site via any of the methods described herein for the lumen(s).

In another embodiment, each lumen or compartment (as desired) can be designed for selected "opening" or activation by a laser (via heat or photodisruption). For example, a laser could be used to create apertures in the walls of the desired lumen and/or compartment when the particular substance is to be delivered. As such, release of each substance could be controlled upon demand by an interventionalist. Preferably, when a laser is utilized to create such apertures, the wavelength and temperature are controlled to minimize any effects on the polymeric coating composition.

In preferred embodiments, the body member 2 can be fabricated in a way that further increases the surface area of the body member, preferably without increasing the overall dimensions of the device. For example, in one embodiment, the device can be fabricated of multiple strands of material that are entwined or twisted around each other to form the body member 2 (for example, multiple strands of wire can be twisted around each other to form the body member). According to these particular embodiments, any number of individual strands can be utilized to form the body member, for example, 2, 3, 4, or more strands. The number of individual strands twisted to form the body member can be selected depending upon such factors as, for example, the desired diameter of the material forming the body member and/or the overall body member diameter, the desired flexibility or rigidity of the device during insertion and/or implantation, the size of the implantation, the desired incision size, the material used to form the body member, and the like.

As shown in FIG. 1, the body member 2 is preferably cylindrical in shape, with a circular cross-section. However, the cross-sectional shape of the body member 2 is not limited and, for example, can alternatively have square, rectangular, octagonal or other desired cross-sectional shapes.

As shown in FIGS. 1 and 3, a preferred embodiment can include a cap 8 positioned at the proximal end 4 of the body member 2. When included in the device, the cap 8 can assist in stabilizing the device once implanted in the body, thereby providing additional anchoring features of the device. Preferably, the device is inserted into the body through an incision until the cap 8 abuts the incision on the exterior of the body. If desired, the cap 8 can then be sutured to the body at the incision site to further stabilize and prevent the device from moving once it is implanted in its desired location. When the device is implanted in the eye, for example, the device can be inserted into the eye through an incision until the cap 8 abuts the incision. If desired, the cap 8 can then be sutured to the eye, to provide further stabilization as discussed above.

The overall size and shape of the cap 8 is not particularly limited, provided that irritation to the body at the incision site is limited. Preferably, the cap 8 is sized such that it provides a low profile. For example, the dimensions of the cap 8 are preferably selected to provide a small surface area to accomplish such desired features as additional anchoring characteristics of the device, without substantially increasing the overall profile of the device upon implantation. In some embodiments, for example, the cap can be covered by a flap of tissue at the incision site upon implantation, to further reduce potential irritation and/or movement of the device at the implantation and/or incision sites. One illustrative example described in more detail elsewhere herein is the covering of the cap with a scleral cap upon implantation of the device in the eye.

Further, while the cap 8 is illustrated with a circular shape, the cap can be of any shape, for example, circular, rectangular, triangular, square, and the like. In order to minimize irritation to the incision site, the cap preferably has rounded edges. The cap 8 is designed such that it remains outside the implantation site and, as such, the cap 8 is sized so that it will not pass into the implantation site through the incision through which the device is inserted.

As described herein, inclusion of a cap 8 in the device can provide additional anchoring features to the device itself. However, in some embodiments, it can be desirable to further secure the device to provide additional anchoring or securing features at the implantation site. Thus, when desired, the cap 8 can be further designed such that it can be easily sutured or otherwise secured to the surface surrounding the incision and can, for example, contain one or more holes (not shown) through which sutures can pass.

The materials used to fabricate the cap 8 are not particularly limited and include any of the materials previously described for fabrication of the body member 2. Preferably, the materials are insoluble in body fluids and tissues with which the device comes in contact. Further, it is preferred that the cap 8 is fabricated of a material that does not cause irritation to the portion of the body that it contacts (such as the area at and surrounding the incision site). For example, when the device is implanted into the eye, the cap 8 is preferably fabricated from a material that does not cause irritation to the portion of the eye that it contacts. As such, preferred materials for this particular embodiment include, by way of example, various polymers (such as silicone elastomers and rubbers, polyolefins, polyurethanes, acrylates, polycarbonates, polyamides, polyimides, polyesters, polysulfones, and the like), as well as metals (such as those described previously for the body member).

In some embodiments, the cap 8 can be fabricated from the same material as the body member 2. Alternatively, the cap 8 can be fabricated from a material that is different from the body member 2. The cap 8 can be fabricated separately from the body member 2, and subsequently attached to the body member 2, using any suitable attachment mechanism (such as, for example, suitable adhesives or soldering materials). For example, the cap 8 can be fabricated to include an aperture, into which the body member 2 is placed and thereafter soldered, welded, or otherwise attached. In alternative embodiments, the cap 8 and body member 2 are fabricated as a unitary piece, for example, utilizing a mold that includes both components (the body member 2 and cap 8) of the device. The precise method of fabricating the device can be chosen depending upon such factors as availability of materials and equipment for forming the components of the device.

In some aspects, and particularly when the body member is fabricated of a biodegradable material, the cap can be fabricated of a nondegradable material or a material that degrades more slowly than the degradable material forming the body member. This can be desirable, for example, to maintain the features provided by the cap (such as anchoring features) for a period of time at least as long as the time the body member retains some structural integrity at the implantation site. This can reduce risk of a significant intact portion of the body member breaking off the cap and losing an anchoring point at the implantation site.

In some embodiments, the cap 8 can be provided with a polymeric coating. According to these particular embodiments, the polymeric coating provided in connection with the cap 8 can be the same as, or different from, the polymeric coating provided in connection with the body member 2. For example, the particular bioactive agent included in the polymeric coating for the cap 8 can be varied to provide a desired therapeutic effect at the incision site. Exemplary bioactive agents that could be desirable at the incision site include antimicrobial agents, anti-inflammatory agents, and the like, to reduce or otherwise control reaction of the body at the incision site. It will be readily apparent upon review of this disclosure that the first polymer and second polymer can also be selected for the polymeric coating composition provided in connection with the cap 8, to provide a desired polymeric coating specific for the cap, when desired.

In some embodiments, the cap 8 can include a polymeric coating that is the same as the polymer coating provided in connection with the body member 2. According to these embodiments, the polymeric coating can be applied in one step to the entire controlled delivery device (body member and cap), if desired. Alternatively, the polymeric coating can be applied to the cap 8 in a separate step, for example, when the cap 8 is manufactured separately, and subsequently attached to the body member 2.

Figure 5:
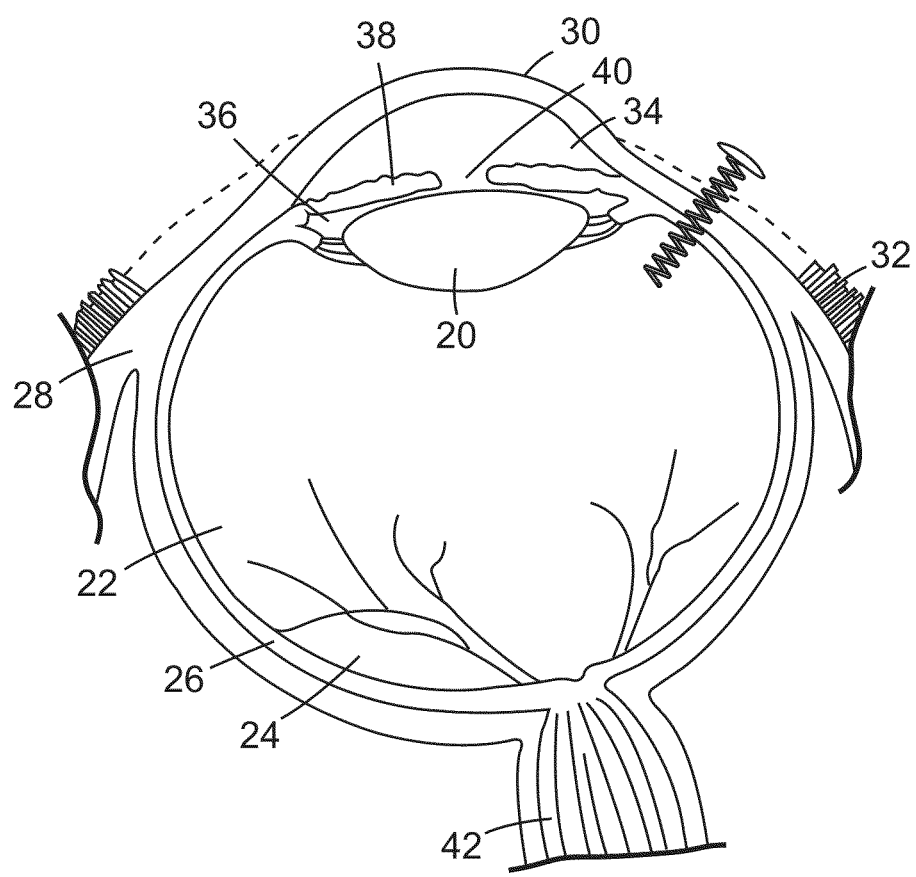
FIG. 5 shows transcleral placement of an implantable device according to one embodiment of the invention.

For intraocular delivery of one or more bioactive agents, the following procedure may be used. A sclerotomy can be created for insertion of the device into the posterior portion of the eye. Conventional techniques can be used for the creation of the sclerotomy. As shown in FIG. 5, such techniques include the dissection of the conjunctiva 32 and the creation of pars plana scleral incisions through the sclera 28. The dissection of the conjunctiva 32 typically involves pulling back the conjunctiva 32 about the eye so as to expose large areas of the sclera 28, and the clipping or securing of the conjunctiva 32 in that pulled back state (the normal position of the conjunctiva is shown in phantom). In other words, the sclera 28 is exposed only in the areas where the pars plana scleral incisions are to be made. Surgical instruments used in the procedure are then passed through these incisions. Thus, the incisions should be made large enough to accommodate the instruments required for the procedure.

Alternatively, the creation of the sclerotomy can be accomplished by use of an alignment device and method, such as that described in U.S. patent application Ser. No. 09/523,767, that enables sutureless surgical methods and devices thereof. In particular, such methods and devices do not require the use of sutures to seal the openings through which instruments are inserted. The alignment devices are inserted through the conjunctiva and sclera to form one or more entry apertures. Preferably, the alignment devices are metal or polyimide cannulas through which the surgical instruments used in the procedure are inserted into the eye.

In further embodiments, the device can be implanted directly through a self-starting transconjunctival trans-scleral "needle stick." For example, the body member 2 of the device can include a sharp tip 10, such as that illustrated in FIG. 3. According to this embodiment, the sharp tip 10 can be utilized to pierce the body and thereby create the incision site and access to the implantation site. In this case, no conjunctival surgery or extraneous alignment device is necessary.

In further embodiments, the conjunctival tissue can be dissected to expose a portion of the pars plana region, and a needle stick can be made into the sclera in the exposed region. A self-starting coil that includes a sharp tip is then inserted through the pars plana at the site of the needle stick, and the coil is rotated through the sclera until the cap of the device abuts the sclera. In some preferred embodiments, the needle stick is smaller than the diameter of the body member of the implantable device (for example, a 30-gauge needle stick can be used with an implantable device having a body member with a diameter of 0.5 mm or less). The conjunctival tissue is then pulled over the cap, to provide a flap or "seal" over the device, thus minimizing irritation of the implantation site, foreign body sensation, and the like. Optionally, the conjunctival tissue can be further secured by a single suture. In some embodiments the suture is biodegradable.

In some embodiments, it can be preferable to create an incision site that is slightly larger than the dimensions of the proximal portion of the body member. For example, when the device includes a cap 8 and is implanted into the eye, it can be preferable to create an incision that is larger than the largest diameter of the cap 8, such that the cap sits below the outer surface of the sclera. For example, a partial incision in the sclera can be made to create a scleral flap. Once the device has been implanted, and the cap 8 is placed so that it abuts the incision site, the scleral flap can be folded back over the device, thus providing a covering over the cap. Alternatively, when the proximal end of the body member does not include a cap 8, a flap-like cover can still be utilized to cover the proximal end of the device, in accordance with the description above. Preferably, these embodiments minimize the contact of the proximal end (for example, the cap 8) of the device with other body tissues, thereby reducing such risks as irritation of body tissues, and/or translation of movement of the eye to the device, thereby potentially damaging eye tissues. This can provide one or more advantages, such as reduced tendency for movement of the eye to be translated to the controlled delivery device, since the proximal end of the device will not be sitting at the surface of the eye and thus in contact with other body tissues; and reduced irritation of surrounding tissues.

The body member 2 is then inserted into the eye. For example, in embodiments wherein the body member 2 has a coil shape, the body member 2 is inserted into the eye by rotating or twisting the body member 2 into the eye until the cap 8 abuts the outer surface of the eye. In embodiments wherein the body member 2 is fabricated of a shape memory material, the shape memory material is first cooled to a temperature at which the martensite phase is stable and the device is deformed, for example, into a linear shape. The device is then inserted into the eye. To return the device to its memory shape, the device is left unrestrained and is simply allowed to reach a temperature (for example, by heating the device) above the martensite phase temperature. For example, the shape memory material can be heated by a laser to return the device to a temperature above the martensite phase temperature. The shape memory material can also be selected such that the martensite phase temperature is below body temperature so that the material is simply cooled to below body temperature, deformed to a linear shape, and inserted into the eye. Then, as the material warms up within the eye to body temperature, the device can return to its remembered shape. As discussed herein, when laser application is utilized, conditions are preferably controlled to maintain such parameters as wavelength and temperature, to minimize adverse effect on the polymeric coated composition.

FIG. 5 illustrates a controlled delivery device according to one embodiment of the invention that is implanted in the eye. When implanted into the eye, it is desirable to limit the length L of controlled delivery devices to prevent the controlled delivery device from entering the central visual field. If the device enters the central visual field, this can result in blind spots in the patient's vision and can increase the risk of damage to the retinal tissue and lens capsule. Thus, for example, when the controlled delivery device is inserted at the pars plana (as shown in FIG. 5), the distance from the implantation site on the pars plana to the central visual field is preferably less than about 1 cm.

Optionally, after the device is implanted into the eye, the cap 8 can then be sutured or otherwise secured to the sclera to maintain the controlled delivery device in place. In preferred embodiments, no further manipulation of the device is required for delivery of one or more bioactive agents to the interior of the eye. The conjunctiva can be adjusted to cover the cap 8 of the device, when desired, and the surgical procedure is completed.

In other embodiments, when a lumen is included in the device for delivery of one or more additional substances to the interior of the eye, further steps can be included as follows. If a cover is used to close the port(s), it is removed at this time, and if used, a collar for providing a snug fit about the injection mechanism (such as a syringe) is provided. The injection mechanism is then connected with the port(s) for injection of one or more substances to the controlled delivery device. If the port(s) are composed of a self-sealing material through which the needle of an injection mechanism can be inserted and which seals off automatically when the injection mechanism is removed, the injection mechanism is simply inserted through the port and the substance injected. Following injection, the conjunctiva can be adjusted to cover the cap 8 of the device, if desired.

Method B—Subretinal Instillation:

In some embodiments, the invention includes subretinal instillation (e.g., injection or implantation) of one or more bioactive agents in order to localize action of the bioactive agent(s) at the desired treatment site of the choroid and/or retina. The bioactive agent(s) that are delivered subretinally or in the subretinal space may be provided in any of a number of forms, for example, fluid solutions, solids, sustained release formulations, and sustained release delivery devices.

Representative examples of formulations for delivery of the bioactive agent into the subretinal space include, but are not limited to, injectable hydrogels, cyclodextrin "solubilized" and micronized solutions.

In embodiments where the bioactive agent(s) is initially provided in the form of a solid, such solids may be in the form of a capsule, pellet, rod, sheet, film, or hydrogel. Such solids can be configured and arranged so as to comprise a sustained release device for controllably releasing the bioactive agent to the tissues of the eye over an extended period of time. Examples of sustained release devices are found, for example, in U.S. Pat. Nos. 5,378,475 and 5,773,019. See also the related discussion in U.S. Pat. No. 6,217,895. The capsule or other structure forming the solid or the sustained release delivery device may be any suitable configuration, including cylindrical, rectangular, disk-shaped, patch-shaped, ovoid, stellate, or spherical. It is desirable, however, to use a configuration that does not tend to lead to migration from the subretinal space so as to minimize the potential for migration of the instilled bioactive agent from the targeted tissue site.

In some embodiments, sustained release delivery devices include, but are not limited to, flexible rods, thin films, foldable discs, biodegradable polymer with one or more bioactive agents embedded within, a bioactive agent-eluting polymer coating over a rigid scaffold, a compressed pellet of one or more bioactive agents, or one or more bioactive agents encapsulated in a semi-permeable membrane.

In some embodiments, the subretinal sustained delivery device is in the form of a biocompatible polymer capsule. Biocompatible polymer capsules contemplated for use with the methods of the invention comprise: (a) a core which contains one or more bioactive agents, either suspended in a liquid medium or immobilized within a biocompatible matrix, and (b) a surrounding jacket comprising a material that is biocompatible and permits diffusion of the bioactive agent to the tissues proximal the subretinal space. The core may comprise a biocompatible matrix of a hydrogel or other biocompatible matrix material that stabilizes the position of the bioactive agent. The jacket may be manufactured from various polymers and polymer blends including, for example, polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers, and mixtures thereof.

Figure 6:
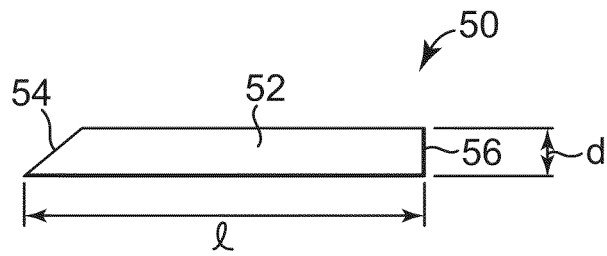
FIG. 6 shows and illustration of a subretinal sustained release delivery device in accordance with one embodiment of the invention.

In some embodiments, the subretinal sustained delivery device comprises a polymer matrix containing one or more bioactive agents. Referring to FIG. 6, an embodiment of a sustained delivery device 50 is shown. Sustained delivery device 50 comprises polymer matrix 52 which is embedded with one or more bioactive agents 54. Sustained delivery device 50 has proximal end 56 and distal end 58. In the embodiment of FIG. 6, distal end 58 is beveled to facilitate subretinal insertion. Alternatively, distal end 58 may be blunt, rounded, tapered, pointed, or other desired shape. Proximal end 56 may have the same end treatment as distal end 58 or it may have a different end treatment. For example, in the embodiment of FIG. 6, proximal end 56 is beveled and distal end 58 is blunt. Sustained delivery device 50 may have any desirable cross-sectional shape. For example, as shown in FIG. 6, the cross-sectional shape of sustained delivery device is circular. Alternatively, the cross-sectional shape may be triangular, square, rectangular, pentagaonal, octagonal, oval, and the like. Sustained delivery device 50 may be linear, as shown in FIG. 6, or may be non-linear. Examples of non-linear shapes include curved (e.g., "C" or "S" shaped), zig-zag (e.g., "Z" shaped), spiral, circular, and the like.

Figure 7:
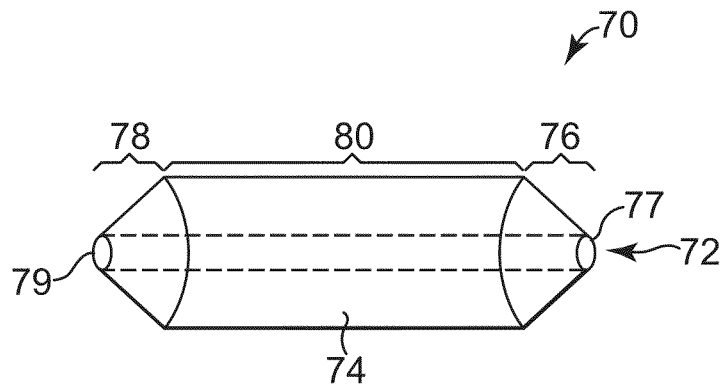
FIG. 7 shows an illustration of a side view of a subretinal sustained release delivery device.
Figure 7A:
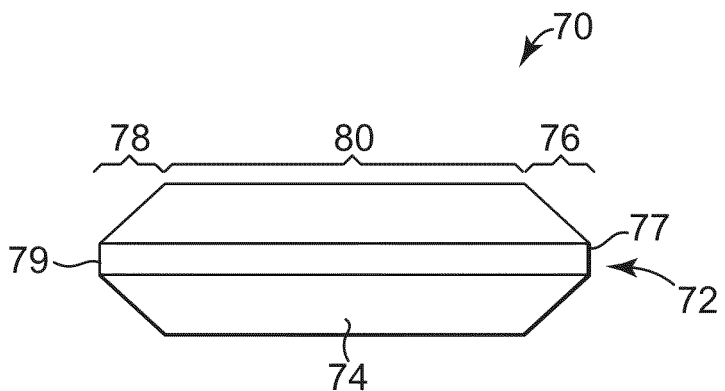
FIG. 7A shows a longitudinal cross-sectional view of the subretinal sustained release delivery device of FIG. 7.

In another embodiment, the device comprises a biocompatible core material that is coated with a coating layer of a polymer matrix and one or more bioactive agents. Referring to FIGS. 7-7A, one embodiment of a device of the type that has a core is shown. Device 70 includes core 72, having proximal end 77 and distal end 79, and coating layer 74 comprising polymer matrix and one or more bioactive agents. In the embodiment of FIGS. 7-7A, the coating layer 74 of polymer matrix and one or more bioactive agents is coated over the entire length of core 72. The coating layer 74 includes proximal transition segment 76, distal transition segment 78, and center portion 80. In this embodiment, proximal transition segment 76 and distal transition segment 78 have been feathered (i.e., a sloped transition segment).

Figure 8:
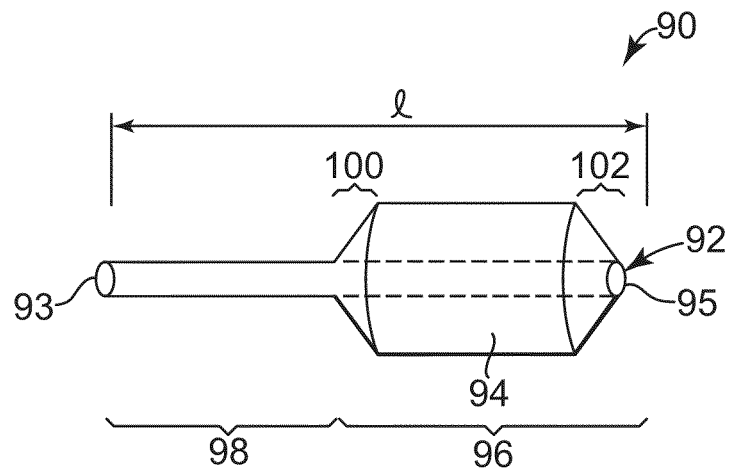
FIG. 8 shows an illustration of a side view of a sustained release delivery device in accordance with one embodiment of the invention.
Figure 8A:
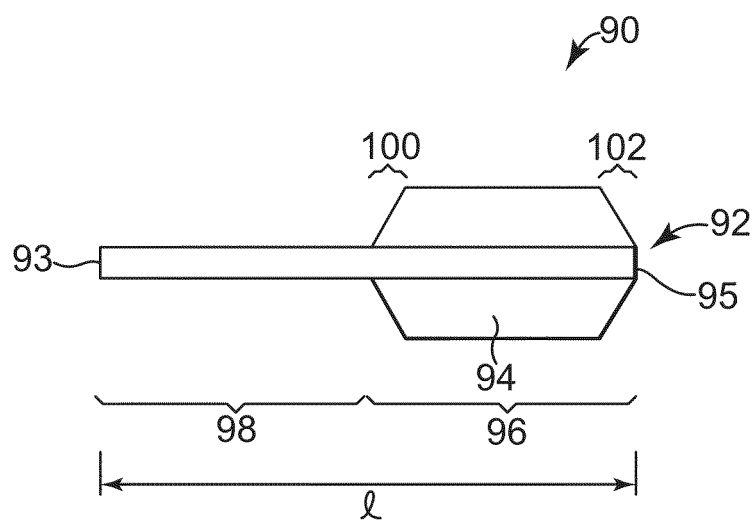
FIG. 8A shows a longitudinal cross-sectional view of the subretinal sustained release delivery device of FIG. 8.

In another embodiment, as shown in FIGS. 8-8A, device 90 includes core 92, having proximal end 93 and distal end 95. A coating layer 94 of polymer matrix-bioactive material is coated over a portion of the length "l" of core 92, resulting in coated portion 96 and uncoated portion 98. The uncoated portion 98 may be useful to provide a handling portion by which the device may be grasped or docked with a surgical instrument (e.g. by microsurgical instruments) to prevent any potential damage to the coating layer 94 upon handling. In one embodiment, the uncoated portion 98 of the device 90 could be left periretinal for easy retrieval in follow-up surgery. In the embodiment of FIGS. 8-8A, proximal transition segment 100 and distal transition segment 102 of coated portion 96 have been feathered (i.e., a sloped transition segment). Without being bound by theory, it is believed that feathering the distal and proximal ends of the device may enhance the uniformity, processing reproducibility, and ease of implantation.

The cross-sectional shape of the core may be any desired shape, but is typically circular. The diameter of the core (or maximum cross-sectional dimension, if not circular) is typically less than about 200 μm, in some embodiments ranging from about 10 μm to about 200 μm. The size, geometry and materials used in forming the core may be selected to provide desired characteristics to the device. For example, the material forming the core and the diameter (or maximum cross-sectional dimension) of the core may be selected to provide the desired rigidity and flexibility to the device. For example, a thin (i.e., small diameter) core material may be used if a less rigid device is desired. Thin core materials also allow for thicker coating layers, thereby maximizing the volume of bioactive agent(s) that may be contained in the device. The core material may also be selected to facilitate the ability of the polymer layer to adhere as a coating. For example, the surface of the core material may be primed, roughened, or chemically modified to facilitate adhesion of the polymer layer to the core material.

In some embodiments, the subretinal sustained delivery device (with or without the core material) may further include a layer of material that modifies the bioactive agent release rate characteristics. For example, a thin layer of polycaprolactone can be coated on the device. Such a polycaprolactone layer can also provide a degradation rate-controlling barrier, protection of the bioactive agent from environmental degradation prior to implantation, or even delay the time point of release of the drug.

In some embodiments, the outer diameter (or maximum cross-sectional dimension) of the sustained release delivery device is no greater than about 1000 μm in order to minimize retinal detachments and hemorrhaging. In other embodiments, the outer diameter (or maximum cross-sectional dimension) of the device is 900 μm or less, in other embodiments 800 μm or less, in other embodiments 700 μm or less, in other embodiments 600 μm or less, in other embodiments 500 μm or less, in other embodiments 400 μm or less, in other embodiments 300 μm or less, in other embodiments 200 μm or less, in other embodiments 100 μm or less, in other embodiments 100 μm or less. Typically, the diameter (or maximum cross-sectional dimension) ranges from about 200 μm to about 500 μm.

In some embodiments, the length of the sustained release delivery device is about 5.0 mm or less, in other embodiments about 4.5 mm or less, in other embodiments about 4.0 mm or less, in other embodiments about 3.5 mm or less. In a specific embodiment, the device is about 3.0 mm or less in length as such lengths have been found to provide the additional benefit of coming to a resting point in the eye that does not cross multiple tissue layers. However, it is possible to provide devices longer than about 3.0 mm that can be inserted with special care so as to minimize multiple tissue layer crossing. In other embodiments, the length of the device is 2.9 mm or less, in other embodiments about 2.8 mm or less, in other embodiments about 2.7 mm or less, in other embodiments about 2.6 mm or less, in other embodiments about 2.5 mm or less, in other embodiments about 2.4 mm or less, in other embodiments about 2.3 mm or less, in other embodiments about 2.2 mm or less, in other embodiments about 2.1 mm or less, in other embodiments about 2.0 mm or less. In some embodiments, the length of the device ranges from about 2.0 to about 3.0 mm.

As the device becomes smaller in diameter (or maximum cross-sectional dimension) or in length, the insertion and handling of the device may become more difficult and the amount of bioactive agent contained in the device will typically be reduced. Such factors may be taken into account when determining the diameter and/or length of the device.

The core may be a polymer matrix material as described herein or may be a non-polymer based material. Representative examples of non-polymer based materials include titanium-nickel alloy wire (e.g., Nitinol wire, commercially available from Nitinol Devices and Components, Freemont Calif.), titanium alloys, nickel-cobalt base alloys, stainless steel, cobalt-chromium alloys, and biodegradable magnesium alloys. It is to be understood that the core material is not limited to the examples provided herein and can be any conventional material used in implant devices. In some embodiments, the core comprises titanium-nickel wire. In one embodiment, the core is titanium-nickel wire having a diameter of about 80 µm (or the smallest commercially available diameter), in order to maximize the volume of bioactive agent in the device.

Subretinal sustained release delivery devices may be prepared by the steps of: (a) dissolving one or more polymers in a solvent to form a complex fluid; (b) adding one or more bioactive agents to the complex fluid to produce a homogeneous solution of the one or more bioactive agents and/or a solution with a dispersed phase of one or more bioactive agents; (c) optionally drying the complex fluid to a solid form; (d) optionally heating the solid form to a temperature just below the melting point of the polymer(s); and (e) forming the device out of the solution of (b) or the solid form of (c).

In some embodiments, the method comprises a low temperature process (e.g., from about 20° C. to about 100° C., more preferably from about 50° C. to about 90° C.). In one embodiment, the method comprises a process that involves homogenously mixing the polymer and one or more bioactive agents in solvent, drying, and melt-extrusion-drawing the prepared solid-form into the device shape. More specifically, the method comprises: dissolving one or more polymers in a suitable solvent solution to produce a complex fluid; adding one or more bioactive agents to the complex fluid to produce a homogeneous solution of one or more bioactive agents and/or a solution with a dispersed phase of one or more bioactive agents; drying the solution to a solid form; heating the solid form to a temperature below the melting point of the polymer (e.g., about 1° C. to about 5° C. below the melting point); forming the device out of this semi solid; and shaping the filament into the desired shape by drawing it into a lengthy filament and mechanically sectioning it into a fixed length. Bending the device can add curvature. In other embodiments the complex fluid is not dried to a solid form. In these embodiments, heating may not be required during the forming step because of the presence of the solvent in the complex fluid.

The steps of forming the subretinal sustained release delivery device and shaping the filament into the desired shape can be accomplished by a variety of conventional methods for forming and shaping a device out of a solid. For example, the solid form may be processed by melt-extrusion-drawing (applying tensile force) to form the solid into the desired shape and thickness. The length can be modified by cutting the device with any conventional cutting tool. The distal and/or proximal ends of the device can be shaped by cutting, sanding, and other methods for forming tapered, rounded, beveled and other desired end shapes.

Figure 20:
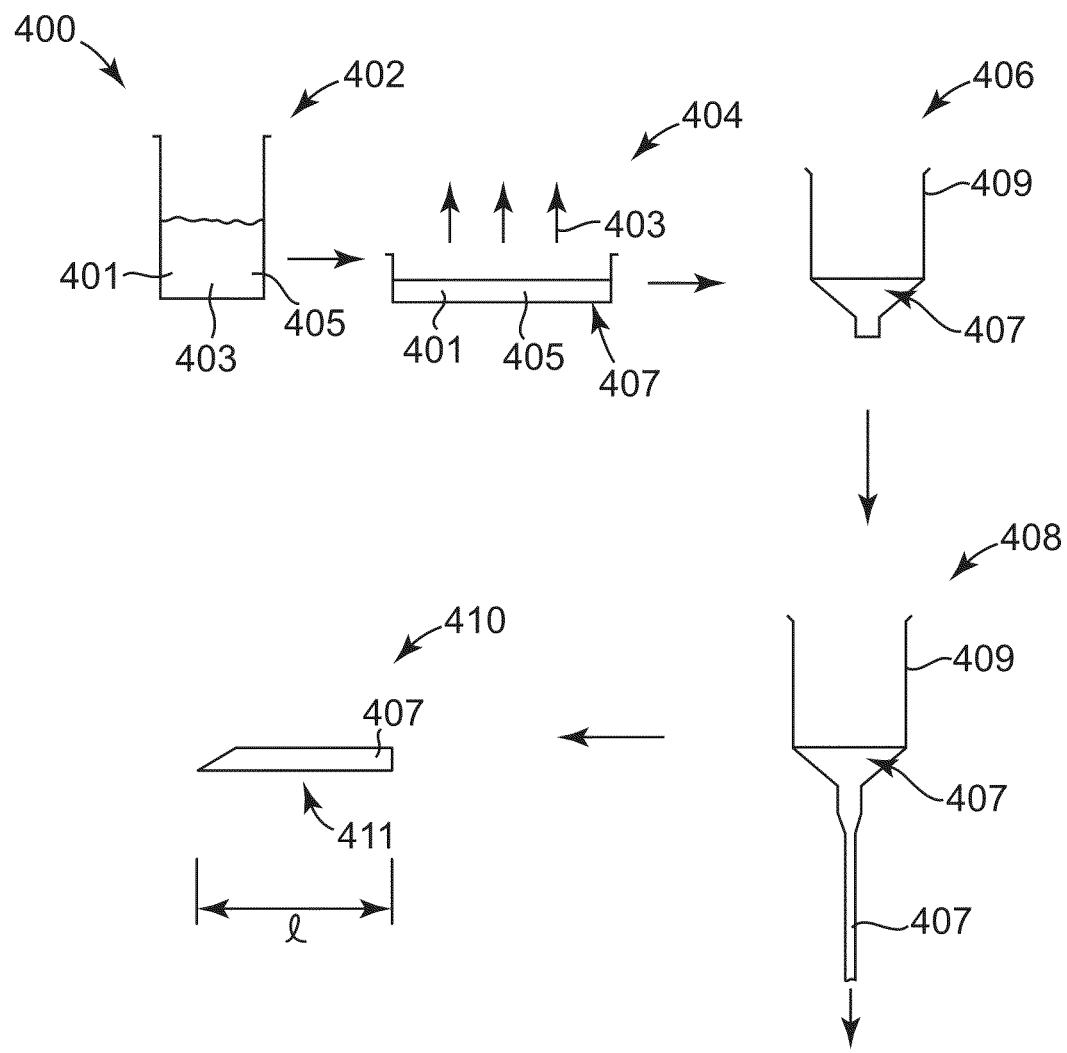
FIG. 20 is a schematic depiction of the filament preparation process in accordance with one embodiment of the present invention.

Referring to FIG. 20 a schematic depiction of an embodiment of a sustained release delivery device preparation process 400 is shown. As depicted in the figure, the device may be fabricated by: solubilizing polycaprolactone 401 in a solvent 403 at a temperature below boiling under still or continuous stirring conditions; adding one or more bioactive agents 405 to the solution in a ratio that preferably ranges from 1:99 to 70:30 (weight bioactive agent: weight polymer) (step 402); allowing the solvent 403 to evaporate under still or stirring conditions after the solution becomes translucent or dispersed (step 404); transferring the solid-form of the loaded polymer 407 to an extrusion device 409 (step 406); heating the extrusion device 409 to about 50° C. to about 90° C., depending on the molecular weight of the polycaprolactone ($M_n$=3,000 to 120,000), such that the polymer temperature approaches the melt temperature (but does not exceed it); drawing the solid-form of the loaded polymer 407 to its desired geometry once the extrusion device reaches the desired sub melt temperature (step 408); and shaping the resulting device 411 to the desired implantation length ("l") and shape after the temperature of the drawn implant falls (step 410).

In embodiments where the device includes a core, the device may be fabricated by applying a coating composition comprising one or more polymers and one or more bioactive agents over at least a portion of the outer surface of the core. The coating composition can be applied to the outer surface of the core using any suitable method. For example, the coating composition may be applied by dipping, spraying, and other known methods for applying coating compositions to substrates. The suitability of the coating composition for use on a particular material can be evaluated by those skilled in the art.

In some embodiments, the coating composition is applied to the core utilizing a precision coating system wherein the coating material is atomized ultrasonically (an ultrasonic coating system). Exemplary ultrasonic coating systems and methods are described in U.S. Published Application 2004/0062875 (Chappa et al.) and in U.S. application Ser. No. 11/102,465, filed Apr. 8, 2005, and entitled "Medical Devices and Methods for Producing Same."

Figure 9:
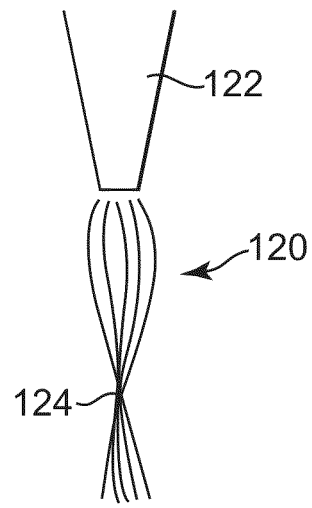
FIG. 9 is a schematic diagram of a spray stream as it passes through a focal point.
Figure 10:
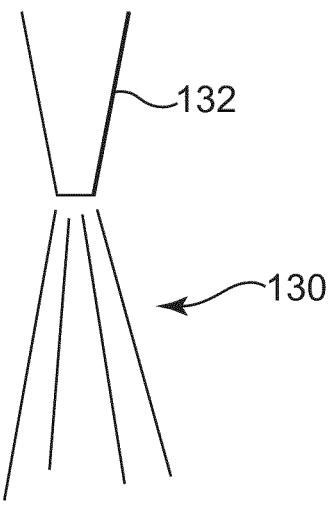
FIG. 10 is a schematic diagram of a spray stream that expands continuously as it moves away from the spray head.

In some embodiments, a core (e.g., a TiNi wire) to be coated is mounted in a pin vise, or other device that is capable of rotating the core about its longitudinal axis. The pin vice is rotated and an ultrasonic spray head is passed back and forth relative to the rotating core. Ultrasonic coating systems can produce a spray stream that narrows down as it moves away from the coating head. Referring now to FIG. 9, spray stream 120 narrows as it travels away from the coating head 122 before passing through a focal point 124 (or point of smallest spray stream diameter) before starting to expand. In an embodiment, the focal point has a cross-sectional diameter of about 0.5 mm to about 1.0 mm. In contrast, other types of spray systems frequently produce a spray stream that continuously expands in diameter as the stream leaves the spray head. For example, referring now to FIG. 10, the spray stream 130 continues to get wider as it travels away from the coating head 132.

Figure 11:
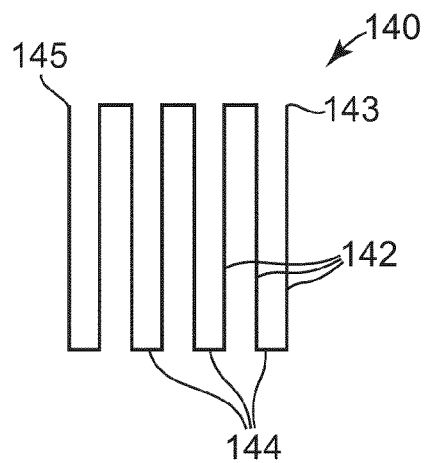
FIG. 11 is a schematic view of a grid-like coating pattern useful in coating devices of the invention.

Ultrasonic coating systems may be used to coat a core with a large degree of accuracy, particularly where the core to be coated is positioned at or near the focal point of the spray stream. This is because the spray stream has a relatively small cross-sectional area at or near the focal point because the spray stream has a relatively small amount of spray droplets that are outside of the focal point. As the spray stream has a relatively small cross-sectional area, the position of the spray stream with respect to the core must be moved if a broader area of the core is to be coated with a coating layer. Either the core or the spray head may be moved in order to coat a broader area.

In an embodiment, the ultrasonic spray head is moved back and forth over the rotating core in a grid-like pattern. By way of example, an exemplary grid-like pattern 140 is shown in FIG. 11. The grid-like pattern starts at point 143 and ends at point 145. The grid-like pattern has a series of transverse sweeps 142 and longitudinal movements 144. Depending upon the length of the longitudinal movements 144, any number of transverse sweeps can be used to cover the length of a given coating layer. In embodiments of the invention, the grid-like pattern 140 includes between 3 and 100 transverse sweeps 142. In embodiments of the invention, the grid-like pattern 140 includes between 3 and 100 longitudinal movements 144. The desired length of the longitudinal movements will depend upon a number of factors including the diameter of the spray pattern and the relative spray density of various parts of the spray pattern.

Figure 12:
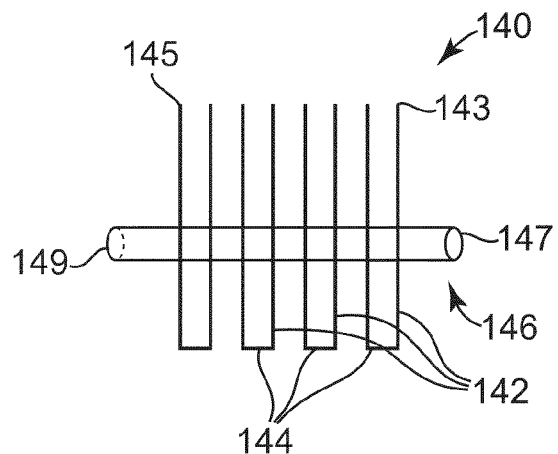
FIG. 12 is a schematic view of a grid-like coating pattern superimposed over a core material.

Referring now to FIG. 12, grid-like pattern 140 is superimposed over an exemplary core material 146 having distal end 147 and proximal end 149 to illustrate how core material 146 would be coated with reference to the grid-like pattern 140.

In some embodiments, the ultrasonic coating head follows the grid-pattern multiple times (that is, multiple passes) in order to deposit a coating layer onto a core. On each pass, an amount of the coating layer is deposited. Thus, the precise number of passes made by the ultrasonic coating head can be varied depending upon the total coating thickness desired. In some embodiments, the mass of the coating layer comprises between about 10 µg and about 1000 µg dry weight. In other embodiments, the mass of the coating layer comprises between about 50 µg to about 300 µg dry weight.

Figure 13:
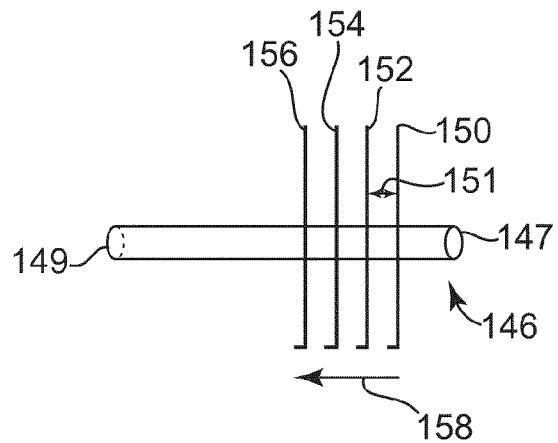
FIG. 13 is a schematic view of series of first transverse sweeps superimposed over a core material.

In some embodiments, the same longitudinal starting position is used with respect to the core for each pass of the ultrasonic coating head. For example, for each pass, the ultrasonic coating head would start at the same longitudinal point and follow the same pattern. In other embodiments, the longitudinal starting position of the ultrasonic coating head may change with each additional pass. Referring to FIG. 13, the first transverse sweep of the first pass may start at point 150. Then, the first transverse sweep of the second pass may start at an offset position 152 that is offset at a distance 151 from starting point 150. Similarly, the first transverse sweep of the third pass and fourth pass begin at points 154 and 156, respectively. This technique of moving the starting position in the direction of arrow 158 can be used to extend the distance over which the coating builds up to its full thickness thereby controlling the slope of the transition segment of the coating layer. By way of example, the offset distance between successive passes could be 0.5 mm. This would generally result in a longer transition segment with a lower slope in comparison with a coating layer that was applied with an offset between successive passes of less than 0.5 mm, for example 0.2 mm. The slope of the transition segment may be desirably low (e.g., less than about 1.0) when the device will undergo stresses (for example, frictional stresses) that may result in delamination or failure of the coating. The slope of the transition segment may be desirably high (e.g., greater than about 1.0) where it is desired to maximize the amount of the coating layer on the device. The proximal and distal transition segments of the coating layer may have slopes that are the same or different. For example, in some embodiments, the distal transition segment has a slope that is less than the proximal transition segment.

In some embodiments, the coating comprises at least two layers, wherein each layer comprises the same composition, or a different composition. In one such embodiment, a first layer having either bioactive agent alone, or bioactive agent together with one or more of the biodegradable polymers is applied, after which one or more additional layers are applied, each with or without one or more bioactive agents. These different layers, in turn, can cooperate in the resultant composite coating to provide an overall release profile having certain desired characteristics, and is particularly preferred for use with bioactive agents having high molecular weight. According to the invention, the composition of individual layers of the coating can include any one or more of the following: one or more bioactive agents, and/or a biodegradable polymer, as desired.

Preferably, the coating composition is applied to the core of the device in one or more applications. The method of applying the coating composition to the body member is typically governed by such factors as the geometry of the device and other process considerations. The coated composition can be subsequently dried by evaporation of the solvent. The drying process can be performed at any suitable temperature, (for example, room temperature or elevated temperature), and optionally with the assistance of vacuum.

In some embodiments, the coating composition is applied to the core under conditions of controlled relative humidity. As used herein, "relative humidity" is the ratio of the water vapor pressure (or water vapor content) to the saturation vapor pressure (or the maximum vapor content) at a given temperature of the air. The saturation vapor pressure in the air varies with air temperature: the higher the temperature, the more water vapor it can hold. When saturated, the relative humidity in the air is 100% relative humidity. According to some embodiments of the invention, the coating composition can be applied to the core under conditions of increased or decreased relative humidity as compared to ambient humidity.

According to the invention, humidity can be controlled in any suitable manner, including at the time of preparing and/or applying the coating composition to the body member. For example, when humidity is controlled at the time of preparing the coating composition, the water content of the coating composition can be adjusted, before and/or after the coating composition is applied to the body member. When humidity is controlled at the time of applying the coating composition, the coating composition can be applied to the body member in a confined chamber or area adapted to provide a relative humidity that differs from ambient humidity. Generally, it has been found that applying coating compositions under conditions of increased humidity will typically accelerate release of the bioactive agent, while applying coating compositions under conditions of decreasing humidity levels will tend to decelerate release of the bioactive agent. As contemplated in the invention, even ambient humidity can be considered "controlled" humidity if it has been correlated with and determined to provide a corresponding controlled release of the bioactive agent.

The bioactive agent to be administered may be concentrated to minimize the volume to be administered subretinally or into the subretinal space. After the liquid and the bioactive agent is administered or instilled subretinally, the surrounding tissues absorb the liquid and the bioactive agent resides subretinally (e.g., as a solid) and diffuses or otherwise is absorbed by the surrounding tissues of the eye over time. In this way, the methods of the invention provide a localized subretinal deposit of the bioactive agent within the eye. In addition, the action of the deposit or depot of the bioactive agent also is localized at the retina and the choroid.

The bioactive agent may include a pharmaceutically acceptable carrier or excipient and/or one or more accessory molecules which may be suitable for diagnostic or therapeutic use in vitro or in vivo. The term "pharmaceutically acceptable carrier" as used herein encompasses any of the standard pharmaceutical carriers, such as a phosphate buffered saline solution, water, and emulsions, such as an oil/water or water/oil emulsion, and various types of wetting agents. The bioactive agent may also include stabilizers and preservatives. For examples of carriers, stabilizers and adjuvants, see Martin *Remington's Pharm. Sci.,* 15th Ed. (Mack Publ. Co., Easton (1975)).

Figure 14:
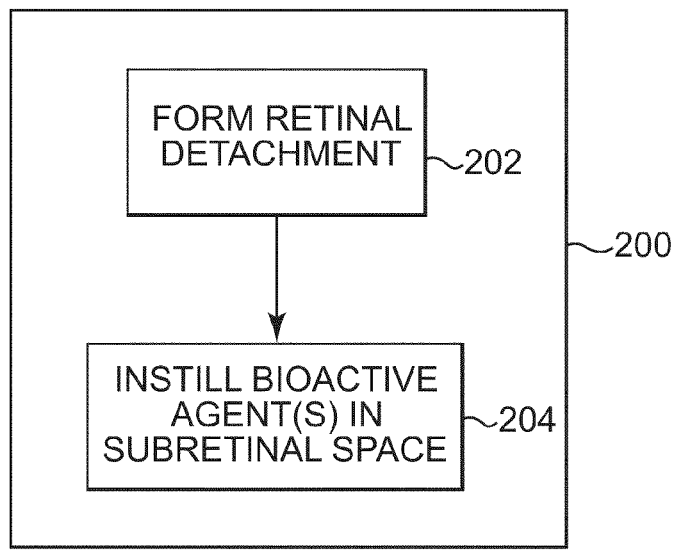
FIG. 14 is a flow diagram of a method of instilling one or more bioactive agents subretinally.

For subretinal instillation of one or more bioactive agent(s), the following procedure may be used. With reference to FIG. 14, the step of instilling the bioactive agent(s) (Step 200) includes forming a limited or localized retinal detachment (e.g., a bleb detachment) using any of a number of devices and/or techniques known to those skilled in the art (Step 202), thereby defining or forming a subretinal space and instilling (i.e., injecting or implanting) bioactive agent(s) into the subretinal space formed by the retinal detachment (Step 204). The limited or local subretinal detachment is created in such a fashion that the detachment itself generally does not have an appreciable or noticeable long-term effect on the vision of the patient. In more particular embodiments, the bioactive agent is instilled subretinally or in a subretinal space that is proximal to a given site or locus of particular tissues of the eye that require such treatment or are an appropriate pathway for effective delivery of the bioactive agent to tissues requiring treatment or prevention of the disease or disorder. In this way, the action of the bioactive agent is localized at the choroid and the retina and also minimizes the drug action at other tissue.

Methods of the invention bypass the mechanisms or barriers that may limit the effective delivery of bioactive agents when injected only directly into the vitreous, thereby permitting more sustained therapy to the target tissue. Locating the bioactive agent subretinally also minimizes the loss or removal of the bioactive agent from the eye such as expiration of the bioactive agent via the anterior segment of the eye after being initially located or injected in the vitreous. Subretinal locating of the bioactive agent minimizes the need for follow up injections, as typically needed with injections into the vitreous in order to maintain an adequate therapeutic concentration within the vitreous as well as minimizing the risks attendant with such injections to the vitreous. Further, because the bioactive agent is delivered directly to the subretinal space, it follows that higher concentrations of the bioactive agent is delivered to the choroidal vessels and retinal pigment epithelial cells as compared to intravitreal injection and intraocular implants that introduce drugs into the vitreous humor.

Figure 15:
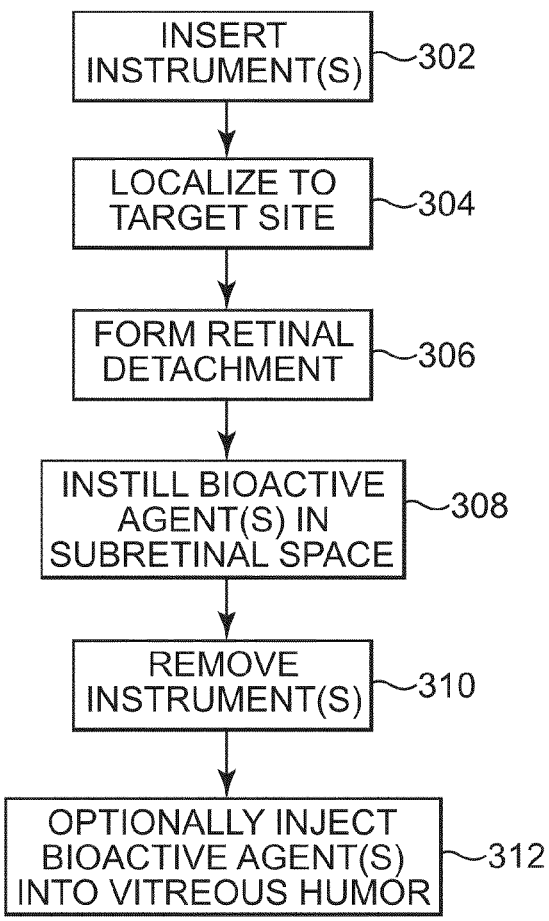
FIG. 15 is a flow diagram of a method of instilling one or more bioactive agents subretinally.

Now referring to FIG. 15, there is shown a flow diagram of an eye treatment methodology according to one embodiment of the invention, which methodology includes inserting a delivery device or delivery instrument into the eye to be treated (Step 302). The instrument being inserted can be any of a number of instruments known to those skilled in the art that can be used to form a retinal detachment. More particularly, the instrument is configured and arranged so as to be capable of forming a limited or localized retinal detachment and to minimize the area of the retinal detachment such that there is no long-term apparent loss in visual acuity.

In some embodiments, the step of inserting (Step 302) includes inserting a portion of the delivery instrument or device, such as the exemplary delivery device illustrated in U.S. Patent Application No. 2004/0133155 (Varner et al.), into the eye in a minimally invasive manner. This methodology also yields a technique that can be implemented in an outpatient clinic setting. According to this embodiment, a delivery instrument or device is provided, a portion of which is configured and arranged such that when the instrument is inserted into the eye, the opening formed in the sclera to receive the instrument is small enough so as to not require sutures to seal or close the opening in the sclera. In other words, the opening is small enough that the wound or opening is self-sealing, thereby preventing the aqueous humor from leaking out of the eye.

In addition, the step of inserting further includes inserting the insertable portion of the delivery instrument or device transconjunctivally so the operable end thereof is within the vitreous. In this regard, transconjunctival shall be understood to mean that the instrument's operable end is inserted through both the conjunctiva and through the sclera into the vitreous. More particularly, inserting the insertable portion that forms an opening in the sclera and the conjunctiva that is small enough so as to not require sutures or the like to seal or close the opening in the sclera. In conventional surgical techniques for the posterior segment of the eye, the conjunctiva is routinely dissected to expose the sclera, whereas according to the methodology of this embodiment, the conjunctiva need not be dissected nor pulled back.

Consequently, when the instrument is removed from the eye (step 310), the surgeon does not have to seal or close the opening in the sclera with sutures to prevent leaking of the aqueous humor because as indicated above such an opening or wound in the sclera is self-sealing. In addition, with the transconjunctical approach, the surgeon does not have to deal with reattaching the dissected conjunctiva. Thus, further simplifying the surgical procedure as well as reducing if not eliminating the suturing required under the surgical procedure.

After the insertable portion of the instrument is inserted into the eye, the operable end thereof is localized to the targeted site (Step 304) including the tissues that are being targeted for treatment. As is known to those skilled in the art, surgical personnel typically mount a lens assembly (not shown) onto the cornea of the eye in accordance with known and accepted practices and techniques. This lens assembly is provided so that the surgeon can view the interior of the eye as well as any instruments inserted therein. In addition, a light-transmitting apparatus as is known in the art also is inserted into the vitreous so as to be capable of providing a source of light therein for the surgeon. Accordingly, the surgeon would determine the positioning of the operable end of the instrument by viewing the interior of the eye using the lens assembly and being illuminated by the light transmitting apparatus.

After localizing the operable end of the instrument to the target site, for example the surface of the retina proximal the target site, the surgeon forms the limited retinal detachment (Step 306). In an illustrative exemplary embodiment, the surgeon forms the limited retinal detachment by injecting a fluid, such as liquid or gas, from the instrument's operable end. More specifically, the fluid is injected from the instrument's operable end in such a manner that the injected fluid is disposed between the retina and the choroid thereby causing the retina to detach therefrom. In more specific embodiments, the instrument's operable end is positioned such that the stream of fluid flowing from the operable end of the instrument is directed towards the targeted site of the retina and the stream of fluid pierces the retina and flows beneath the retina.

Figure 16:
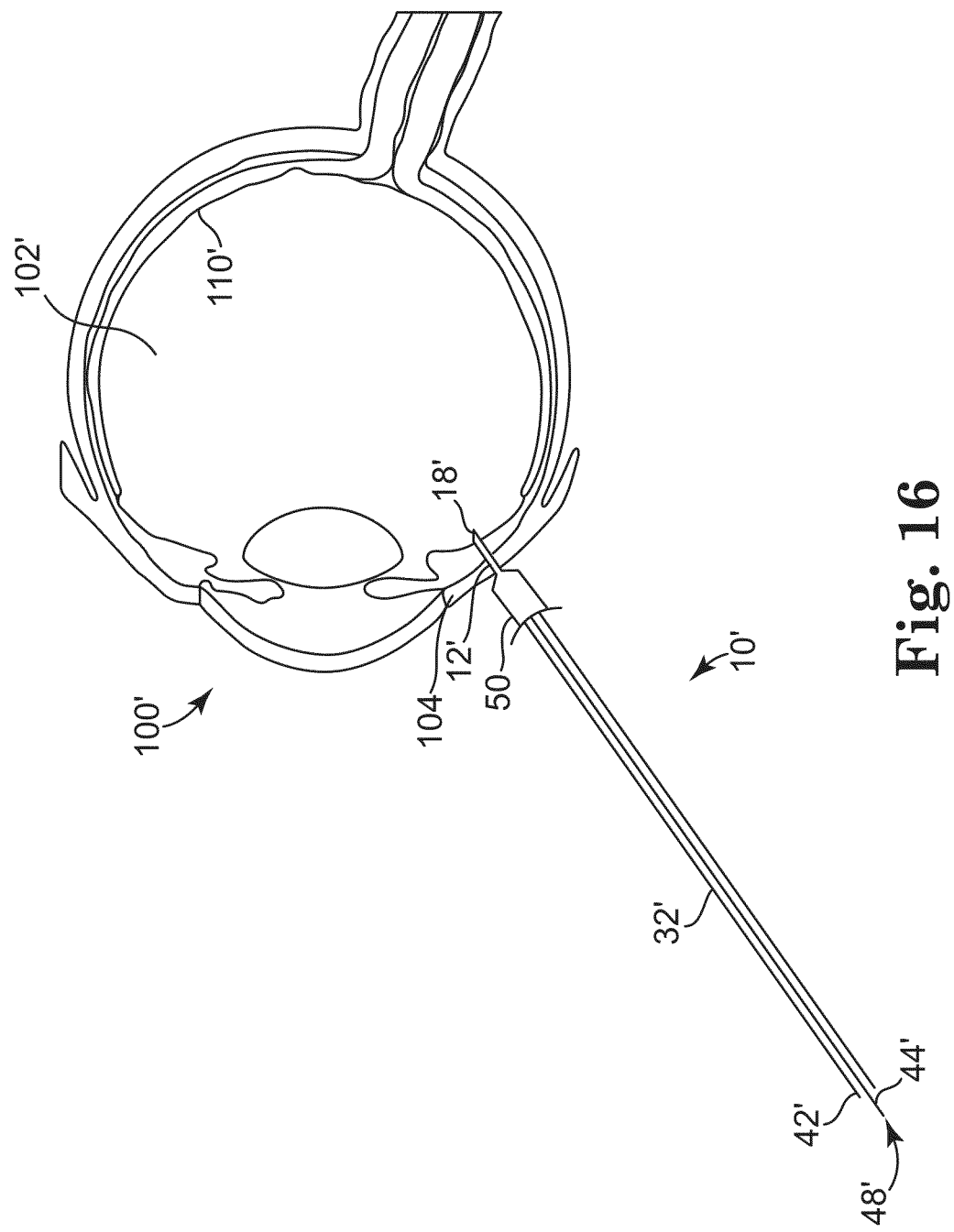
FIG. 16 is a schematic view illustrating the localization of the operable end of a subretinal bioactive agent delivery device.

Referring to FIG. 16, the sharp distal end 18' of the piercing member 12' is localized to a desired location on the surface of the conjunctiva or the sclera 104' of the eye 100'. A pressure or force is applied to the device 10' such that the sharp distal end 18' of the piercing member 12' penetrates the sclera 104' of the eye 100' or both the conjunctiva and sclera of the eye and the distal end is within the vitreous humor 102' of the eye 100'. This also thus creates a continuous passageway (not shown) between the device 10' and the vitreous humor 102' of the eye 100' providing a pathway for the surgeon to gains access to the vitreous humor.

The piercing member 12' also has a length such that once its proximal end 16' is in contact with a portion of the outer periphery of the sclera or the conjunctiva of the eye, the distal end 18' of the piercing member is within the vitreous humor 102' of the eye 100'. Once inserted the piercing member 12' can be angled by gently tilting or manipulating any portion of the device that lies outside of the eye 100'. In this way, the device 10' can be localized to multiple target sites within the eye without necessitating multiple, separate insertions of the device into the eye.

Once a passageway into the eye 100' is thus created, the cannula 44' and attached tubing 32', is advanced into and through the device 10' and localized to a treatment/target site. As illustrated in FIG. 17, the target site is the retina 110' of the eye 100'. The cannula 44' is guided through the device 10' until a distal portion 46' of the cannula emerges from the guiding member 12', and into the vitreous humor 102' and the cannula is further advanced within the eye 100' until the distal portion 46' of the cannula enters the retina 110'.

An operator of the device 10' is able to determine that the distal portion 46' of the cannula 44' has entered, but not traveled completely through, the retina 48' by virtue of techniques generally known in the art. For example, once an operator estimates that the distal portion 46' of the cannula is approaching the retina, s/he can inject an agent through the cannula 44'. In order to simplify this estimation, the cannula 44' can include one or more markings that serve as visual and/or tactile indicators of the relative position of the cannula with respect to the retina. If, following this injection, the formation of a retinal detachment is observed, the operator can safely deduce that the distal portion 46' of the cannula 44' has entered, and still remains within, the retina 110' and can halt the distal advancement of the cannula.

Referring now to FIG. 15, after forming the localized or limited retinal detachment (e.g., a bleb detachment), the bioactive agent is instilled (i.e., injected or implanted) in the subretinal spaced defined by the limited retinal detachment (Step 308). In the case, where the bioactive agent is in a liquid form or formulation, the instrument forming the retinal detachment can be used to inject the bioactive agent into the retinal detachment. Alternatively, a fluid including the bioactive agent can be used to form the retinal detachment and thereby simultaneously form the detachment and inject the bioactive agent. Thus, the forming of the detachment (Step 308) and the injection of the bioactive agent (step 310) are performed essentially simultaneously, thereby further simplifying the procedure or process.

Referring now to FIG. 18, in the case where the bioactive agent is in a solid or implantable form or formulation, the operable end 902 of the instrument may be further configured and arranged so to include a cannula 904 or lumen. The bioactive agent in its implantable form 910 such as a capsule, rod or sheet is disposed in the cannula or lumen prior to it being deployed there from subretinally. Thus, after forming the limited retinal detachment, the surgeon or medical personnel manipulates the instrument so that the bioactive agent in its implanted form 910 is dispensed from the end of the cannula 904 in the instrument's operable end 902 into the subretinal space formed by the limited retinal detachment. Alternatively, the surgeon or medical personnel can manipulate the implantable form of the bioactive agent so as to insert the bioactive agent at the same time as forming the retinal detachment. Such dispensing can be accomplished by mechanical action on the implantable form of the drug (e.g., a rod acting on the capsule form of the drug) or by fluid or hydraulic action on the implantable form.

After completing such injection or implanting, the instrument is removed from the eye (Step 310). Prior to sealing or closing the opening formed in the eye, one or more bioactive agent(s) may be injected into the vitreous humor using a small gauge needle and syringe (Step 312). Such bioactive agent(s) may be the same as the bioactive agents instilled subretinally or may be different than such bioactive agent(s). Following this, in the case where an incision was made in the sclera to insert the instrument, sutures would be used to close the incision. In addition, if the particular technique also involved dissection of the conjunctiva, the conjunctiva would be reattached to the eye. As indicated herein, if the technique used to form the opening yields an opening in the sclera small enough so as to be self sealing, suturing may not be required and for the transconjunctival technique, re-attachment of the conjunctiva should not be required.

Figure 19:
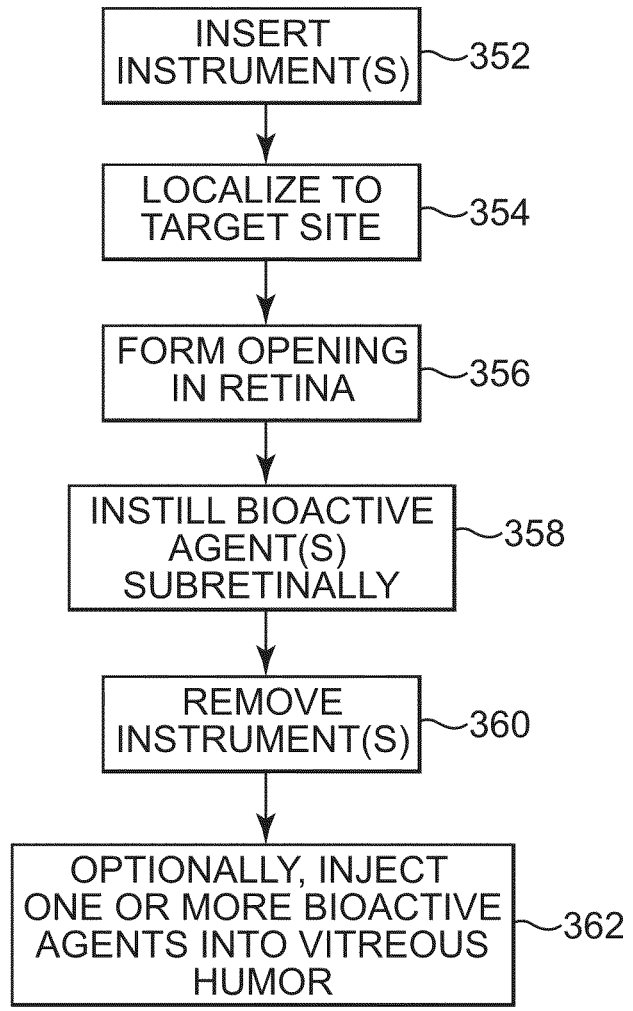
FIG. 19 is a flow diagram of a method of instilling one or more bioactive agents subretinally.

Referring now to FIG. 19, there is shown a flow diagram of an eye treatment methodology according to yet another embodiment of the invention, which methodology includes inserting a device or instrument into the eye to be treated (Step 352). The instrument being inserted can be any of a number of instruments known to those skilled in the art that can be used to pierce the tissues of the retina and form an opening or aperture therein so as to provide access to the area or region between the retina and choroids. In a particular illustrative embodiment of the invention, the opening or through aperture is formed by a small gauge needle that is disposed within the vitreous and manipulated by the surgeon so as to pierce the tissues of the retina. For example, a surgeon can use microforceps as is known to those skilled in the art that the surgeon would use to grip and manipulate the needle.

As previously described, the inserted instrument is localized to the targeted site (Step 354) that includes the tissues that are being targeted for treatment. As is known to those skilled in the art, surgical personnel typically mount a lens assembly (not shown) onto the cornea of the eye in accordance with known and accepted practices and techniques. This lens assembly is provided so that the surgeon can view the interior of the eye as well as any instruments inserted therein. In addition, a light-transmitting apparatus as is known in the art also is inserted into the vitreous so as to be capable of providing a source of light therein for the surgeon. Accordingly, the surgeon would determine the positioning of the operable end of the instrument by viewing the interior of the eye using the lens assembly and being illuminated by the light transmitting apparatus.

After localizing the operable end of the instrument to the tissues of the retina proximal the target site, the surgeon manipulates the instrument to penetrate or pierce the tissues of the retina as herein described (Step 356). As indicated hereinabove, this action preferably creates or forms an opening or through aperture in the retina of small diameter that provides access the area or region between the retina and the choroids. Preferably the opening or through aperture created or formed by such action generally does not have an appreciable or noticeable long-term effect on the vision of the person.

After forming the opening or aperture (Step 356), the surgeon then manipulates the form the bioactive agent is in so that the form of the bioactive agent is passed through the opening in the tissues of the retina and slide between the tissues of the choroid and the retina. In more particular embodiments, the bioactive agent is provided in the form of a sustained release device or other delivery device and the sustained release device or delivery device is manipulated by the surgeon so as it passes through the opening or aperture in the tissues of the retina and so it is slide subretinally between the tissues of the retina and the choroids (Step 358). After completion of the instilling of the bioactive agent(s), the surgeon removes the surgical instruments from the vitreous (Step 360). Optionally, the surgeon may inject one or more bioactive agents into the vitreous humor using a small gauge needle and syringe (Step 362). Such bioactive agent(s) may be the same as or different from the bioactive agent(s) instilled subretinally. As indicated herein, the process of inserting the instruments into the vitreous and removal preferably are accomplished using techniques whereby an opening(s) formed in the sclera for admission of the instruments into the vitreous is self-sealing. In addition, the technique used for inserting the instruments into the vitreous also is more particularly a transconjunctival technique whereby the instruments are inserted through both of the conjunctiva and the sclera.

In further embodiments, the bioactive agent is inserted or implanted through the retinal tissues semi-permanently or temporarily. Thus, in such further embodiments the methodology further includes inserting a withdrawal instrument (e.g., micro-forceps) into the vitreous following completion of the treatment phase and localizing the operable end of the withdrawal instrument proximal the target site, more particularly proximal the tissues containing the device. Thereafter, the surgeon manipulates the withdrawal instrument so as to withdraw the bioactive agent, for example, withdrawing the bioactive agent delivery device from the subretinal region. The bioactive agent is withdrawn from the vitreous along with any instruments. In yet further particular embodiments, the methodology of the invention contemplates insertion of another depot of bioactive agent, for example insertion of another delivery device with a fresh charge of bioactive agent, into the subretinal region following such withdrawal of the used device or bioactive agent.

Method C—Intravitreal Delivery:

In some embodiments, the method of the invention includes instilling one or more bioactive agents into the vitreous humor of the eye. The intravitreal delivery will typically be performed after implantation of the intraocular sustained release delivery device (see, Method A) and/or after instillation of the bioactive agent(s) subretinally (see, Method B). Typically, the intravitreal delivery will be accomplished by direct intravitreal injection of the one or more bioactive agents, for example, using a 27 to 30-gauge needle (or smaller) having a length of about 0.5 to about 0.62 inches. Alternatively, the intravitreal delivery may be accomplished using transscleral iontophoresis as discussed, for example, in Ashim K. Midra; *Ophthalmic Drug Delivery System*; $2^{nd}$ Edition (2004) at Chapter 12 (Marvin E. Myles et al., Ocular Inotophoresis). Iontophoresis is the direct transport of ionized substances through tissue by application of an external electric current. Bioactive agents having one or more pKa values either below pH 6 or above pK8 may be suitable for iontophoresis because these bioactive agents will be in their ionized form at the physiological pH of the eye. The salt form of the bioactive agent may also be preferred. The bioactive agent is driven into the ocular tissue with an electrode carrying the same charge ionized form as the bioactive agent. In transscleral iontophoresis the electrical current is applied through the pars plana. Specifically, for transscleral iontophoresis the bioactive agent is contained in a tube within an eyecup held to the conjunctiva by suction. The tube is placed over the pars plana to avoid current damage to the retina.

Devices for iontophoresis are commercially available from a number of sources, for example, Iomed, Inc. (Salt Lake City, Utah); Life-Tech, Inc. (Stafford, Tex.); General Medical Co. (Los Angeles, Calif.); and Fischer Co., Inc. (Glendale Calif.).

The one or more bioactive agents instilled into the vitreous humor may be the same as the one or more bioactive agents in the intraocular device (Method A) or instilled subretinally (Method B), or the bioactive agent(s) may be different. The bioactive agent(s) are typically injected as liquids. The volume will depend, for example, on the method of treatment, the type of bioactive agent(s) being injected, the concentration of the bioactive agent(s), disease state, location of disease and affected tissue. Typically the volume of the injection will be up to about 500 μL, more typically from about 50 μL to 500 μL. Additional details regarding intravitreal injections can be found, for example, in Lloyd P. Aiello, M D et al., Evolving Guidelines For Intravitreous Injections, *The Journal of Retinal and Vitreous Diseases*, Vol. 24, No. 5 (2004).

The methodologies of the invention are contemplated as being practiced alone, or in combination with other therapies or treatments. For example, where laser treatment of an eye is indicated, the method of the invention can be practiced before and/or after the laser treatment.

Bioactive Agents:

As used herein, "bioactive agent" refers to an agent that affects physiology of biological tissue. Bioactive agents useful according to the invention include virtually any substance that possesses desirable therapeutic and/or prophylactic characteristics for application to the implantation site.

While reference may be made to a "bioactive agent," it will be understood that the invention can provide any number of bioactive agents to a treatment site. Thus, reference to the singular form of "bioactive agent" is intended to encompass the plural form as well.

Exemplary bioactive agents include, but are not limited to, thrombin inhibitors; antithrombogenic agents; thrombolytic agents (such as plasminogen activator, or TPA: and streptokinase); fibrinolytic agents; vasospasm inhibitors; calcium channel blockers; vasodilators; antihypertensive agents; clotting cascade factors (for example, protein S); anti-coagulant compounds (for example, heparin and nadroparin, or low molecular weight heparin); antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, minocycline, doxycycline, vancomycin, kanamycin, cephalosporins such as cephalothin, cephapirin, cefazolin, cephalexin, cephardine, cefadroxil, cefamandole, cefoxitin, cefaclor, cefuroxime, cefonicid, ceforanide, cefitaxime, moxalactam, cetizoxime, ceftriaxone, cefoperazone), geldanamycin and analogues, antifungals (such as amphotericin B and miconazole), and antivirals (such as idoxuridine trifluorothymidine, acyclovir, gancyclovir, interferon, α-methyl-P-adamantane methylamine, hydroxy-ethoxymethyl-guanine, adamantanamine, 5-iodo-deoxyuridine, trifluorothymidine, interferon, adenine arabinoside); inhibitors of surface glycoprotein receptors; antiplatelet agents (for example, ticlopidine); antimitotics; microtubule inhibitors; anti-secretory agents; active inhibitors; remodeling inhibitors; antisense nucleotides (such as morpholino phosphorodiamidate oligomer); anti-metabolites; antiproliferatives (including antiangiogenesis agents, taxol, sirolimus (rapamycin), analogues of rapamycin ("rapalogs"), tacrolimus, ABT-578 from Abbott, everolimus, paclitaxel, taxane, vinorelbine); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); mydriatics (such as atropine, cyclopentolate, homatropine, scopolamine, tropicamide, eucatropine, hydroxyamphetamine); sympathomimetics (such as epinephrine); antineoplastics (such as carmustine, cisplatin, fluorouracil); immunological drugs (such as vaccines and immune stimulants); hormonal agents (such as estrogens, estradiol, progesterol, progesterone, insulin, calcitonin, parathyroid hormone, peptide and vasopressin hypothalamus releasing factor); beta adrenergic blockers (such as timolol maleate, levobunolol HCl, betaxolol HCl); immunosuppressive agents, growth hormone antagonists, growth factors (such as epidermal growth factor, fibroblast growth factor, platelet derived growth factor, transforming growth factor beta, somatotropin, fibronectin, insulin-like growth factor (IGF)); carbonic anhydrase inhibitors (such as dichlorophenamide, acetazolamide, methazolamide); inhibitors of angiogenesis (such as angiostatin, anecortave acetate, thrombospondin, anti-VEGF antibody such as anti-VEGF fragment—ranibizumab (Lucentis)); dopamine agonists; radiotherapeutic agents; peptides; proteins; enzymes; nucleic acids and nucleic acid fragments; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

Another group of useful bioactive agents are antiseptics. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Another group of useful bioactive agents are enzyme inhibitors. Examples of enzyme inhibitors include chrophonium chloride, N-methylphysostigmine, neostigmine bromide, physostigmine sulfate, tacrine HCL, tacrine, 1-hydroxymaleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor 1, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−)deprenyl HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate, R(+) p-aminoglutethimide tartrate, S(−)-3-iodotyrosine, alpha-methyltyrosine, L(−)alpha methyltyrosine, D,L(−)cetazolamide, dichlorophenamide, 6-hydroxy-2-benzothiazole-sulfonamide, and allopurinol.

Another group of useful bioactive agents are anti-pyretics and antiinflammatory agents. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances that have an anesthetic effect in a localized region. Examples of such anesthetics include procaine, lidocaine, tetracaine and dibucaine.

Other bioactive agents include abamectin, abundiazole, acaprazine, acabrose, acebrochol, aceburic acid, acebutolol, acecainide, acecarbromal, aceclidine, aceclofenac, acedapsone, acediasulfone, acedoben, acefluranol, acefurtiamine, acefylline clofibrol, acefylline piperazine, aceglatone, aceglutamide, aceglutamide aluminium, acemetacin, acenocoumarol, aceperone, acepromazine, aceprometazine, acequinoline, acesulfame, acetaminophen, acetaminosalol, acetanilide, acetarsone, acetergamine, acetiamine, acetiromate, acetohexamide, acetohydroxamic acid, acetomeroctol, acetophenazine, acetorphine, acetosulfone, acet: ozate, acetryptine, acetylcolchinol, acetylcysteine, acetyldigitoxin, acetylleucine, acetylsalicyclic acid, acevaltrate, acexamic acid, acifran, acipimox, acitemate, acitretin, acivicin, aclantate, aclarubicin, aclatonium napadisilate, acodazole, aconiazide, aconitine, acoxatrine, acridorex, acrihellin, acrisorcin, acrivastine, acrocinide, acronine, actinoquinol, actodigin, adafenoxate, adamexine, ademetionine, adenosine phosphate, adibendan, adicillin, adimolol, adinazolam, adiphenine, aditeren, aditoprim, adrafinil, adrenalone, afloqualone, afurolol, aganodine, ajmaline, aklomide, alacepril, alafosfalin, alanine mustard, alanosine, alaproclate, alazanine triclofenate, albendazole, albendazole oxide, albuterol, albutoin, alclofenac, alcometasone dipropionate, alcloxa, alcuronium chloride, aldioxa, aldosterone, alepride, aletamine, alexidine, alfacalcidol, alfadex, alfadolone, alfaprostol, alfaxalone, alfentanil, alfuzosin, algestone acetonide, algestone acetophenide, alibendol, aliconazole, alifedrine, aliflurane, alimadol, alinidine, alipamide, alitame, alizapride, allantoin, alletorphine, allobarbital, alloclamide, allocupreide, allomethadione, allopurinol, allylestrenol, allyl isothicyanate, allylprodine, allylthiourea, almadrate sulfate, almasilate, almecillin, almestrone, alminoprofen, almitrine, almoxatone, alonacic, alonimid, aloxistatin, alozafone, alpertine, alphacetylmethadol, alphameprodine, alphamethadol, alphaprodine, alpha-vinylaziridinoethyl acetate, alpidem, alpipride, alprazolam, alprenolol, alprostadil, alrestatin, altanserin, altapizone, alteconazole, althiazide, altrenogest, altretamine, aluminium acetate, aluminium clofibrate, aluminium subacetate, alverine, amadinone acetate, amafolone, amanozine, amantadine, amantanium bromide, amantocillin, ambasilide, ambazone, ambenonium chloride, ambenoxan, ambroxol, ambruticin, ambucaine, ambucetamide, ambuphylline, ambuside, ambutonium bromide, amcinafal, amcinafide, amcinonide, amdinocillin, amdinocillin pivoxil, amebucort, amedalin, ametantrone, amezepine, amezinium metilsulfate, amfenac, amfepentorex, amfetaminil, amflutizole, amfonelic acid, amicarbalide, amicibone, amicloral, amicycline, amidantel, amidapsone, amidephrine, amiflamine, amifloverine, amifloxacin, amifostine, amikacin, amikhelline, amiloride, aminacrine, amindocate, amineptine, aminobenzoic acid, aminocaproic acid, aminoethyl nitrate, aminoglutethimide, aminohippuric acid, aminometradine, aminopentamide, aminophylline, aminopromazine, aminopterin, aminopyrine, aminoquinol, aminoquinuride, aminorex, aminosalicyclic acid, aminothiadiazole, aminothiazole, amiodarone, amiperone, amipheazole, amipizone, amiprilose, amiquinsin, amisometradine, amisulpride, amiterol, amithiozone, amitraz, amitriptyline, amitriptylinoxide, amixetrine, amlexanox, amlodipine, amobarbital, amodiaquine, amogastrin, amolanone, amonofide, amoproxan, amopyroquin, amorolfine, amocanate, amosulalol, amotriphene, amoxapine, amoxecaine, amoxicillin, amoxydramine camsilate, amperozide, amphecloral, amphenidone, amphetamine, amphotalide, ampicillin, ampiroxicam, amprolium, ampyrimine, ampyzine, amquinate, aminone, amsacrine, amygdalin, amylene, amylmetacresol, amyl nitrite, anagestone acetate, anagrelide, anaxirone, anazocine, anazolene, ancarolol, ancitabine, androstanediol, androstanol propionate, androstenetrione, androstenonol propionate, anethole, anguidine, anidoxime, anilamate, anileridine, aniline, anilopam, anipamil, aniracetam, anirolac, anisacril, anisindione, anisopirol, anisoylbromacrylic acid, anitrazafen, anpirtoline, ansoxetine, antafenite, antazonite, anthelmycin, anthiolimine, anthralin, anthramycin, antienite, antimony potassium tartrate, antimony thioglycollate, antipyrine, antrafenine, apalcillin, apazone, apicycline, apomorphine, apovincamine, apraclonidine, apramycin, aprindine, aprobarbital, aprofene, aptazapine, aptocaine, arabinosylmercaptopurine, aranotin, arbaprostil, arbekacin, arclofenin, arfendazam, arginine, arginine glutamat, arildone, arnolol, aronixil, arotinolol, arpinocid, arpromidine, arsanilic acid, arsthinol, artemisinin, articaine, asaley, ascorbic acid, ascorbyl palmitate, asocainol, aspartame, aspartic acid, asperlin, aspoxicillin, astemizole, atamestane, atenolol, atipamezole, atiprosin, atolide, atracurium besilate, atromepine, atropine oxide, auranofin, aurothioglucose, aurothioglycanide, avilamycin-A, pyridine, axamozide, azabon, azabuperone, azacitodine, azaclorzine, azaconazole, azacosterol, azacyclonol, azaftozine, azaguanidine, azaloxan, azamethonium bromide, azamulin, azanator, azanidazole, azaperone; azapicyl, azaprocin, azaquinzole, azaribine, azarole, azaserine, azaspirium chloride, azastene, azastrptonigrin, azatodine, azathioprine, azauridine, azelastine, azepexole, azepindole, azetepa, azidamfenicol, azidocillin, azimexon, azintamide, azipramine, azithromycin, azlocillin, azolimine, azosemide, azotomycin, aztreonam, and azumolene.

Also, bacampicillin, baclofen, bacmecillinam, balsalazide, bamaluzole, bambuterol, bamethan, bamifylline, bamipine, bamnidazole, baquiloprim, barbexaclone, barbital, barucainide, batilol, bazinaprine, becanthone, beclamide, beclobrate, beclomethasone dipropionate, beclotiamine, befiperide, befunolol, befuraline, bekanamycin, belarizine, beloxamide, bemarinone, bemegride, bemetizide, bemitradine, benactyzine, benafentrine, benanserin, benapryzine, benaxibine, benazepril, bencianol, bencisteine, benclonidine, bencyclane, bendamustine, bendazac, bendazol, benderizine, bendroflumethiazide, benethamide penicillin, benexate, benflorex, benfosformin, benfotiamine, benfurodil hemisuccinate, benhepazone, benidipine, benmoxin, benolizime, benorilate, benorterone, benoxafos, benoxaprofen, benoxinate, benperidol, benproperine, benrixate, bensalan, benserazide, bensuldazic acid, bentazepam, bentemazole, bentiamine, bentipimine, bentiromide, benurestat, benzaldehyde, benzalkonium chloride, benzaprinoxide, benzarone, benzbromarone, benzestrol, benzethidine, benzethonium chloride, benzetimide, benzilonium bromide, benzindopyrine, benziodarone, benzmalecene, benznidazole, benzobarbital, benzocaine, benzoclidine, benzoctamide, benzodepa, benzododecinium chloride, benzoic acid, benzoin, benzonatate, benzopyrronium bromide, benzoquinium chloride, benzotript, benzoxiquine, benzoxonium chloride, benzoyl peroxide, benzoylpas, benzphetamine, benzpiperylon, benzpyrinium bromide, benzquercin, benzquinamide, benzthiazide, benztropine, benzydamine, benzylpenicillin, benzylsulfamide, beperidium iodide, bephenium naphtoate, bepiastine, bepridil, beraprost, berberine sulfate, bermastine, bermoprofen, berythromycin, besulpamide, beslunide, beta carotene, betacetylmethadol, betahistine, betaine, betameprodine, betamethadol, betamethasone acetate, betamethasone acibutate, betamethasone benzoate, betamethasone dipropionate, betamethasone phosphate, betamethasone valerate, betamicin, betaprodine, betazole, bethanechol chloride, bethanidine, betiatide, betoxycaine, bevantolol, bevonium metilsulfate, bezafibrate, bezitramide, bialamicol, bibenzonium bromide, bibrocathol, bicifadine, biclodil, biclofibrate, biclotymol, bicozamycin, bidimazium iodine, bietamiverine, bietaserpine, bifemelane, bifepramide, bifluranol, bifonazole, binedaline, binfloxacin, binfibrate, bioallethrin, bioresmethrin, biotin, bipenamol, biperiden, biphenamine, biriperone, bisacodyl, bisantrene, bis(aziridinyl) butanediol, bisbendazole, bisbentiamine, bisfenazone, bisfentidine, bismuth betanaphthol, bismuth-triglycollamate, bismuth subgallate, bismuth subsalicylate, bisorbin, bisoprolol, bisorcic, bioxatin acetate, bispyrithione magsulfex, bithionol, bithionoloxide, bitipazone, bitoterol, bitoscantate, bleomycin, bluensomycin, bofumustine, bolandiol dipropionate, bolasterone, bolazine, boldenone undecylenate, bolenol, bolmantalate, bometolol, bopindolol, bornaprine, bornaprolol, bornelone, botiacrine, boxidine, brallobarbital, brazergoline, brefonalol, bremazocine, brequinar, bretylium tosylate, brindoxime, brivundine, brobactam, broclepride, brocresine, brocrinat, brodimoprim, brofaromine, brofezil, brofoxine, brolaconazole, brolamfetamine, bromacrylide, bromadoline, bromamid, bromazepam, bromchlorenone, bromebric acid, bromerguride, brometenamine, bromfenac, bromhexine, bromindione, bromisovalum, bromociclen, bromocriptine, bromodiphenhydramine, bromofenofos, bromopride, bromoxandide, bromperidol, bromperidol decanoate, brompheniramine, bronopol, broparestrol, broperamole, bropirimine, broquinaldol, brosotamide, brosuximide, brotianide, brotizolam, brovanexine, brovincamine, broxaldine, broxaterol, broxitalamic acid, broxuridine, broxyquinoline, bruceantin, brucine, bucainide, bucetin, buciclovir, bucillamine, bucindolol, bucladesine, buclizine, buclosamide, bucloxic acid, bucolome, bucricaine, bucromarone, bucrylate, bucumolol, budesonide, budipine, budotitane, budralazine, bufenadrine, bufeniode, bufetolol, bufexamac, bufezolac, buflomedil, bufogenin, buformin, bufrolin, bufuralol, bumadizone, bumecaine, bumepidil, bumetanide, bumetrizole, bunaftine, bunamidine, bunamiodyl, bunaprolast, bunazosin, bunitrolol, bunolol, buparvaquone, bupicomide, bupivacaine, bupranolol, buprenorphine, bupropion, buquineran, buquinolate, buquiterine, buramate, burodiline, buspirone, busulfan, butabarbital, butacaine, butacetin, butaclamol, butadiazamide, butafosfan, butalamine, butalbital, butamben, butamirate, butamisole, butamoxane, butanediol cyclic sulfite, butanilicaine, butanixin, butanserin, butantrone, butaperazine, butaprost, butaverine, butedronate, buterizine, butetamate, butethamine, buthiazide, butibufen, butidrine, butikacin, butilfenin, butinazocine, butinoline, butirosin, butixirate, butobendine, butoconazole, butoprolol, butoctamide, butofilolol, butonate, butopamine, butopiprine, butoprozine, butopyrammonium iodide, butorphanol, butoxamine, butoxylate, butriptyline, butropium bromide, butylated hydroxyanisole, butylated hydroxytoluene, butylparaben, butynamine, and buzepide metiodide.

Also, cabastine, cabergoline, cadralazine, cafaminol, cafedrine, caffeine, calcifediol, calcitrol, calcium citrate, calcium dobesilate, calcium glubionate, calcium gluceptate, calcium gluconate, calcium glycerophosphate, calcium hypophosphite, calcium lactate, calcium lactobionate, calcium levulinate, calcium mandelate, calcium pantothenate, calcium phosphate dibasic, calcium phophate tribasic, calcium saccharate, calcium stearate, calusterone, camazepam, cambendazole, camiverine, camostast, camphotamide, camptothecin, camylofin, canbisol, cannabinol, canrenoic acid, canrenone, cantharidine, capobenic acid, capreomycin, caproxamine, capsaicin, captamine, captodiame, captopril, capuride, caracemide, caramiphen, carazolol, carbadox, carbaldrate, carbamazepine, carbamide peroxide, carbantel lauryl sulfate, carbaril, carbarsone, carbaspirin calcium, carbazeran, carbazochrome, carbazachrome salicylate, carbazachrome sulfonate, carbazocine, carbeniciltin, carbenicillin indanyl, carbencillin phenyl, carbenoxolone, carbenzide, carbestrol, carbetapentane, carbidopa, carbimazole, carbinoxamine, carbiphene, carbocloral, carbocysteine, carbofenotion, carbol-fuschin, carbomycin, carboplatin, carboprost, carboprost methyl, carboquone, carbromal, carbubarb, carburazepam, carbutamide, carbuterol, carcainium chloride, carebastine, carfentanil, carfimate, carisoprodol, carmantadine, carmetizide, carmofur, camidazole, carnitine, carocamide, caroverine, caroxazone, carperidine, caperone, carphenazine, carpindolol, carpiramine, carprofen, carpronium chloride, carsalam, cartazolate, carteolol, carubicin, carumonam, carvedilol, carzenide, carzolamide, cathine, cathinone, cefaloniurm, cefaloram, cefamandole naftate, cefaparole, cefatrizine, cefazaflur, cefazedone, cefazolin, cefbuperazone, cefcanel, cefcanel daloxate, cefedrolor, cefempidone, cefepime, cefetamet, cefetrizole, cefvitril, cefixime, cefmenoxime, cefmepidium chloride, cefmetazole, cefminox, cefodizime, cefonizid, cefotaxime, cefotetan, cefotiam, cefoxazole, cefpimizole, cefpiramide, cefpirome, cefpodoxime, cefpodoxime proxetil, cefquinome, cefrotil, cefroxadine, cefsulodin, cefsumide, ceftazidime, cefteram, ceftezole, ceftiofur, ceftiolene, ceftioxide, ceftizoxime, cefuracetime, cefuraxime axetil, cefurzonam, celiprolol, cephacetrile, cephaloglycin, cephaloridine, cephradine, cetaben, cetamolol, cethexonium chloride, cetiedil, cetirizine, cetocycline, cetohexazine, cetophenicol, cetotiamine, cetoxime, cetraxate, chaulmosulfone, chendiol, chiniofon, chlophedianol, chloracyzine, chloral betaine, chloral hydrate, chloralose, chlorambucil, chloramine, chloramphenicol palmitate, chloramphenicol succinate, chlorazanil, chlorbenzoxamine, chlorbetamide, chlorcyclizine, chlordantoin, chlordiazepoxide, chlordimorine, chlorhexadol, chlorhexidine, chlorhexidine phosphanilate, chlorindanol, chlorisondamine chloride, chlormadinone acetate, chlormerodrin, chlormezanone, chlormidazole, chloronaphazine, chloroazodin, chlorobutanol, chlorocresol, chlorodihydroxyandrostenone, chloroethyl mesylate, 5-chloro-3'-fluoro-2'3-dideoxyuridine, chloroguanide, chlorophenothane, chloroprednisone acetate, chloroprocaine, chloropyramine, chloroquine, chloroserpidine, chlorothen, chlorothiazide, chlorotriansene, chloroxine, chloroxylenol, chlorozotocin, chlorphenesin, chlorphenesin carbamate, chlorphenoctium amsonate, chlorphenoxamine, chlorphentermine, chlorproethazine, chlorproguanil, chlorpromazine, chlorpropamide, chlorprothixene, chlorquinaldol, chlortetracycline, chlorthalidone, chlorthenoxazine, chlorzoaxazone, chloecalciferol, cholic acid, choline chloride, choline glycerophosphate, chromocarb, chrornonar, ciadox, ciamexon, cianergoline, cianidol, cianopramine, ciapilome, cicaprost, cicarperone, ciclactate, ciclafrine, ciclazindol, cicletanine, ciclomenol, ciclonicate, ciclonium bromide, ciclopirox, ciclopramine, cicloprofen, cicloprolol, ciclosidomine, ciclotizolam, ciclotropium bromide, cicloxilic acid, cicloxolone, cicortonide, cicrotic acid, cidoxepin, cifenline, cifostodine, ciglitazone, ciheptolane, ciladopa, cilastatin, cilazapril, cilazaprilat, cilobamine, cilofungin, cilostamide, cilostazol, ciltoprazine, cimaterol, cimemoxin, cimepanol, cimetidine, cimetropium bromide, cimoxatone, cinchonine, cinchophen, cinecromen, cinepaxadil, cinepazet, cinepazic acid, cinepazide, cinfenine, cinfenoac, cinflumide, cingestol, cinitapride, cinmetacin, cinnamaverine, cinnamedrine, cinnarizine, cinnarizine clofibrate, cinnofuradione, cincotramide, cinodine, cinolazepam, cinoquidox, cinoaxin, cinoxate, cinoxolone, cinooxopazide, cinperene, cinprazole, cinpropazide, cinromide, cintazone, cintriamide, cinperone, ciprafamide, ciprafazone, ciprefadol, ciprocinonide, ciprofibrate, cipropride, ciproquazone, ciprostene, ciramadol, cirazoline, cisapride, cisconazole, cismadinone, cistinexine, citalopram, citatepine, citenamide, citenazone, citicoline, citiolone, clamidoxic acid, clamoxyquin, clanfenur, clanobutin, clantifen, clarithromycin, clavulanic acid, clazolam, clazolimine, clazuril, clebopride, clefamide, clemastine, clemeprol, clemizole, clenbuterol, clenpirin, cletoquine, clibucaine, clidafidine, clidanac, clidinum bromide, climazolam, climbazole, climiqualine, clindamycin, clindamycin palmitate, clindamycin phosphate, clinofibrate, clinolamide, cliquinol, clioxamide, clipoxamine, cliprofen, clobazam, clobenoside, clobenzepam, clobenzorex, clobentropine, clobetasol propionate, clobetasone butyrate, clobutinol, clobuzarit, clocanfamide, clocapramine, clociguanil, clocinizine, clocortolone acetate, clocortolone pivalate, clocoumarol, clodacaine, clodanolene, clodazon, clodoxopone, clodronic acid, clofazimine, clofenamic acid, clofenamide, clofenciclan, clofenetamine, clofenoxyde, clofenvinfos, clofeverine, clofexamide, clofezone, clofibrate, clofibric acid, clofibride, clofilium phosphate, cloflucarban, clofoctol, cloforex, clofurac, clogestone acetate, cloguanamil, clomacran, clomegestone acetate, clometacin, clometherone, clomethiazole, clometocillin, clomifenoxide, clominorex, clomiphene, clomipramine, clomocycline, clomoxir, clonazepam, clonazoline, clonidine, clonitazene, clonitrate, clonixeril, clonixin, clopamide, clopenthixol, cloperastine, cloperidone, clopidogrel, clopidol, clopimozide, clopipazan, clopirac, cloponone, cloprednol, cloprostenol, cloprothiazole, cloquinate, cloquinozine, cloracetadol, cloranolol, clorazepate, clorethate, clorexolone, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone propionate, clotioxone, clotrimazole, clovoxamine, cloxacepride, cloxacillin, cloxacillin benzathine, cloxazolam, cloxestradiol, cloximate, cloxotestosterone, cloxypendyl, cloxyquin, clozapine, cobamide, cocaine, cocarboxylase, codeine, codoxime, cofisatin, cogazocine, colchicine, colestolone, colfenamate, colforsin, colterol, conessine, conorphone, copper gluconate, cormethasone acetate, corticosterone, cortisone acetate, cortisuzol, cortivazol, cortodoxone, cotarnine chloride, cotinine, cotriptyline, coumaphos, coumazoline, coumermycin, coumetarol, creatinolfosfate, crisnatol, croconazole, cromakalim, cromitrile, cromolyn, cropropamide, crospovidone, crotamiton, crotetamide, crotoniazide, cruformate, cuprimyxin, cuproxoline, cyacetacide, cyamemazine, cyanocobalamine, cyclacillin, cyclandelate, cyclarbamate, cyclazocine, cyclazodone, cyclexanone, cyclindole, cycliramine, cyclizine, cyclobarbital, cyclobendazole, cyclobenzaprine, cyclobutoic acid, cyclobutyrol, cyclofenil, cycloguanil, cloheximide, cycloleucine, cyclomenol, cyclomethicone, cyclomethycaine, cyclopentamine, cyclopenthiazide, cyclopenazine, cyclophosphamide, cyclopregnol, cyclopyrronium bromide, cycloserine, cyclosporine, cyclothiazide, cyclovalone, cyclotiamine, cycrimine, cyheptamide, cyheptropine, cynarine, cypenamine, cypothrin, cyprazepam, cyprenophine, cyprodenate, cyproheptadine, cyprolidol, cyproquinate, cyproterone acetate, cyproximide, cystine, and cytarabine.

Also, dacarbazine, dacemazine, dacisteine, dacinomycin, dacuronium bromide, dagapamil, dalbraminol, daledalin, daltroban, dametralast, damotepine, danazol, danitracen, danosteine, danthron, dantrolene, dapiprazole, dapsone, daptomycin, darenzepine, darodipine, datelliptium chloride, dunorubicin, dazadrol, dazepinil, dazidamine, dazmegrel, dazolicine, dazopride, dazoquinast, dacoxiben, deanol aceglumate, deanol acetaminobenzoate, deazauridine, deboxamet, debrisoquin, decamethonium bromide, decimemide, decitropine, declaben, declenperone, decloxizine, decominol, decoquinate, deditonium bromide, deferoxamine, deflazacort, defosfamide, dehydroacetic acid, dehydroemetine, dehydro-7-methyltestosterone, delanterone, delapril, delergotrile, delfantrine, delmadinone acetate, delmetacin, delmopinol, delorazepam, deloxone, delprostenate, dembrexine, demeclocycline, demecolcine, demecycline, demegestone, demelverine, demexiptiline, democonazole, demoxepam, denaverine, denbufylline, denipride, denopamine, denpidazone, denzimol, deoxyspergualin, depramine, deprodone, deprostil, deptropine, derpanicate, desacetylcolchicine tartrate, desaspidin, desiclovir, descinolone acetonide, deserpidine, desipramine, deslanoside, desmethylcolchicine, desmethylmisonidazole, desmethylmoramide, desocriptine, desogestrel, desomorphine, desonide, desoximetasone, desoxycorticosterone acetate, desoxycorticosterone pivalate, desoxypyridoxine, detajmium bitartrate, detanosal, deterenol, detomidine, detorubicin, detrothronine, devapamil, dexamethasone, dexamethasone acefurate, dexamethasone acetate, dexamethasone dipropionate, dexamisole, dexbrompheniramine, dexchlorpheniramine, dexclamol, dexetimide, dexetozoline, dexfenfluramine, deximafen, dexindoprofen, dexivacaine, dexlofexidine, dexmedetomidine, dexoxadrol, dexpanthenol, dexpropranolol, dexproxibutene, dexecoverine, dextilidine, dextroamphetamine, dextrofemine, dextromethorphan, dextromoramide, dextrorphan, dextrothyroxine, dezaguanine, dezocine, diacerein, diacetamate, diacetolol, diacetylmorphine, diamfenetide, diaminomethylphenazinium chloride, diamocaine, diampromide, diamthazole, dianhydrogalactitol, diapamide, diarbarone, diathymosulfone, diatrizoic acid, diaveridine, diazepam, diaziquone, diazoacetylglycine hydrazide, diazouracil, diazoxide, dibekacin, dibemethine, dibenamine, dibenzepin, dibrompropamidine, dibromsalan, dibrospidium chloride, dibucaine, dibuprol, dibupyrone, dibusadol, dicarbine, dicarfen, dichlorallyl lawsone, dichlorisone acetate, dichlormezanone, dichlorofluormethane, dichlorom, ethotrexate, dichlorophen, dichlorophenarsine, dichlorotetrafluoroethane, dichloroxylenol, dichlorphenamide, dichlorvos, diciferron, dicirenone, diclazuril, diclofensine, diclofurime, diclometide, diclonixin, dicloxacillin, dicobalt edetate, dicolinium iodide, dicresulene, dicumarol, dicyclomine, didemnin, dideoxycytidine, didrovaltrate, dieldrin, dienestrol, dienogest, diethadione, diethazine, diethylpropion, diethylstilbestrol, diethylstilbestrol diphosphate, diethylstilbestrol dipropionate, diethylthiambutene, diethyltoluamide, dietifen, difebarbamate, difemerine, difemetorex, difenamizole, difencloxazine, difenoximide, difenoxin, difetarsone, difeterol, diflorasone diacetate, difloxacin, difluanine, diflucortolone, diflurcortolone pivalate, diflumidone, diflunisal, difluprednate, diftalone, digalloyl trioleate, digitoxin, digoxin, dihexyverine, dihydralazine, dihydroazacytidine, dihydroergotamine, dihydrolenperone, dihydrostreptomycin, dihydrotachysterol, dihydroxyfluoroprogestrone, diisopromine, diisopropanolamine, dilazep, dilevalol, dilmefone, diloxanide, diltiazem, dimabefylline, dimecamine, dimecolonium iodide, dimecrotic acid, dimefadane, dimefline, dimelazine, dimemorfan, dimenhydrinate, dimenoxadol, dimeheptanol, dimepranol, dimepregnen, dimeprozan, dimercaprol, dimesna, dimesone, dimetacrine, dimetamfetamine, dimethadione, dimethaminostyrylquinoline, dimethazan, dimethindene, dimethiodal, dimethisoquin, dimethisterone, dimetholizine, dimethoxanate, dimethylhydroxytestosterone, dimethylnorandrostadienone, dimethylnortestosterone, dimethylstilbestrol, dimethyl, dimethylthiambutene, dimethyltubocurarinium chloride, dimetipirium bromide, dimetofrine, dimetridazole, diminazene, dimoxamine, dimoxaprost, dimoxyline, dimpylate, dinaline, dinazafone, diniprofylline, dinitolmide, dinoprost, dinoprostone, dinsed, diosmin, dioxadilol, dioxadrol, dioxamate, dioxaphetyl butyrate, dioxethedrin, dioxifedrine, dioxybenzone, dipenine bromide, diperodon, diphemanil methylsulfate, diphenadione, diphenan, diphenhydramine, diphendiol, diphenoxylate, diphenylpraline, diphoxazide, dipipanone, dipipoverine, dipiverin, diprafenone, diprenorphine, diprobutine, diprofene, diprogulic acid, diproleandomycin, diproqualone, diproteverine, diprotriozate, diproxadol, dipyridamole, dipyrithione, dipyrocetyl, dipyrone, dirithromycin, disobutamide, disofenin, disogluside, disopyramide, disoxaril, distigmine bromide, disulergine, disulfamide, disulfuram, disuprazole, ditazole, ditercalinium chloride, dithiazanine iodide, ditiocarb, ditiomustine, ditolamide, ditophal, divabuterol, dixanthogen, dizatrifone, dizocilpine, dobupride, dobutamine, docarpamine, doconazole, docusate, doliracetam, domazoline, domiodol, domiphen bromide, domipizone, domoprednate, domoxin, domperidone, don, donetidine, dopamantine, dopamine, dopexamine, dopropidil, doqualast, dorastine, doreptide, dosergoside, dotarizine, dotefonium bromide, dothiepin, doxacurium chloride, doxaminol, doxapram, doxaprost, doxazosin, doxefazepam, doxenitoin, doxepin, doxibetasol, doxifluridine, doxofylline, doxorubicin, doxpicomine, doxylamine, dramedilol, draquinolol, deazidox, dribendazole, drindene, drobuline, drocinonide, droclidinium bromide, drocode, drofenine, droloxifene, drometrizole, dromostanolone, dromostanolone propionate, dronabinol, dropempine, droperidol, droprenilamine, dropropizine, drotaverine, drotebanol, droxacin, droxicamide, droxicam, droxidopa, droxypropine, dulofibrate, dulozafone, duometacin, duoperone, dupracetam, durapatite, dyclonine, dydrogesterone, dymanthine, and dyphylline.

Also, ebastine, ebrotidine, ebselen, ecastolol, echinomycin, echothiophate iodide, ecipramidil, eclanamine, eclazolast, econazole, ectylurea, edelfosine, edetic acid, edetol, edifolone, edogestrone, edoxudine, edrophonicum chloride, efaroxan, efetozole, eflornithine, efloxate, efrotomycin, elantrine, elanzepine, elderfield's pyrimidine mustard, elfazepam, ellagic acid, elliptinium acetate, elmustine, elnadipine, eltenac, eltoprazine, elucaine, elziverine, embramine, embutramide, emepronium bromide, emetine, emiglitate, emilium tosylate, emopanil, emorfazone, emylcamate, enalapril, enalaprilat, enbucrilate, encamide; enciprazine, enclomiphene, encyprate, endomide, endralazine, endrysone, enefexine, enestebol, enfenamic acid, enflurane, eniclobrate, enilconazole, enilospirone, enisoprost, enocitabine, enolicam, enoxacin, enoxamast, enoximone, enoxolone, eniprazole, eniproline, enprazepine, enprofylline, enpromate, enprostil, enrofloxacin, entsulfon sodium, enviomycin, enviradene, epalretat, epanolol, eperisone, ephedrine, epicamide, epicillin, epicriptine, epiestriol, epimestrol, epinastine, epinephryl borate, epipropidine, epirizole, epiroprim, epirubicin, epithiazide, epitiostanol, epoprostenol, epostane, eprazinone, eprovafen, eproxindine, eprozinol, epsiprantel, eptaloprost, eptazocine, equilin, erdosteine, ergocalciferol, ergoloid mesylates, ergonovine, ergosterol, ergotamine, ericolol, erizepine, erocamide, erythrityl tetranitrate, erythromycin acistrate, erythromycin ethylsuccinate, erythromycin propionate, erythrosine, esaprazole, esculamine, eseridine, esflurbiprofen, esmolol, esorubicin, esproquin, estazolam, estradiol benzoate, estradiol cypionate, estradiol dipropionate, estradiol enanthate, estradiol undecylate, estradiol valerate, estramustine, estramustine phosphate, estrapronicate, estrazinol, estriol, estrofurate, estrone, estrone hydrogen sulfate, estropipate, esuprone, etabenzarone, etacepride, etafedrine, etafenone, etamestrol, etamiline, etamiphyllin, etamocycline, etanidazole, etanterol, etaqualone, etasuline, etazepine, etazolate, etebenecid, eterobarb, etersalate, ethacridine, ethacrynic acid, ethambutol, ethamivan, ethamsylate, ethanolamine oleate, ethaverine, ethchlorvynol, ethenzamide, ethazide, ethidium chloride, ethinamate, ethinyl estradiol, ethiofos, ethionamide, ethsterone, ethoheptazine, ethomoxane, ethonam, ethopropazine, ethosuximide, ethotoin, ethoxazene, ethoxazorutoside, ethoxzolamide, ethyybenztropine, ethyl biscoumacetate, ethyl carfluzepate, ethyl cartrizoate, ethyl dibunate, ethyl dirazepate, ethylenediamine, ethylestrenol, ethylhydrocupreine, ethyl loflazepate, ethylmethylthiambutene, ethylmorphine, 9-ethyl-6-mercaptopurine, ethyl nitrite, ethylnorepinephrine, ethylparaben, ethylphenacemide, ethylstibamine, ethynerone, ethynodiol diacetate, ethypicone, etibendazole, eticlopride, eticyclidine, etidocaine, etidronic acid, etifelmine, etifenin, etifoxine, etilamfetamine, etilefrine, etilefrine pivalate, etintidine, etiochlanolone, etipirium iodide, etiproston, etiracetam, etiroxate, etisazole, etisomicin, etisulergine, etizolam, etocarlide, etocrylene, etodolac, etodroxine, etofamide, etofenamate, etofenprox, etofibrate, etoformin, etofuradine, etofylline, etoglucid, etolorex, etolotifen, etoloxamine, etomidate, etomidoline, etomoxir, etonitazene, etoperidone, etoposide, etoprindole, etoprine, etorphine, etosalamide, etoxadrol, etoxeridine, etozolin, etrabamine, etretinate, etryptamine, etymemazine, eucalyptol, eugenol, euprocin, evandamine, Evans blue, exalamide, exametazine, exaprolol, exepanol, exifone, and exiproben.

Also, falintolol, falipamil, famiraprinium chloride, famotidine, famotine, famiprofazone, fanetizole, fantridone, fazadinium bromide, fazaribine, febantel, febarbamate, februprol, febuverine, feclemine, feclobuzone, fedrilate, felbamate, felbinac, felipyrine, felodipine, femoxetine, fenabutene, fenacetinol, fenaclon, fenadiazole, fenaptic acid, fenalamide, fenalcomine, fenamifuril, penamole, fenaperone, fenbendazole, fenbencillin, fenbufen, fenbutrazate, fencamfamine, fencibutirol, fenclexonium metilsulfate, fenclofenac, fenclonine, fenclorac, fenlozic acid, fendiline, fendosal, feneritrol, fenestrel, fenethazine, fenethylline, fenetradil, fenflumizole, fenfluramine, fenfluthrin, fengabine, fenharmane, fenimide, feniodium chloride, fenipentol, fenirofibrate, fenisorex, fenmetozole, fenmetramide, fenobam, fenocinol, fenoctimine, fenofibrate, fenoldopam, fenoprofen, fenoterol, fenoverine, fenoxazoline, fenoxedil, fenozolone, fenpentadiol, fenperate, fenipalone, fenipramide, fenprane, fenpiverinium bromide, fenprinast, fenproporex, fenprostalene, fenquizone, fenretinide, fenspiride, fentanyl, fentiazac, fenticlor, fenticonazole, fentonium bromide, fenyripol, fepentolic acid, fepitrizol, fepradinol, feprazone, fepromide, feprosidnine, ferriclate calcium, ferrotrenine, ferrous fumarate, ferrous gluconate, fetoxylate, fexicaine, fexinidazole, fezatione, fezolamine, fiacitabine, fibracillin, filenadol, filipin, fifexide, flamenol, flavamine, flavodic acid, flavodil, flavoneactic acid, flavoxate, flazalone, flecamide, flerobuterol, fleroxacin, flesinoxan, flestolol, fletazepam, floctafenine, flomoxef, flopropione, florantyrone, flordipine, floredil, florfenicol, florifenine, flosequinan, flotrenizine, floverine, floxacillin, floxacrine, floxuridine, fluacizine, flualamide, fluanisone, fluazacort, flubanilate, flubendazole, flubepride, flucabril, flucetorex, flucindole, fluciprazine, flucloronide, fluconazole, flucrylate, flucytosine, fludalanine, fludarabine phosphate, fludazonium chloride, fludiazepam, fludorex, fludoxopone, fludrocortisone acetate, flufenamic acid, flufenisal, flufosal, flufylline, fluindarol, fluindione, flumazenil, flumecinol, flumedroxone-17-acetate, flumequine, flumeridone, flumethasone, flumethasone pivalate, flumethiazide, flumetramide, flumexadol, flumezapine, fluminorex, flumizole, flumoxonide, flunamine, flunarizine, flunidazole, flunisolide, flunisolide acetate, flunitrazepan, flunixin, flunoprost, flunoxaprofen, fluocinolone acetonide, fluocinonide, flourcortin butyrate, fluocortolone, fluocortolone caproate, fluorescein, fluoresone, fluoroadenosine, 3-fluoroandrostanol, fluorodopane, fluorohydroxyandrosterone, fluorometholone acetate, fluorosalan, 6-fluorotestosterone propionate, 9-fluoroxotestenololactone, 9-fluoroxotestololacetone, fluotracen, fluqxetine, fluoxymesterone, fluparoxan, flupentixol, fluperamide, fluperlapine, fluperolone acetate, fluphenazine, fluphenazine enanthate, flupimazine, flupirtine, flupranone, fluprazine, fluprednidene, fluprednisolone, fluprednisolone valerate, fluprofen, fluprofylline, fluproquazone, fluprostenol, fluquazone, fluradoline, flurandrenoline, flurantel, flurazepam, flurbiprofen, fluretofen, flurithromycin, fluorocitabine, fluorofamide, fluorogestone acetate, fluorothyl, fluoroxene, flusoxolol, fluspiperone, fluspirilene, flutamide, flutazolam, flutemazepam, flutiazin, fluticasone propionate, flutizenol, flutonidine, flutoprazepam, flutroline, flutropiurn bromide, fluvoxamine, fluzinamide, fluzoperine, folescutol, folic acid, fomidacillin, fominoben, fomocaine, fonazine, fopirtoline, forfenimex, formebolone, formetorex, formintrazole, formocortal, formoterol, fosarilate, fosazepam, foscarnet, foscolic acid, fosenazide, fosfocreatine, fosfomycin, fosfonet, fosfosal, fosinapril, fosmenic acid, fosmidomycin, forpirate, fostedil, fostriecin, fotemustine, fotreamine, frabuprofen, frentizole, fronepidil, froxiprost, ftaxilide, ftivazide, ftorafur, ftormetazine, ftorpropazine, fubrogonium iodide, fuchsin, fumagillin, fumoxcillin, fuprazole, furacrinic acid, furafylline, furalazine, furaltadone, furaprofen, furazabol, furazolidone, furazolium chloride, furbucillin, furcloprofen, furegrelate, furethidine, furfenorex, furidarone, furmethoxadone, furobufen, furodazole, furofenac, furomazine, furosemide, furostilbestrol, fursalan, fursultiamine, furtherene, furtrethonium iodide, fusidic acid, and fuzlocillin.

Also, gabapentin, gabexate, gaboxadol, galantamine, gallamine triethodide, gallopamil, galosemide, galtifenin, gampexine, gamolenic acid, ganglefene, gapicomine, gapromidine, gefarnate, gemazocine, gemcadiol, gemeprost, gemfibrozil, gentian violet, gepefrine, gepirone, geroquinol, gestaclone, gestadienol, gestodene, gestonorone caproate, gestrinone, giparmen, gitaloxin, gitoformate, glafenine, glaziovine, gliamilide, glibomuride, glibutimine, glicaramide, glicetanile, geroquinol, gestaclone, gestadienol, gestodene, gestonorone caproate, gestrinone, giparmen, gitaloxin, gitoformate, glafenine, glaziovine, gliamilide, glibomuride, glibutimine, glicaramide, glicetanile, gliclazide, glicondamide, glidazamide, gliflumide, glimepiride, glipentide, glipizide, gliquidone, glisamuride, glisindamide, glisolamide, glisoxepide, gloxazone, gloximonam, glucametacin, glucosamine, glucosulfamide, glucosulfone, glucurolactone, glucuronamide, glunicate, glutamic acid, glutaral, glutarimide, glutaurine, glutethimide, glyburide, glybuthiazol, glybuzole, glyceryl monostearate, glycidyl methacrylate, glycine, glyclopyramide, glybiarsol, glycopyrrolate, glycyclamide, glyhexamide, glymidine, glyoctamide, glypinamide, glyprothiazol, glysobuzole, gold thiomalate, gold sodium thiosulfate, granisetron, griseofulvin, guabenxan, guacetisal, guafecainol, guaiactamine, guaiapate, guaietolin, guaifenesin, guaimesal, guaisteine, guaithylline, guamecycline, guanabenz, guanacline, guanadrel, guanazodine, guanazole, guanclofine, guancydine, guanethidine, guanfacine, guanisoquin, guanoclor, guanoctine, guanoxabenz, guanoxan, and guanoxyfen.

Also, hadacidin, halazepam, halazone, halcinonide, halethazole, halocortolone, halofantrine, halofenate, halofuginone, halometasone, halonamine, halopemide, halopenium chloride, haloperidol, haloperidol decanoate, haloperidone acetate, haloprogesterone, haloprogin, halothane, haloxazolam, haloxon, halquinols, hedaquinium chloride, hepronicate, heptabarbital, heptaminol, heptaverine, heptolamide, hepzidine, hetacillin, hetaflur, heteronium bromide, hexachlorophene, hexacyclonate, hexacyprone, hexadiline, hexadimethrine bromide, hexafluorenium bromide, hexamethonium bromide, hexamidine, hexapradol, hexaprofen, hexapropymate, hexasonium iodide, hexacarbacholine bromide, hexedine, hexestrol, hexetidine, hexobarbital, hexobendine, hexocyclium methylsulfate, hexoprenaline, hexopyrronium bromide, hexylcaine, hexylene glycol, hexylresorcinol, histamine, histapyrrodine, homarylamine, homatropine methylbromide, homidium bromide, homochlorcyclizine, homofenazine, homoharringtonine, homopipramol, homosalate, homotestosterone propionate, homprenorphine, hopantenic acid, hoquizil, hycanthone, hydracarbazine, hydrargaphen, hydrobentizide, hydrochlorthiazide, hydrocodone, hydrocortamate, hydrocortisone aceponate, hydrocortisone butyrate, hydrocortisone cypionate, hydrocortisone-phosphate, hydrocortisone succinate, hydrocortisone valerate, hydroflumethiazide, hydromadinone, hydromorphinol, hydromorphone, hydroquinone, hydroxindasate, hydroxindasol, hydroxyoxocobalamin, hydroxychloroquine, hydroxydimethandrostadienone, hydroxydione succinate, hydroxymethylandrostanone, 10-hydroxynorehisterone, hydroxypethidine, hydroxyphenamate, hydroxyprocaine, hydroxyprogeserone, hydroxyprogesterone caproate, hydroxypyridine tartrate, hydroxystilbamidine, 7-hydroxytestololacetone, hydroxytestosterone propionate, hydroxytetracaine, hydroxytoluic acid, hydroxyurea, hydroxyzine, hymecromone, hyoscyamine, and hypericin.

Also, ibacitabine, ibafloxacin, ibazocine, ibopamine, ibrotamide, ibudilast, ibufenac, ibuprofen piconol, ibuproxam, ibuterol, ibuverine, icazepam, icosipiramide, icotidine, idarubicin, idaverine, idazoxan, idebenone, idenast, idralfidine, idrocilamide, idropranolol, ifenprodil, ifosfamide, ifoxetine, ilmofosine, iloprost, imafen, imanixil, imazodan, imcarbofos, imexon, imiclopazine, imidazole salicylate, imidazopyrazole, imidecyl iodine, imidocarb, imidoline, imidurea, imiloxan, iminophendimide, imipenem, imipramine, imipraminoxide, imirestat, imolamine, imoxiterol, impacarzine, impromidine, improsulfan, imuracetam, inaperisone, indacrinone, indalpine, indanazoline, indanidine, indanorex, indapamide, indatraline, indacamide, indeloxazine, indenolol, indicine-N-oxide, indigotindisulfonic acid, indobufen, indocate, indocyanine green, indolapril, indolidan, indopanolol, indopine, indoprofen, indoramin, indorenate, indoxole, indriline, inicarone, inocoterone, inosine, inosine dialdehyde, inositol niacinate, inproquone, intrazole, intriptyline, iobenzamic acid, iobutic acid, iocarmic acid, iocetamic acid, iodamide, iodecimol, iodetryl, iodipamide, iodixanol, iodoalphionic acid, iodol, iodophthalein, iodoquinol, iodothiouracil, iodoxamic acid, ioglicic acid, ioglucol, ioglucomide, ioglunide, ioglycamic acid, iogulamide, iohexyl, iodlidonic acid, iolixanic acid, iomeglamic acid, iomeprol, iomorinic acid, iopamidol, iopanoic acid, iopentol, iophendylate, iophenoxic acid, ioprocemic acid, iopromide, iopronic acid, iopydol, iopydone, iosarcol, iosefamic acid, ioseric acid, iosimide, iosulamide, iosumetic acid, iotasul, iotetric acid, iothalamic acid, iotranic acid, iotrizoic acid, iotrolan, iotroxic acid, ioversol, ioxabrolic acid, ioxaglic acid, ioxitalamic acid, ioxotrizoic acid, iozomic acid, ipexidine, ipodic acid, ipragratine, ipramidil, ipratropium bromide, iprazochrome, ipriflavone, iprindole, iprocinodine, iproclozide, iprocrolol, iprofenin, iproheptine, iproniazid, iproidazole, iproplatin, iprotiazem, iproxamine, iprozilamine, ipsalazide, ipsapirone, iquindamine, irindalone, irloxacin, irolapride, irsogladine, isamfazone, isamoltan, isamoxole, isaxonine, isbogrel, isepamicin, isoaminile, isobromindione, isobucaine, isobutamben, isocarboxazid, isoconazole, isocromil, isoetharine, isofezolac, isoflupredone acetate, isoflurane, isofluorophate, isoleucine, isomazole, isomerol, isometamidium, isomethadone, isometheptene, isomylamine, isoniazid, isonixin, isoprazone, isoprednidene, isoprofen, isoprofamide iodide, isopropicillin, isopropyl myristate, isopropyl palmitate, isoproterenol, isosorbide, isosorbide dinitrate, isosorbide mononitrate, isospalglumic acid, isosulfan blue, isosulpride, isothipendyl, isotic, isotiquimide, isotretinoin, isoxaprolol, isoxepac, isoxicam, isoxsuprine, isradipine, itanoxone, itazigrel, itraconazole, itrocamide, ivermectin bib, and ivoqualine.

Also, josamycin.

Also, kainic acid, kalafungin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, and kitasamycin.

Also, labetalol, lacidipine, lactalfate, lactose, lactulose, lamotrigine, lamtidine, lanatoside, lapachol, lapinone, lapyrium chloride, lasalocid, laudexium methyl sulfate, lauralkonium chloride, laureth, laurixamine, laurocapram, lauroguadine, laurolinium acetate, lauryl isoquinolinium, lefetamine, leflunomide, leiopyrrole, lemidosul, lenampicillin, leniquinsin, lenperone, leptacline, lergotrile, letimide, letosteine, leucine, leucinocaine, leucocianidol, leucovorin, levacecamine, levallorphan, levamfetamine, levamisole, levdropropizine, levisoprenaline, levlofexidine, levocabastine, levocarnitine, levodopa, levofacetoperane, levofenfluramine, levofuraltadone, levoglutamide, levomenol, levomethadone, levomethadyl acetate, levomethorphan, levometiomeprazine, levomopranol, levomoramide, levonantradol, levonordeprin, levonorgestrel, levophenacyl morphan, levopropoxyphene, levopropylcillin, levopropylhexedrine, levoprotiline, levorin, levorphanol, levothyroxine, levoxadrol, lexofenac, libecillide, libenzapril, lidamidine, lidocaine, lidofenin, lidoflazine, lifibrate, lilopristone, limaprost, lincomycin, lindane, linsidomine, iothyronine, liroldine, lisinopril, lisuride, lithium carbonate, lithium citrate, litracen, lividomycin, lixazinone, lobeline, lobendazole, lobenzarit, lobuprofen, locicortone, lodaxaprine, lodacezarlodinixil, lodiperone, lodoxamide, lodoxamide ethyl, lofemizole, lofendazam, lofentanil, lofepramine, lofexidine, loflucarban, lombazole, lomefloxacin, lometraline, lomevactone, lomifylline, lomofungin, lomustine, lonapalene, lonaprofen, lonazolac, lonidamine, loperamide, loperamide oxide, lopirazepam, loprazolam, loprodiol, lorajmine, lorapride, loratadine, lorazepam, lorbamate, lorcainide, lorcinadol, lorglumide, lormetazepam, lortalamine, lorzafone, losindole, losulazine, lotifazole, lotrifen, lotucaine, lovastatin, loxanast, loxapine, loxiglumide, loxoprofen, loxtidine, lozilurea, lucanthone, lucartamide, lucimycin, lufuradom, lupitidine, luprostiol, luxabendazole, lyapolate sodium, lycetamine, lydimycin, lymecycline, lynestrenol, lysergide, and lysine.

Also, mabuterol, maduramicin, mafenide, mafoprazine, mafosfamide, magnesium citrate, magnesium gluconate, magnesium salicylate, malathion, malethamer, malic acid, malotilate, manidipine, manganese gluconate, mannitol, mannitol hexanitrate, mannomustine, mannosulfan, manozodil, maprotiline, maridomycin, mariptiline, maroxepin, maytansine, mazaticol, mazindol, mazipredone, mebanazine, mebendazole, mebenoside, mebeverine, mebezonium iodide, mebhydrolin, mebiquine, mebolazine, mebrofenin, mebutamate, mebutizide, mecamylamine, mecarbinate, mecetronium ethylsulfate, mechlorethamine, meciadanol, mecinarone, meclizine, meclocycline, meclocycline sulfosalicylate, meclofenamic acid, meclofenoxate, meclonazepam, mecloqualone, mecloralurea, meclorisone dibutyrate, mecloxamine, mecobalamin, mecrylate, mecysteine, medazepam, medazomide, medetomidine, medibazine, medifoxamine, medorinone, medorubicin, medrogestone, medronic acid, medroxalol, medroxyprogesterone, medroxyprogesterone acetate, medrylamine, mefeclorazine, mefenamic acid, mefenidil, mefenidramium metilsulfate, mefenorex, mefeserpine, mefexamide, mefloquine, mefruside, megalomicin, megestrol acetate, meglitinide, megucycline, meglumine, meglutol, meladrazine, melarsonyl, melarsoprol, melengestrol acetate, meletimide, melinamide, melitracen, melizame, meloxicam, melperone, melphalan, memantine, memotine, menabitan, menadiol, menadiol diphosphate, menadiol disulfate, menadione, menadione sodium bisulfite, menatetrenone, menbutone; menfegol, menglytate, menitrazepam, menoctone, menogaril, menthol, meobentine, meparfynol, mepazine, mepenzolate bromide, meperidine, mephenesin, mephenoxalone, mephentermine, mephenylon, mephobarbital, mepindolol, mepiprazole, mepiroxol, mepitiostane, mepivacaine, mepixanox, mepramidil, meprednisone, meprobamate, meproscillarin, meproxitol, meprylcaine, meptazinol, mequidox, mequinol, mequitazine, meralein, meralluride, merbarone, merbromin, mercaptamine, mercaptomerin, mercaptopurine, mercuderamide, mercufenol chloride, mercumatilin, mercurobutol, mergocriptine, merophan, mersalyl, mesabolone, mesalamine, meseclazone, mesna, mesocarb, meso-hexestrol, mesoridazine, mesipirenone, mestanolone, mesterolone, mestranol, mesudipine, mesulergine, mesulfamide, mesulfen, mesuprine; metabromsalan, metacetamol, metaclazepam, metaglycodol, metahexamide, metamelfalan, metamfazone, metamfepramone, metampicillin, metanixin, metapramine, metaproterenol, metaraminol, metaterol, metaxalone, metazamide, metazide, metazocine, metbufen, meteneprost, metergoline, metergotamine, metescufylline, metesculetol, metethoheptazine, metformin, methacholine chloride, methacycline, methadone, methadyl acetate, methallenestril, methallibure, methalthiazide, methamphetamine, methandriol, methandrostenolone, methaniazide, methantheline bromide, methaphenilene, methaqualone, metharbital, methastyridone, methdilazine, methenamine, methenolone acetate, methenolone enanthate, metheptazine, methestrol, methetoin, methicillin, methimazole, methiodal sodium, methioguanine, methiomeprazine, methionine, methisazone, methitural, methixene, methocarbamol, methohexital, methopholine, methoserpidine, methotrexate, methotrimeprazine, methoxamine, methoxsalen, methoxyflurane, methoxyphedrine, methoxyphenamine, methoxypromazine, methscopolamine bromide, methsuximide, methyllothiazide, N-methyladrealone hcl, methyl alcohol, methylatropine nitrate, methylbenactyzium bromide, methylbenzethonium, methylchromone, methyldesorphine, methyldihydromorphine, methyldopa, methyldopate, methylene blue, methylphedrine, methylergonovine, methylformamide, methyl nicotinate, 2-methyl-19-nortestosterone, 2-methyl-11-oxoprogestrone, methyl palmoxirate, methylparaben, methylphendiate, methylprednisolone aceponate, methylprednisolone acetate, methylprednisolone hemisuccinate, methylprednisolone phosphate, methylprednisolone suleptanate, methyl salicylate, methylstreptonigrin, 4-methyltestosterone, 7-methyltestosterone, 17-methyltestosterone, 7-methyltesosterone propionate, methylthionosine, 16-methylthioprogestone, methylthiouracil, methynodiol diacetate, methyprylon, methysergide, metiamide, metiapine, metiazinic acid, metibride, meticrane, metildigoxin, metindizate, metioprim, metioxate, metipirox, metipranolol, metiprenaline, metitepine, metizoline, metkephamid, metochalcone, metocinium iodide, metoclopramide, metocurine iodide; metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoic acid, metronidazole, meturedepa, metyrapone, metyridine, metyrosine, mevastatin, mexafylline, mexazolam, mexenone, mexiletine, mexiprostil, mexoprofen, mexrenoate, mezacopride, mezepine, mezilamine, mezlocillin, mianserin, mibolerone, micinicate, micronomicin, midaflur, midaglizole, midalcipran, midamaline, midazogrel, midazolam, midecamycin, midodrine, mifentidine, mifepristone, mifobate, miglitol, mikamycin, milacemide, milenperone, milipertine, miloxacin, milrinone, milverine, mimbane, minaprine, minaxolone, mindolilol, mindoperone, minepentate, minocromil, minoxidil, mioflazine, mipimazole, mirincamycin, miristalkonium chloride, miroprofen, mirosamicin, misonidazole, misoprostol, mitindomide, mitobronitol, mitoclomine, mitoguazone, mitolactol, mitomycin, mitonafide, mitopodozide, mitoquidone, mitotane, mitotenamine, mitoxantrone, mitozolomide, mivacurium chloride, mixidine, misoprostol, mitindomide, mitobronitol, mitoclomine, mitoguazone, mitolactol, mitomycin, mitonafide, mitopodozide, mitoquidone, mitotane, mitotenamine, mitoxantrone, mitozolomide, mivacurium chloride, mixidine, mizoribine, mobecarb, mob enzoxamine, mocimycin, mociprazine, moclobemide, moctamide, modafinil, modaline, mofebutazone, mofloverine, mofoxime, molfarnate, molinazone, molindone, molracetam, molsidomine, mometasone furoate, monalazone disodium, monensin, monobenzone, monoethanolamine, monometacrine, monophosphothiamine, monothioglycerol, monoxerutin, montirelin, moperone, mopidamol, mopidralazine, moprolol, moquizone, morantel, morazone, morclofone, morforex, moricizine, morinamide, morniflumate, morocromen, moroxydine, morpheridine, morphine, morsuximide, motapizone, motrazepam, motretinide, moveltipril, moxadolen, moxaprindine, moxastine, moxaverine, moxazocine, moxestrol, moxicoumone, moxipraquine, moxisylyte, moxnidazole, moxonidine, mupirocin, murabutide, murocamide, muzolimine, mycophenolic acid, myfadol, myralact, myrophine, and myrtecaine.

Also, nabazenil, nabilone, nabitan, naboctate, nabumetone, nadide, nadolol, nadoxolol, naepaine, nafamostat, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypramide, nalbuphine, nalidixic acid, nalmefene, nalmexone, nalorphine, naltrexone, naminterol, namoxyrate, nanaprocin, nandrolone cyclotate, nandrolone decanoate, nandrolone phenpropionate, nanofin, nantradol, napactadine, napamezole, naphthonone, naprodoxime, naproxen, naproxol, naranol, narasin, natamycin, naxagolide, naxaprostene, nealbarbital, nebidrazine, nebivolol, nebracetam, nedocromil, nefazodone, neflumozide, nefopam, nelezaprine, neoarsphenamine, neocinchophen, nequinate, neraminol, nerbacadol, nesapidil, nesosteine, netilmicin, netobimin, neutramycin, nexeridine, niacin, niacinamide, nialamide, niaprazine, nibroxane, nicafenine, nicainoprol, nicametate, nicarbazin, nicarpidine, nicergoline, niceritrol, niceverine, niclofolan, niclosamide, nicoboxil, nicoclonate, nicocodine, nicocortonide, nicodicodine, nicofibrate, nicofuranose, nicofurate, nicogrelate, nicomol, nicomorphine, nicopholine, nicorandil, nicothiazone, nicotinyl alcohol, nicoxamat, nictiazem, nictindole, nodroxyzone, nifedipine, nifenalol, nifenazone, niflumic acid, nifluridide, nifuradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifurprazine, nifurquinazole, nifusemizone, nifursol, nifurthiazole, nifurtimox, nifurtoinol, nifurvidine, nifurzide, niguldipine, nihydrazone, nikethamide, nileprost, nilprazole, niludipine, nilutamide, nilvadipine, nimazone, nimesulide, nimetazepam, nimidane, nimodipine, nimorazole, nimustine, niometacin, niperotidine, nipradilol, niprofazone, niridazole, nisbuterol, nisobamate, nisoldipine, nisoxetine, nisterime acetate, nitarsone, nitazoxanide, nithiamide, nitracrine, nitrafudam, nitralamine, nitramisole, nitraquazone, nitrazepam, nitrefazole, nitrendipine, nitricholine, nitrochlofene, nitrocycline, nitrodan, nitrofurantoin, nitroglycerin, nitromersol, nitromide, nitromifene, nitroscanate, nitrosulfathiazole, nitroxinil, nitroxoline, nivazol, nivimeldone, nixylic acid, nizatidine, nizofenone, noberastine, nocloprost, nocodazole, nofecamide, nogalamycin, nolinium bromide, nomegestrol, nomelidine, nomifensine, nonabine, nonaperone, nonapyrimine, nonoxynol-4, nonoxynol-9, noracymethadol, norbolethone, norbudrine, norclostebol, norcodeine, nordazepam, nordefrin, nordinone, norepinephrine, norethandrolone, norethindrone, norethindrone acetate, norethynodrel, noreximide, norfenefrine, norfloxacin, norfloxacin succinil, norflurane, norgesterone, norgestimate, norgestomet, norgestrel, norgestrienone, norletimol, norlevorphanol, normethadone, normethandrone, normorphine, norpipanone, nortestosterone propionate, nortetrazepam, nortriptyline, norvinisterone, nosantine, noscapine, nosiheptide, novobiocin, noxiptiline, noxytiolin, nuclomedone, nuclotixine, nufenoxole, nuvenzepine, nylestriol, nylidrin, and nystatin.

Also, obidoxime, ociltide, ocrylate, octabenzone, octacaine, octafonium chloride, octamoxin, octamylamine, octanoic acid, octapinol, octastine, octaverine, octazamide, octenidine, octenidine saccharin, octicizer, octimibate, octorylene, octodrine, octopamine, octotiamine, octoxynol-9, octriptyline, octrizole, ofloxacin, oformine, oftasceine, olaflur, olaquindox, oleanomycin, oletimol, oleyl alcohol, olivomycin a, olmidine, olpimedone, olsalazine, oltipraz, olvanil, omeprazole, omidoline, omoconazole, omonasteine, onapristone, ondansetron, ontianil, opiniazide, opipramol, orazamide, orbutopril, orconazole, orestrate, ormetoprim, ornidazole, ornipressin, ornithine, omoprostil, orotic acid, orotirelin, orpanoxin, orphenadrine, ortetamine, osalmid, osmadizone, otilonium bromide, otimerate sodium, ouabain, oxabolone cipionate, oxabrexine, oxaceprol, oxacillin, oxadimedine, oxaflozane, oxaflumazine, oxagrelate, oxalinast, oxaliplatin, oxamarin, oxametacin, oxamisole, oxamniquine, oxanamide, oxandrolone, oxantel, oxapadol, oxapium iodide, oxapropanium iodide, oxaprotiline, oxaprozin, oxarbazole, oxatomide, oxazafone, oxazepam, oxazidione, oxazolam, oxazorone, oxcarbazepine, oxdralazine, oxeladin, oxendolone, oxepinac, oxetacillin, oxethazaine, oxetorone, oxfendazole, oxfenicine, oxibendazole, oxibetaine, oxiconazole, oxidopamine, oxidronic acid, oxifentorex, oxifungin, oxilorphan, oximonam, oxindanac, oxiniacic acid, oxiperomide, oxiracetam, oxiramide, oxisopred, oxisuran, oxitefonium bromide, oxitriptan, oxitriptyline, oxitropium bromide, oxmetidine, oxodipine, oxogestone phenpropionate, oxolamine, oxolinic acid, oxomemazine, oxonazine, oxophenarsine, oxoprostol, oxpheneridine, oxprenoate potassium, oxprenolol, oxtriphylline, oxybenzone, oxybutynin, oxychlorosene, oxycinchophen, oxyclozanide, oxycodone, oxydipentonium chloride, oxyfedrine, oxymesterone, oxymetazoline, oxymetholone, oxymorphone, oxypendyl, oxypertine, oxyphenbutazone, oxyphenonium bromide, oxypurinol, oxypyrronium bromide, oxyquinoline, oxyridazine, oxysonium iodide, oxytiocin, ozagrel, and ozolinone.

Also, pacrinolol, pactamycin, padimate, pafenolol, palatrigine, paldimycin, palmidrol, palmoxiric acid, pamabrom, pamaquine, pamatolol, pamidronic acid, pancuronium bromide, panidazole, panomifene, patenicate, panthenol, pantothenic acid, panuramine, papaverine, papaveroline, parachlorophenol, paraflutizide, paraldehyde, paramethadione, paramethasone acetate, paranyline, parapenzolate bromide, parapropamol, pararosaniline, pararosaniline embonate, paraxazone, parbendazole, parconazole, pareptide, parethoxycaine, pargeverine, pargolol, pargyline, paridocaine, parodilol, paromomycin, paroxetine, paroxypropione, parsalmide, partricin, parvaquone, pasiniazid, paulomycin, paxamate, pazelliptine, pazoxide, pcnu, pecilocin, pecocycline, pefloxacin, pelanserin, pelretin, pelrinone, pemedolac, pemerid, pemoline, pempidine, penamecillin, penbutolol, pendecamaine, penfluridol, penflutizide, pengitoxin, penicillamine, procaine, penicillin, penimepicycline, penimocycline, penirolol, penmesterol, penoctonium bromide, penprostene, pentabamate, pentacynium chloride, pentaerythritol tetranitrate, pentafluranol, pentagastrin, pentagestrone, pentalamide, pentamethonium bromide, pentamethylmelamine, pentamidine, pentamoxane, pentamustine, pentapiperide, pentapiperium methylsulfate, pentaquine, pentazocine, pentetate calcium trisodium, pentetic acid, penthienate bromide, penthrichloral, pentiapine maleate, pentifylline, pentigetide, pentisomicin, pentisomide, pentizidone, pentobarbital, pentolinium tartrate, pentomone, pentopril, pentorex, pentosan polysulfate sodium, pentostatin, pentoxifylline, pentrinitrol, pentylenetrazole, peplomycin, pepstatin, peraclopone, peradoxime, perafensine, peralopride, peraquinsin, perastine, peratizole, perbufylline, perfluamine, perflunafene, pergolide, perhexylene, periciazine, perimetazine, perindopril, perindoprilat, perisoxal, perlapine, permethrin, perphenazine, persilic acid, petrichloral, pexantel, phanquone, phenacaine, phenacemide, phenacetin, phenacttropinium chloride, phenadoxone, phenaglycodol, phenamazoline, phenampromide, phenarsone sulfoxylate, phenazocine, phenazopyridine, phencarbamide, phencyclidine, phendimetrazine, phenelzine, pheneridine, phenesterin, penethicillin, phenformin, phenglutarimide, phenicarbazide, phenindamine, phenindione, phenipirazine, pheniraminie, phenisonone, phenmetrazine, phenobarbital, phenobutiodil, phenolphtalein, phenolsulfonphthalein, phenomorphan, phenoperidine, phenothiazine, phenothrin, phenoxybenzamine, phenoxypropazine, phenprobamate, phenprocoumon, phenpromethamine, phensuximide, phentermine, phentolamine, phenylalanine, phenyl aminosalicylate, phenylbutazone, phenylethyl alcohol, phenylmercuric acetate, phenylmercuric borate, phenylmercuric chloride, phenylmercuric nitrate, phenylmethylbarbituric acid, phenylpropanolamine, phenylthilqne, phenyltoloxamine, phenyramidol, phenyloin, phethafbital, pholcodine, pholedrine, phosphoramide mustard, phoxim, phthalofyne, phthalysulfacetamide, phthalylsulfamethizole, phthalylsulfathiazole, phytic acid, phytonadiol diphosphate, phytonadione, pibecarb, pibenzimol, pibecarb, pibenzimol, piberaline, picafibrate, picartamide, picenadol, picilorex, piclonidine, piclopastine, picloxydine, picobenzide, picodralazine, picolamine, piconol, picoperine, picoprazole, picotamide, picotrin diolamine, picumast, pidolic acid, pifamine, pifenate, pifexole, piflutixole, pifoxime, piketoprofen, pildralazine, pimoclone, pimefhylline, pimelautde, pimetacin, pimethixene, pimetine, pimetremide, piminodine, pimobendan, pimondiazole, pimozide, pinacidil, pinadoline, pinafide, pinaverium bromide, pinazepam, pincamide, pindolol, pinolcaine, pinoxepin, pioglitazone, pipacycline, pipamazine, pipaperone, pipazethate, pipebuzone, pipecuronium bromide, pipemidic acid, piperidolate bromide, pipequaline, piperacetazine, piperacillin, piperamide, piperazine, piperazinedione, piperidolate, piperilate, piperocaine, piperoxan, piperylone, pipobroman, pipoctanone, pipofezine, piposulfan, pipotiazine palmiate, pipoxizine, pipoxolan, pipradimadol, pipradol, pipramadol, pipratecol, piprinhydrinate, piprocurarium iodide, piprofurol, piprozolin, piquindone, piquizil, piracetam, pirandamine, pirarubicin, piraxelate, pirazmonam, pirazolac, pirbenicillin, pirbuterol, pirdonium bromide, pirenoxine, pirenperone, pirenzepine, pirepolol, piretanide, pirfenidone, piribedil, piridicillin, piridocaine, piridoxilate, piridronic acid, pirifibrate, pirindazole, pirinixic acid, pirinixil, piriprost, piriqualone, pirisudanol, piritramide, piritrexim, pirlimycin, pirlindole, pirmagrel, pirmenol, pirnabine, piroctone, pirogliride, piroheptine, pirolate, pirolazamide, piromidic acid, piroxantrone HCL, piroxicam cinnamate, piroxicillin, piroximone, pirozadil, pirprofen, pirquinozol, pirralkonium bromide, pirtenidine, pitenodil, pitofenone, pituxate, pivampicillin, pivenfrine, pivopril, pivoxazepam, pizotyline, plafibride, plaunotol, pleuromulin, plicamycin, podilfen, podophylloxoxin, poldine methylsulfate, polidocanol, polythiazide, ponalrestat, ponfibrate, porfiromycin, poskine, potassium guaiacolsulfonate, potassium nitrazepate, potassium sodium tartrate, potassium sorbate, potassium thiocyanate, practolol, prajmalium, pralidoxime chloride, pramipexole, pramiracetam, pramiverine, pramoxime, prampine, pranolium chloride, pranoprofen, pranosal, prasterone, pravastatin, praxadine, prazepam, prazepine, praziquantel, prazitone, prazocillin, prazosin, preclamol, prednazate, prednazoline, prednicarbate, prednimustine, prednisolamate, prednisolone, prednisolone hemisuccinate, prednisolone steaglate, prednisolone tebutate, prednisone, prednival, prednylidene, prefenamate, pregnenolone, pregnenolone succinate, premazepam, prenalterol, prenisteine, prenoverine, prenoxdiazine, prenylamine, pretarnazium iodide, pretiadil, pribecaine, pridefine, prideperone, pridinol, prifelone, prifinium bromide, prifuroline, prilocaine, primaperone, primaquine, primidolol, primidone, primycin, prinomide, pristinamycin, prizidilol, proadifen, probarbital, probenecid, probicromil, probucol, procainamide, procaine, procarbazine, procaterol, prochlorperazine, procinolol, procinonide, proclonol, procodazole, procyclidine, procymate, prodeconium bromide, prodilidine, prodipine, prodolic acid, profadol, profexalone, proflavine, proflazepam, progabide, proglumetacin, proglumide, proheptazine, proligestone, proline, prolintane, prolonium iodide, promazine, promegestone, promestriene, promethazine, promolate, promoxolane, pronetalol, propacetamol, propafenone, propamidine, propanidid, propanocaine, propantheline bromide, proparacaine, propatyl nitrate, propazolamide, propendiazole, propentofylline, propenzolate, properidine, propetamide, propetandrol, propicillin, propikacin, propinetidine, propiolactone, propiomazine, propipocaine, propiram, propisergide, propiverine, propizepine, propofol, propoxate, propoxycaine, propoxyphene, propranolol, propyl docetrizoate, propylene glycol, propylene glycol monostearate, propyl gallate, propylhexedrine, propyliodone, propylparaben, propylthiouracil, propyperone, propyphenazone, propyromazine bromide, proquazone, proquinolate, prorenoate potassium, proroxan, proscillaridin, prospidium chloride, prostalene, prosulpride, prosultiamine, proterguride, protheobromine, prothipendyl, prothixene, protiofate, protionamide, protirelin, protizinic acid, protokylol, protoveratine, protriptyline, proxazole, proxibarbal, proxibutene, proxicromil, proxifezone, proxorphan, proxyphylline, prozapine, pseudoephedrine, psilocybine, pumiteba, puromycin, pyrabrom, pyran copolymer, pyrantel, pyrathiazine, pyrazinamide, pyrazofurin, pyricarbate, pyridarone, pyridofylline, pyridostigmine bromide, pyridoxine, pyrimethamine, pyrimitate, pyrinoline, pyrithione zinc, pyrithyldione, pyritidium bromide, pyritinol, pyronine, pyrophenindane, pyrovalerone, pyroxamine, pyrrobutamine, pyrrocaine, pyrroliphene, pyrrolnitrin, pyrvinium chloride, and pytamine.

Also, quadazocine, quadrosilan, quatacaine, quazepam, quazinone, quazodine, quazolast, quifenadine, quillifoline, quinacainol, quinacillin, quinacrine, quinaldine blue, quinapril, quinaprilat, quinazosin, quinbolone, quincarbate, quindecamine, quindonium bromide, quindoxin, quinestradol, quinestrol, quinethazone, quinetolate, quinezamide, quinfamide, quingestanol acetate, quingestrone, quindine, quinine, quinocide, quinpirole, quinterenol, quintiofos, quinuclium bromide, quinupramine, quipazine, and quisultazine.

Also, racefemine, racemethionine, racemethorphan, racemetirosine, raclopride, ractopamine, rafoxanide, ralitoline, raloxifene, ramciclane, ramefenazone, ramipril, ramiprilat, ramixotidine, ramnodignin, ranimustine, ranimycin, ranitidine, ranolazine, rapamycin, rathyronine, razinodil, razobazam, razoxane, reboxetine, recainam, reclazepam, relomycin, remoxipride, renanolone, rentiapril, repirinast, repromicin, reproterol, recimetol, rescinnamine, reserpine, resorantel, resorcinol, resorcinol monoacetate, retelliptine, retinol, revenast, ribavirin, riboflavin, riboflavin 5'-phosphate, riboprine, ribostamycin, ridazolol, ridiflone, rifabutin, rifamide, rifampin, rifamycin, rifapentine, rifaximin, rilapine, rilmazafone, rilmenidine, rilopirox, rilozarone, rimantadine, rimazolium metilsulfate, rimcazole, rimexolone, rimiterol, rimoprogin, riodipine, rioprostil, ripazepam, risocaine, risperidone, ristianol, ristocetin, ritanserin, ritiometan, ritodrine, ritropirronium bromide, ritrosulfan, robenidine, rocastine, rociverine, rodocaine, rodorubicin, rofelodine, roflurante, rokitamycin, roletamide, rolgamidine, rolicyclidine, rolicyprine, roliprine, rolitetracycline, rolodine, rolziracetam, romifenone, romifidine, ronactolol, ronidazole, ronifibrate, ronipamil, ronnel, ropitoin, ropivacaine, ropizine, roquinimex, rosaprostol, rosaramicin, rosaramicin butyrate, rosaramicin propionate, rosoxacin, rosterolone, rotamicillin, rotoxamine, rotraxate, roxarsone, roxatidine acetate, roxibolone, roxindole, roxithromycin, roxolonium metilsulfate, roxoperone, rufloxacin, rutamycin, rutin, and ruvazone.

Also, sabeluzole, saccharin, salacetamide, salafibrate, salantel, salazodine, salazossulfadimedine, salazosulfamide, salazosulfathiazole, salethamide, salfluverine, salicin, salicyl alcohol, salicylamide, salicylanilide, salicylic acid, salinazid, salinomycin, salmefanol, salmeterol, salmisteine, salprotoside, salsalate, salverine, sancycline, sangivamycin, saperconazole, sarcolysin, sarmazenil, sarmoxicillin, sarpicillin, saterinone, satranidazole, savoxepin, scarlet red, scopafungin, seclazone, secnidazole, secobarbital, secoverine, securinine, sedecamycin, seganserin, seglitide, selegiline, selenium sulfide, selprazine, sematilide, semustine, sepazonium chloride, seperidol, sequifenadine, serfibrate, sergolexole, serine, sermetacin, serotonin, sertaconazole, sertraline, setastine, setazindol, setiptiline, setoperone, sevitropium mesilate, sevoflurane, sevopramide, siagoside, sibutramine, siccanin, silandrone, silibinin, silicristin, silidianin, silver sulfadiazine, simetride, simfibrate, simtrazene, simvastatin, sinefungin, sintropium bromide, sisomicin, sitalidone, sitofibrate, sitogluside, sodium benzoate, sodium dibunate, sodium ethasulfate, sodium formaldehyde sulfoxylate, sodium gentisate, sodium gualenate, sodium nitrite, sodium nitroprusside, sodium oxybate, sodium phenylacetate, sodium picofosfate, sodium picosulfate, sodium stibocaptate, sodium stibogluconate, sodium tetradecyl sulfate, sodium thiosulfate, sofalcone, solasulfone, solpecainol, solypertine, somantadine, sopitazine, sopromidine, soquinolol, sorbic acid, sorbinicate, sorbinil, sorbitan monolaurate, sorbitan monooleate, sorbitan monopalmitate, sorbitan monostearate, sorbitan trioleate, sorbitan tristearate, sorbitol, sorndipine, sotalol, soterenol, spaglumic acid, sparfosic acid, sparsomycin, sparteine, spectinomycin, spiclamine, spiclomazine, spiperone, spiradoline, spiramide, spiramycin, spirapril, spiraprilat, spirendolol, spirgetine, spirilene, spirofylline, spirogermanium, spiromustine, spironolactone, spiroplatin, spirorenone, spirotriazine, spiroxasone, spiroxatrine, spiroxepin, spizofurone, stallimycin, stanolone, stanzolol, stearic acid, stearyl alcohol, stearylsulfamide, steffimycin, stenbolone acetate, stepronin, stercuronium iodide, stevaladil, stibamine glucoside, stibophen, stilbamidine, stilbazium iodide, stilonium iodide, stirimazole, stiripentol, stirocamide, stirofos, streptomycin, streptonicozid, streptonigrin, streptovarycin, streptozocin, strinoline, strychnine, styramate, subathizone, subendazole, succimer, succinylcholine chloride, succinylsulfathiazole, succisulfone, suclofenide, sucralfate, sucrose octaacetate, sudexanox, sudoxicam, sufentanil, sufosfamide, sufotidine, sulazepam, sulbactam, sulbactam pivoxil, sulbenicillin, sulbenox, sulbentine, sulbutiamine, sulclamide, sulconazole, sulfabenz, sulfabenzamide, sulfacarbamide, sulfacecole, sulfachlorpyridazine, sulfachrysoidine, sulfaclomide, sulfaclorazole, sulfaclozine, sulfacytine, sulfadicramide, sulfadimethoxine, sulfadoxine, sulfaethidole, sulfaguandide, sulfaguanole, sulfalene, sulfaloxic acid, sulfamazone, sulfamerazine, sulfameter, sulfamethazine, sulfamethoxazole, sulfamethoxypyridazine, sulfamethoxypyridazine acetyl, sulfametomidine, sulfametrole, sulfamonomethoxine, sulfamoxole, sulfanil amide, sulfanitran, sulfaperin, sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinalol, sulfinpyrazone, sulfuram, sulfisomidine, sulfisoxazole, sulfobromophthalein, sulfonethylmethane, sulfonmethane, sulfonterol, sulforidazine, sulfoxone sodium, sulicrinat, sulindac, sulisatin, sulisobenzone, sulmarin, sulmazole, sulmepride, sulinidazole, sulocarbilate, suloctidil, sulosemide, sulotroban, suloxifen, sulpiride, sulprosal, sulprostone, sultamicillin, sulthiame, sultopride, sultosilic acid, sultroponium, sulveapride, sumacetamol, sumatriptan, sumetizide, sunagrel, suncillin, supidimide, suproclone, suprofen, suramin, suricamide, suriclone, suxemerid, suxethonium chloride, suxibuzone, symclosene, symetine, synephrine, and syrisingopine.

Also, taclamine, taglutimide, talampicillin, talastine, talbutal, taleranol, talinolol, talipexole, talisomycin, talmetacin, talmetoprim, talniflumate, talopram, talosalate, taloximine, talsupram, taltrimide, tameridone, tameticillin, tametraline, tarnitinol, tamoxipen, tampramine, tandamine, taprostene, tartaric acid, tasuldine, taurocholic acid, taurolidine, tauromustine, tauroselcholic acid, taurultam, tazadolene, tazanolast, tazaburate, tazeprofen, tazifylline, taziprinone, tazolol, tebatizole, tebuquine, teclothiazide, teclozan, tedisamil, tefazoline, tefenperate, tefludazine, teflurane, teflutixol, tegafur, telenzepine, temafloxacin, temarotene, temazepam, temefos, temelastine, temocillin, temodox, temozolomide, temurtide, tenamfetamine, tenilapine, teniloxazine, tenilsetam, teniposide, tenocyclidine, tenonitrozole, tenoxicam, tenylidone, teopranitol, teoprolol, tepirindole, tepoxalin, terazosin, terbinafine, terbucromil, terbufibrol, terbuficin, terbuprol, terbutaline, terciprazine, terconazole, terfenadine, terfluranol, terguride, terizidone, ternidazole, terodiline, terofenamate, teroxalene, teroxirone, terpin hydrate, tertatolol, tesicam, tesimide, testolactone, testosterone, testosterone cypionate, testosterone enanthate, testosterone ketolaurate, testosterone phenylacetate, testosterone propionate, tetrabarbital, tetrabenazine, tetracaine, tetrachloroethylene, tetradonium bromide, tetraethylammonium chloride, tetramethrin, tetramisole, tetrandrine, tetrantoin, tetrazepam, tetriprofen, tetronasin 5930, tetroquinone, tetroxoprim, tetrydamine, texacromil, thalicarpine, thalidomide, thebacon, thebaine, thenalidine, thenium closylate, thenyldiamine, theobromine, theodrenaline, theofibrate, theophylline, thiabendazole, thiacetarsamide, thialbarbital, thiambutosine, thiamine, thiamiprine, thiamphenicol, thiamylal, thiazesim, thiazinamium chloride, thiazolsulfone, thiethyperazine, thihexinol methylbromide, thimerfonate, thimerosal, thiocarbanidin, thiocarzolamide, thiocolchioside, thiofuradene, thioguanine, thioguanine alpha-deoxyriboside, thioguanine beta-deoxyriboside, thioguanosine, thiohexamide, thioinosine, thiopental, thiopropazate, thioproperazine, thioridazine, thiosalan, thiotepa, thiotetrabarbital, thiothixene, thiouracil, thiphenamil, thiphencillin, thiram, thonzonium bromide, thonzylamine, thozalinone, threonine, thymidine, thymol, thymol iodide, thymopentin, thyromedan, thyropropic acid, tiacrilast, tiadenol, tiafibrate, tiamenidine, tiametonium iodide, tiamulin, tianafac, tianeptine, tiapamil, tiapirinol, tiapride, tiaprofenic acid, tiaprost, tiaramide, tiazofurin, tiazuril, tibalosin, tibenalast sodium, tibenzate, tibezonium iodide, tibolone, tibric acid, tibrofan, tic-mustard, ticabesone propionate, ticarbodine, ticarcillin, ticarcillin cresyl, ticlatone, ticrynafen, tidiacic, tiemoium iodide, tienocarbine, tienopramine, tienoxolol, tifemoxone, tiflamizole, tiflorex, tifluadom, tiflucarbine, tiformin, tifurac, tigemonam, tigestol, tigloidine, tilbroquinol, tiletamine, tilidine, tiliquinol, tilisolol, tilmicosin, tilomisole, tilorone, tilozepine, tilsuprost, timefurone, timegadine, timelotem, timepidium bromide, timiperone, timobesone acetate, timofibrate, timonacic, timoprazole, tinabinol, tinazoline, timidazole, tinisulpride, tinofedrine, tinoridine, tiocarlide, tioclomarol, tioconazole, tioctilate, tiodazosin, tiodonium chloride, tiomergine, tiomesterone, tioperidone, tiopinac, tiopronin, tiopropamine, tiospirone, tiotidine, tioxacin, tioxamast, tioxaprofen, tioxidazole, tioxolone, tipentosin, tipepidine, tipetropium bromide, tipindole, tipredane, tiprenolol, tiprinast, tipropidil, tiprostanide, tiprotimod, tiquinamide, tiquizium bromide, tiratricol, tiropramide, tisocromide, tisopurine, tisoquone, tivandizole, tixadil, tixanox, tixocortol pivalate, tizabrin, tianidine, tizolemide, tizoprolic acid, tobuterol, tocamide, tocamphyl, tocofenoxate, tocofibrate, tocophersolan, todralazine, tofenacin, tofetridine, tofisoline, tofisopam, tolamolol, tolazamide, tolazoline, tolboxane, tolbutamide, tolciclate, toldimfos, tolfamide, tolfenamic acid, tolgabide, tolimidone, tolindate, toliodium chloride, toliprolol, tolmesoxide, tolmetin, tolnaftate, tolnapersine, tolnidamine, toloconium metilsulfate, tolonidine, tolonium chloride, toloxatone, toloxychlorinol, tolpadol, tolpentamide, tolperisone, toliprazole, tolpronine, tolpropamine, tolpyrramide, tolquinzole, tolrestat, toltrazuril, tolufazepam, tolycaine, tomelukast, tomoglumide, tomoxetine, tomoxiprole, tonazocine, topiramate, toprilidine, tonazocine, topiramate, toprilidine, topterone, toquizine, torasemide, toebafylline, toremifene, tosifen, tosufloxacin, tosulur, toyocamycin, toyomycin, traboxepine, tracazolate, tralonide, tramadol, tramazoline, trandolapril, tranexamic acid, tranilast, transcainide, trantelinium bromide, tranylcypromine, trapencaine, trapidil, traxanox, trazilitine, trazium esilate, trazodone, trazolopride, trebenzomine, trecadrine, treloxinate, trenbolone acetate, trengestone, trenizine, trosulfan, trepibutone, trepipam, trepirium iodide, treptilamine, trequensin, trestolone acetate, trethinium tosilate, trethocanoic acid, tretinoin, tretoquinol, triacetin, triafungin, triamcinolone acetonide-phosphate, triamcinolone benetonide, triamcinolone diacetate, triamcinolone furetonide, triamcinolone hexacetonide, triampyzine, triamterene, triazinate, triaziquone, triazolam, tribendilol, tribenoside, tribromoethanol, tribromsalan, tribuzone, triacetamide, trichlormethiazide, trichlormethine, trichloroacetic acid, trichloroethylene, tricribine phosphate, triclabendazole, triclacetamol, triclazate, triclobisonicum chloride, triclocarban, triclodazol, triclofenol, piperazine, triclofos, triclofylline, triclonide, triclosan, tricyclamol chloride, tridihexethyl chloride, trientine, triethylenemelamine, triethylenephosphoramide, trifenagrel, trifezolac, triflocin, triflubazam, triflumidate, trifluomeprazine, trifluoperazine, trifluperidol, triflupromazine, trifluridine, triflusal, trigevolol, trihexyphenidyl, triletide, trilostane, trimazosin, trimebutine, trimecaine, trimedoxime bromide, trimeperidine, trimeprazine, trimetazidine, trimethadione, trimethamide, trimethaphan camsylate, trimethidinium methosulfate, trimethobenzamide, trimethoprim, trimetozine, trimetrexate, trimexiline, trimipramine, trimoprostil, trimoxamine, trioxifene, trioxsalen, tripamide, triparanol, tripelennamine, tripotassium dicitratobismuthate, triprolidine, tritiozine, tritoqualine, trityl cysteine, trixolane, trizoxime, trocimine, troclosene potassium, trofosfamide, troleandomycin, trolnitrate, tromantadine, tromethamine, tropabazate, tropanserin, tropapride, tropatepine, tropenziline bromide, tropigline, tropiprine, tropodifene, trospectomycin, trospium chloride, troxerutin, troxipide, troxolamide, troxonium tosilate, troxypyrrolium tosilate, troxypyrrolium tosilate, truxicurium iodide, truxipicurium iodide, tryparsamide, tryptophan, tryptophane mustard, tuaminoheptane, tubercidine, tubocurarine chloride, tubulozole, tuclazepam, tulobutrol, tuvatidine, tybamate, tylocrebin, tylosin, tyramine, tyropanic acid, and tyrosine.

Also, ubenimex, ubidecarenone, ubisindine, ufenamate, ufiprazole, uldazepam, ulobetasol, undecoylium chloride, undecyclenic acid, uracil mustard, urapidil, urea, uredepa, uredofos, urefibrate, urethane, uridine, ursodeoxycholic acid, and ursucholic acid.

Also, vadocaine, valconazole, valdetamide, valdipromide, valine, valnoctamide, valofane, valperinol, valproate pivoxil, valproic acid, valpromide, valtrate, vancomycin HCl, vaneprim, vanillin, vanitolide, vanyldisulfamide, vapiprost, vecuronium bromide, velnacrine maleate, venlafaxine, veradoline, veralipride, verapamil, verazide, verilopam, verofylline, vesnarinone, vetrabutine, vidarabine, vidarabine phophate, vigabatrin, viloxazine, viminol, vinbarbital, vinblastine, vinburnine, vincamine, vincanol, vincantril, vincofos, vinconate, vincristine, vindrburnol, vindesine, vindepidine, vinformide, vinglycinate, vinpocetine, vinpoline, vinrosidine, vintiamol, vintriptol, vinylbital, vinylether, vinzolidine, viomycin, viprostol, viqualine, viquidil, virginiamycin factors, viroxime, visnadine, visnafylline, vitamine, and volazocine.

Also, warfarin.

Also, xamoterol, xanoxic acid, xanthinol niacinate, xanthiol, xantifibrate, xantocillin, xenalipin, xenazoic acid, xenbucin, xenipentone, xenthiorate, xenygloxal, xenyhexenic acid, xenylropium bromide, xibenolol, xibornol, xilobam, ximoprofen, xinidamine, xinomiline, xipamide, xipranolol, xorphanol, xylamidine, xylazine, xylocoumarol, xylometazoline, and xyloxemine.

Also, yohimbic acid.

Also, zabicipril, zacopride, zafuleptine, zaltidine, zapizolam, zaprinast, zardaverine, zenazocine mesylate, zepastine, zeranol, zetidoline, zidapamide, zidometacin, zidovudine, zilantel, zimeldine, zimidoben, zinc acetate, zinc phenolsulfonate, zinc undecylenate, zindotrine, zindoxifene, zinoconazole, zinterol, zinviroxime, zipeprol, zocainone, zofenopril, zoficonazole, zolamine, zolazepam, zolenzepine, zolertine, zolimidine, zoliprofen, zoloperone, zolpidem, zomebazam, zomepirac, zometapine, zonisamide, zopiclone, zorubicin, zotepine, zoxazolamine, zuclomiphene, zuclophenthixol, and zylofuramine.

The bioactive agent can be present as a liquid, a finely divided solid, or any other appropriate physical form. Typically, but optionally, the biodegradable composition will include one or more additives, such as diluents, carriers, excipients, stabilizers, or the like.

The particular bioactive agent, or combination of bioactive agents, can be selected depending upon one or more of the following factors: the application of the device (for example, subretinal implant or intraocular implant), the amount of the device composed of the polymeric material (for example, percentage of the device fabricated of degradable material, inclusion of a biodegradable material as a coating on a surface of the body member, as well as the amount of surface provided with the coating), the condition to be treated, the anticipated duration of treatment, characteristics of the implantation site, the number and type of bioactive agents to be utilized, and the like.

The concentration of the bioactive agent in the polymeric material can be provided in the range of about 0.01% to about 75% by weight, or about 0.01% to about 50% by weight, based on the weight of the final polymeric material. Preferably, the bioactive active agent is present in the polymeric material in an amount in the range of about 75% by weight or less, preferably about 50% by weight or less. The amount of bioactive agent in the polymeric material can be in the range of about 1 µg to about 10 mg, or about 100 µg to about 1000 µg, or about 100 µg to about 500 µg.

In some aspects, the concentration of bioactive agent can also be selected to provide a desired elution rate from the device. As discussed herein, some aspects of the invention provide methods including steps of selecting one or more bioactive agents to administer to a patient, determining a treatment course for a particular patient, and formulating the polymeric material to achieve the treatment course.

In some aspects, the concentration of bioactive agent can be selected to provide a desired tissue concentration of bioactive agent at the treatment site. Given the site-specific nature of the inventive devices, methods and systems, it will be apparent that the tissue concentration of bioactive agent will be greater at the treatment site than at areas within the patient outside the treatment site. As discussed herein, this provides several benefits to the patient, such as reduced risk of toxic levels of the bioactive agent within the body, reduced risk of adverse affects caused by bioactive agent outside the treatment site, and the like. The location of the bioactive agent on or within the device and on or within the polymer can also affect tissue concentration of bioactive agent (for example, when substantially the entire device body includes bioactive agent, or selected portion(s) of the device body include bioactive agent). Moreover, inclusion of optional coating layers that contain bioactive agent can also impact tissue concentration of bioactive agent.

The particular bioactive agent, or combination of bioactive agents, can be selected depending upon one or more of the following factors: the application of the device (for example, subretinal implant, intraocular implant, intraocular injection, and the like), the amount of the device composed of the polymer material, the condition to be treated, the treatment method, the anticipated duration of treatment, characteristics of the implantation site, the number and type of bioactive agents to be utilized, and the like.

The amount of the bioactive agent that is to be delivered to the treatment site may be determined by one of ordinary skill in the art and will vary depending on the condition to be treated and the particular treatment method. In addition, the amount also will depend upon the particular formulation of the bioactive agent. Further, the amount of the bioactive agent to be delivered also takes into account the period of time expected for administration and/or treatment and/or the frequency or periodicity of such administration and/or treatment.

In some embodiments, an intraocular or subretinal sustained release delivery device has a bioactive agent elution rate of at least 0.0001 µg per day, in other embodiments at least 0.001 µg per day, in other embodiments at least 0.01 µg per day, in other embodiments at least 0.1 µg per clay, in other embodiments at least 1 µg per day, in other embodiments at least 10 µg per day. In some embodiments, an intraocular device has an elution rate of at least 0.01 µg per day, in other embodiments at least 0.1 µg per day, in other embodiments at least 1 µg per day, in other embodiments at least 10 µg per day, in other embodiments at least 100 µg per day, and in other embodiments at least 1000 µg per day.

The elution rate can vary and can be customized as desired for each type of eye condition treated, the nature of the ocular tissue being treated (for example, subretinal versus intraocular), the treatment method, the selected bioactive agent(s), the potency of bioactive agent(s), the size of the bioactive agent(s), and the severity of the condition being treated. In some aspects, the elution rate can be customized depending upon any physiological barriers that may exist between the implant site and the tissue to be treated. In general, it is desired to maximize the total bioactive agent(s) loading while maintaining mechanical integrity of the device.

The sustained release delivery devices can be implanted to release or deliver bioactive agent(s), more particularly a therapeutic dosage of the bioactive agent(s), for a sustained period of time, that is for example for about 1 month to about 20 years, such as from about 6 months to about 5 years and more specifically from about 3 months to 2 years. In some embodiments the sustained release device releases the bioactive agent(s) by pseudo zero order release kinetics.

The devices can be utilized to deliver any desired bioactive agent or combination of bioactive agents to the eye, such as the bioactive agents described herein. The amount of bioactive agent(s) delivered over time is preferably within the therapeutic level, and below the toxic level. For example, a preferred target dosage for intraocular delivery of triamcinolone acetonide for use in treating diseases or disorders of the eye is preferably in the range of about 0.5 µg/day to about 10 µg per day. Preferably, the treatment course is greater than 6 months, more preferably greater than one year. Thus, in preferred embodiments, the bioactive agent is released from the coated composition in a therapeutically effective amount for a period of 6 months or more, or 9 months or more, or 12 months or more, or 36 months or more, when implanted in a patient.

In some aspects, the concentration of bioactive agent(s) can also be selected to provide a desired elution rate from the device. As discussed herein, some aspects of the invention provide methods including steps of selecting one or more bioactive agents to administer to a patient, determining a treatment course for a particular patient, and formulating the polymeric material to achieve the treatment course.

In some aspects, the concentration of bioactive agent can be selected to provide a desired tissue concentration of bioactive agent at the treatment site. Given the site-specific nature of the devices and methods, it will be apparent that the tissue concentration of bioactive agent will be greater at the treatment site than at areas within the patient outside the treatment site. As discussed herein, this provides several benefits to the patient, such as reduced risk of toxic levels of the bioactive agent within the body, reduced risk of adverse affects caused by bioactive agent outside the treatment site, and the like. The location of the bioactive agent on or within the device and on or within the polymer can also affect tissue concentration of bioactive agent (for example, when substantially the entire device includes bioactive agent, or selected portion(s) of the device include bioactive agent). Moreover, inclusion of optional coating layers that contain bioactive agent can also impact tissue concentration of bioactive agent.

In some embodiments, the invention provides for the treatment of disorders or diseases of the choroid and the retina. As such, the bioactive agents may be instilled directly in the choroid, the retina or subretinal space, so as to deliver the bioactive agent precisely to the portion of the tissue being treated. In some embodiments, the invention provides for the treatment of disorders or diseases via intraocular routs, for example, using devices that are inserted and implanted in the vitreous of the eye. Such localized delivery to various targeted portions of the eye is efficient and delivers the bioactive agent substantially only to the portion of the eye being treated and does not deliver any significant amount of bioactive agent to healthy tissues. As used herein, the terminology delivery substantially only to the portion of the eye being treated is understood to mean that at least 5%, more preferably at least 10%, more preferably at least 20%, more preferably at least 30%, more preferably at least 40%, more preferably at least 50%, more preferably at least 60%, more preferably at least 70%, more preferably fit least 75%, more preferably at least 80% more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably all of the bioactive agent delivered by the device is delivered to the treatment site. As used herein, the terminology "does not deliver any significant amount of bioactive agent to healthy tissues" is understood to mean that less than 95%, more preferably less than 90%, more preferably less than 80%, more preferably less than 70%, more preferably less than 60%, more preferably less than 50%, more preferably less than 40%, more preferably less than 30%, more preferably less than 20%, more preferably less than 15%, more preferably less than 10%, more preferably less than 5%, more preferably less than 4%, more preferably less than 3%, more preferably less than 2%, more preferably less than 1% of the total bioactive agent delivered by the device.

This is in contrast to systemic, topical, and oral delivery mechanisms that may have been used to treat diseases and disorders of the eye, as such mechanisms require the administration of significantly larger dosages of bioactive agents systemically, topically, or orally so as to deliver a therapeutically effective amount of bioactive agent to the treatment site.

Polymers

Polymers useful in the sustained release delivery devices (e.g., as cores and/or as coating layers) are biocompatible and may be biodegradable or biostable (i.e., non-biodegradable). Representative biostable polymers include polyurethanes, silicones, polyesters, polyolefins (e.g., polyethylene or polypropylene), polyisobutylene, acrylic polymers, vinyl halide polymers, polyvinyl ethers, polyvinyl methyl ether, polyvinylidene halides, polyacrylonitrile, polyvinyl ketones, polyvinyl aromatics, polyvinyl esters (e.g., poly(alkyl(meth) acrylates) such as poly((methyl)methacrylate) or poly((butyl) methacrylate)), polyvinyl amides, polyamides, polycaprolactam, polycarbonates, polyoxymethylenes, polyimides, polyethers, polyurethanes, rayon, rayon-triacetate, cellulose acetate, cellulose butyrate, cellophane, cellulose nitrate, cellulose propionate, cellulose ethers, carboxymethyl cellulose and copolymers (e.g., polyethylene vinyl acetate) and blends of the above polymers.

Representative examples of biodegradable polymers include poly(L-lactic acid), polycaprolactone, poly(lactide-co-glycolide), poly(hydroxybutyrate), poly(hydroxybutyrate-co valerate), polydioxanone, polyorthoesters, polyanhydrides, poly(glycolic acid), poly(D,L lactic acid), poly (glycolic acid-co-trimethylene carbonate), poly(phosphate esters), polyphosphoester urethanes, poly(amino acids), cyanoacrylates, poly(trimethylene carbonates), polycarbonates, poly(iminocarbonates), polyesters, copoly(ether-esters), polyalkylene oxalates, polyphosphazenes and copolymers and blends of the above polymers. Biodegradable materials such as fibrin, fibrinogen, cellulose, dextrans, polysaccharides, starch collagen, chromic gut, and hyaluronic acid could also be used.

Selection of the polymers may depend, for example, on the desired properties of the sustained delivery device including the desired bioactive agent that is to be delivered by the device and the rate and duration of desired bioactive agent release.

In some embodiments, the biocompatible polymer is made up, in whole or in part, of repeating caprolactone monomer units (e.g., poly(caprolactone) or co-polymers thereof). It has been found that polycaprolactone is well tolerated by the retinal tissue and can elute bioactive agents without eliciting unacceptable inflammatory response or complications. For example, polycaprolactone can elute steroid for a period of at least 4 weeks without eliciting unacceptable inflammatory response or complications. Thus, in one embodiment, the device is formed using a biodegradable polycaprolactone polymer matrix. In another embodiment, the device includes corticosteroid triamcinolone acetonide in a biodegradable polycaprolactone polymer matrix. Such embodiments may optionally include a core.

In some embodiments the polymer comprises a first polymer and a second polymer. Suitable first polymers and second polymers can be prepared using conventional organic synthesis procedures and/or are commercially available from a variety of sources. Preferably, such polymers are either provided in a form suitable for in vivo use or are purified for such use to a desired extent (for example, by removing impurities) by conventional methods available to those skilled in the art.

For application to a core, a coating composition can be prepared to include a solvent, a first polymer and second polymer dissolved in the solvent, and one or more bioactive agents dispersed in the polymer/solvent. The solvent is preferably one in which the polymers form a true solution. The bioactive agent(s) can either be soluble in the solvent or may form a dispersion in the solvent. In some embodiments, the solvent is tetrahydrofuran (THF). Other solvents may also be used, for example, alcohols (such as methanol, butanol, propanol, isopropanol, and the like), alkanes (such as halogenated or unhalogenated alkanes such as hexane and cyclohexane), amides (such as dimethylformamide), ethers (such as dioxolane), ketones (such as methylketone), aromatic compounds (such as toluene and xylene), acetonitrile, and esters (such as ethyl acetate).

The coating layer formed from the coating composition is biocompatible. In addition, the layer is preferably useful under a broad spectrum of both absolute concentrations and relative concentrations of the polymers. In the context of the previous sentence, the physical characteristics of the coating layer (such as tenacity, durability, flexibility and expandability) will typically be suitable over a broad range of polymer concentrations. Furthermore, the ability to control the release rates of a variety of bioactive agents can preferably be manipulated by varying the absolute and/or relative concentrations of the polymers and/or the bioactive agent(s).

In one embodiment, the polymer matrix comprises a hydrogel. Representative examples of hydrogels include the dextran-based hydrogels described in WO 02/17884 (Hennink et al.).

In one embodiment, the polymeric material comprises a composition as described in U.S. Pat. No. 6,214,901 (Chudzik et al.) and U.S. Publication No. 2002/0188037 A1 (Chudzik et al.) (each commonly assigned to the assignee of the present invention). As described therein, the composition comprises a plurality of polymers, including at least two polymer components, for example, primary and secondary polymer components. As used herein "primary" and "secondary" are used solely for designation of the polymer components are not intended to reflect the relative amounts of polymer components in the composition. The polymer components are adapted to be mixed to provide a mixture that exhibits an optimal combination of physical characteristics (such as adherence, durability, flexibility) and bioactive release characteristics as compared to the polymers when used alone or in admixture with other polymers previously known. For example the polymeric material can include an adherent polymer and a polymer having drug release characteristics.

In some aspects the adherent polymer preferably includes poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Examples of suitable poly(alkyl (meth)acrylates) include those with alkyl chain lengths from 2 to 8 carbons, inclusive, and with molecular weights from 50 kilodaltons to 900 kilodaltons. In one preferred embodiment the polymeric material includes a poly(alkyl (meth)acrylate) with a molecular weight of from about 100 kilodaltons to about 1000 kilodaltons, preferably from about 150 kilodaltons to about 500 kilodaltons, most preferably from about 200 kilodaltons to about 400 kilodaltons. An example of a particularly preferred polymer is poly (n-butyl methacrylate). Examples of other preferred polymers are poly(n-butyl methacrylate-co-methyl methacrylate, with a monomer ratio of 3:1, poly(n-butyl methacrylate-co-isobutyl methacrylate, with a monomer ratio of 1:1 and poly(t-butyl methacrylate). Such polymers are available commercially (e.g., from Sigma-Aldrich, Milwaukee, Wis.) with molecular weights ranging from about 150 kilodaltons to about 350 kilodaltons, and with varying inherent viscosities, solubilities and forms (e.g., as slabs, granules, beads, crystals or powder).

Examples of suitable poly(aromatic (meth)acrylates) include poly(aryl (meth)acrylates), poly(aralkyl (meth)acrylates), poly(alkaryl (meth)acrylates), poly(aryloxyalkyl (meth)acrylates), and poly (alkoxyaryl (meth)acrylates).

Examples of suitable poly(aryl (meth)acrylates) include poly(9-anthracenyl methacrylate), poly(chlorophenyl acrylate), poly(methacryloxy-2-hydroxybenzophenone), poly (methacryloxybenzotriazole), poly(naphthyl acrylate), poly (naphthylmethacrylate), poly-4-nitrophenylacrylate, poly (pentachloro(bromo, fluoro) acrylate) and methacrylate, poly (phenyl acrylate) and poly(phenyl methacrylate). Examples of suitable poly(aralkyl (meth)acrylates) include poly(benzyl acrylate), poly(benzyl methacrylate), poly(2-phenethyl acrylate), poly(2-phenethyl methacrylate) and poly(1-pyrenylmethyl methacrylate). Examples of suitable poly(alkaryl(meth) acrylates include poly(4-sec-butylphenyl methacrylate), poly (3-ethylphenyl acrylate), and poly(2-methyl-1-naphthyl methacrylate). Examples of suitable poly(aryloxyalkyl (meth)acrylates) include poly(phenoxyethyl acrylate), poly (phenoxyethyl methacrylate), and poly(polyethylene glycol phenyl ether acrylate) and poly(polyethylene glycol phenyl ether methacrylate) with varying polyethylene glycol molecular weights. Examples of suitable poly(alkoxyaryl (meth)acrylates) include poly(4-methoxyphenyl methacrylate), poly(2-ethoxyphenyl acrylate) and poly(2-methoxynaphthyl acrylate).

Acrylate or methacrylate monomers or polymers and/or their parent alcohols are commercially available from Sigma-Aldrich (Milwaukee, Wis.) or from Polysciences, Inc, (Warrington, Pa.).

One of the other polymer components in the mixture provides an optimal combination of similar properties, and particularly when used in admixture with the primary polymer component. Examples of suitable secondary polymers are available commercially and include poly(ethylene-co-vinyl acetate) having vinyl acetate concentrations in the range of about 1% to about 50%, in the form of beads, pellets, granules, and the like.

In some embodiments, the composition comprises at least one poly(alkyl)(meth)acrylate, as a primary, adherent polymeric component, and poly(ethylene-co-vinyl acetate) as a secondary polymeric component. Preferably, the polymer mixture includes mixtures of poly(butylmethacrylate) (PBMA) and poly(ethylene-co-vinyl acetate) (pEVA). This mixture of polymers has proven useful with absolute polymer concentrations (total combined concentrations of both polymers in the composition) in the range of about 0.25 to about 70% (by weight). It has furthermore proven effective with individual polymer concentrations in the coating solution in the range of about 0.05 to about 70% (by weight). In one preferred embodiment, the polymer mixture includes poly (n-butylmethacrylate) (PBMA) with a molecular weight in the range of about 100 kD to 900 kD and a pEVA copolymer with a vinyl acetate content in the range of about 24 to 36% (by weight). In another preferred embodiment, the polymer mixture includes poly (n-butylmethacrylate) (PBMA) with a molecular weight in the range of about 200 kD to 400 kD and a pEVA copolymer with a vinyl acetate content in the range of about 30 to 34% (by weight). According to these embodiments, the concentration of the bioactive agent or agents dissolved or suspended in the coating mixture can be in the range of about 0.01 to 90%, by weight, based on the weight of the final coating composition.

Other useful mixtures of polymers that can be included in the coating composition are described in commonly assigned U.S. Provisional Application Ser. No. 60/559,821, filed Apr. 6, 2004, and entitled "Coating Compositions For Bioactive Agents". These blends include a first polymer and a second polymer. The first polymer can be selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. A second polymer can be selected from the group consisting of poly(alkyl (meth)acrylates) and poly(aromatic(meth)acrylates).

Other useful mixtures of polymers that can be included in the coating are described in U.S. Publication No. 2004/0047911. This publication describes polymer blends that include poly(ethylene-co-methacrylate) and a polymer selected from the group consisting of a poly(vinyl alkylate), a poly(vinyl alkyl ether), a poly(vinyl acetal), a poly(alkyl and/or aryl methacrylate) or a poly(alkyl and/or aryl acrylate); not including pEVA.

The polymeric material can also be a styrene copolymer, such as poly(styrene-isobutylene-styrene); the preparation of medical devices having such coatings that include poly(styrene-isobutylene-styrene) is described in, for example, U.S. Pat. No. 6,669,980.

The invention will now be described with reference to the following non-limiting examples.

Example 1

Materials Used

Polycaprolactone (Average Mw 80,000, $[-O(CH_2)_5 CO-]_n$, Melt index 125° C./0.3 MPa, Sigma Aldrich Biochemicals, St. Louis, Mo.)
Triamcinolone acetonide (Purity 99%, $M_n$ 434.5, $C_{24}H_{31}FO_6$, Sigma Aldrich Biochemicals, St. Louis, Mo.)
Prednisolone (Purity 99%, $C_{21}H_{28}O_5$, $M_n$ 360.5, Sigma Aldrich Biochemicals, St. Louis, Mo.)
Chloroform (purity 99.8%, $CHCl_3$, A.C.S. spectroscopic grade, Sigma Aldrich Chemicals)
Ether (purity 99%, $M_n$ 74.12, $(C_5H_5)_2O$ A.C.S. reagent, Sigma Aldrich Chemicals)
Balanced salt solution (Sterile, preservative free, Akorn, Inc., Somerset, N.J.)
Bovine serum albumin (Molecular biology grade, Sigma Aldrich Biochemicals, St. Louis, Mo.)
Abbreviations:
PCL: polycaprolactone biodegradable filament
TA: triamcinolone
PCL/TA: biodegradable triamcinolone loaded polycaprolactone filaments
Filament Preparation:

The filaments used in the example were prepared as follows. PCL was solubilized in chloroform at 35° C. overnight under continuous stirring conditions. Triamcinolone acetonide (TA) was then added to the solution in a polymer/drug weight ratio ($w_p/w_D$) of 70:30, 60:40 or 50:50. Once the solution became homogeneous, it was poured onto an evaporating tray and left in a fume hood for 72 hours to solidify. The white solid-form sheath of the TA loaded PCL was rolled into a tight column and packed into a 10 mL syringe. The syringe was heated to 80° C. in a water bath to ensure even heat distribution and to prevent high localized temperatures that could damage the drug or polymer. Although the polymer was not fully in the melt state, the temperature was sufficiently high to initiate the transition of this semi-crystalline closed packed macromolecular polymer to a sufficiently viscous state to be extruded. Additionally, it was noted that drug crystals within the polymer acted as a "flow enhancing" plasticizer when comparing the process to a PCL only filament extrusion.

Once the syringe reached 80° C. it was rapidly removed from the water bath and 1 cm of material was extruded from it. The extruded material was subsequently drawn to a filament by imparting a tensile force. For the 70:30, 60:40 or 50:50 $w_p/w_D$ formulations, ~150 μm filament diameters were achieved by a drawing length of approximately 20, 15 and 10 cm, respectively, while ~300 μm filament diameters were achieved by a drawing length of approximately 15, 10 and 5 cm, respectively. The formulation with the highest drug load (50:50 $w_p/w_D$) broke more frequently during the drawing process. The drawn filament cooled rapidly and could be subsequently cut under a microscope to the desired implantation length.

Filaments without drug were also prepared by directly inserting the PCL pellets into the syringe, heating them to 80° C. and then extruding and drawing in a similar manner to that previously described.

Six pigmented rabbits underwent fluorescein angiography, fundus photography, and optical coherence tomography (Zeiss Model 3000, Germany) at baseline and 4 weeks after implantation. The rabbits were subdivided into the following groups:

Group 1: 2 rabbits with PCL only filaments (PCL, Rabbits 1 and 2);

Group 2: 4 rabbits with PCL/TA 60:40 ($w_p/w_D$) filaments (Rabbits 3-6).

Both groups underwent standard pars plana vitrectomy, and insertion of the drug delivery device into the subretinal space. Briefly, animals were anesthetized with an intramuscular injection of 0.3 mL of ketaminehydrochloride (100 mg/mL; Fort Dodge Lab., Iowa) and 0.1 mL of xylazine hydrochloride (100 mg/mL; Miles Inc, USA) per kilogram of body weight. Pupils were dilated with 1 drop each of 2.5% phenylephrine and 1% tropicamide. A 3-mm peritomy was made at the superotemporal and superonasal quadrant of the right eye. Sclerotomies were created with a 20-gauge microvitreoretinal blade 1 to 2 mm posterior to the limbus in the superotemporal and superonasal quadrants. An infusion line was inserted and sutured through the superonasal sclerotomy and a vitreous cutter (Bausch & Lomb, USA) was inserted through the superotemporal sclerotomy. The vitreous cutter and infusion line were used to perform a 2-port core vitrectomy. The illumination provided by the operating microscope (Zeiss, Germany) was sufficient for the operation.

Using intraocular microscopic forceps (Bausch & Lomb, USA), the filaments were inserted in the subretinal space through a small self-sealing retinotomy. The beveled tip of the implant allowed easy insertion through the retina. The filament was left in position and the forceps was withdrawn from the eye. No laser retinopexy was applied to seal the retinal breaks. The infusion line was removed and the sclerotomies and conjunctival openings were closed using Vycril 7-0 (Ethicon, USA). During week 4, all rabbits underwent fundus examination and were then sacrificed under anesthesia using an intracardiac injection of pentobarbital sodium (Anpro Pharmaceuticals, Oyster Bay, N.Y.).

Elution, Drug Extraction and Histology:
In Vitro Elution

For in vitro drug elution characterization, drug-loaded PCL filaments were prepared according to Table 1.

TABLE 1

In vitro sample parameters

| Sample | Formulation PCL/TA | Diameter (μm) | Length (mm) |
|---|---|---|---|
| 1 | 70:30 | 210 | 30 |
| 2 | 70:30 | 210 | 30 |
| 3 | 70:30 | 250 | 30 |
| 4 | 70:30 | 250 | 30 |
| 5 | 70:30 | 360 | 30 |
| 6 | 60:40 | 150 | 30 |
| 7 | 60:40 | 150 | 30 |
| 8 | 60:40 | 320 | 30 |
| 9 | 60:40 | 320 | 30 |
| 10 | 50:50 | 150 | 30 |
| 11 | 50:50 | 150 | 30 |
| 12 | 50:50 | 320 | 30 |
| 13 | 50:50 | 320 | 30 |

Each filament was placed in a 15 mL capped tube containing 10 mL of a 1% bovine serum albumin (BSA)/balance salt solution (BSS). Tubes were incubated at 37° C. in a shaking water bath (100 rpm). At each time increment of 2, 4, 8, 24, 72, 168, 336, 504 and 672 hours, the filaments were removed from the BSS/BSA solution and placed into a new 10 ml BSS/BSA solution.

After the final time period, the filaments were removed from the BSS/BSA solution and placed in tubes containing 2 mL of ether for complete extraction of the remaining TA. Ether (2 mL) and a 50 μL of internal standard (prednisolone 2 mg/ml) were added to the remaining BSS/BSA solutions. Each solution was vortexed for 2 min and then centrifuged for 3 min at 10,000 rpm to separate the ether and BSS/BSA phases. The top layer ether phase was removed using a glass syringe and added to a 2 mL capped microtube for solvent evaporation in fume hood. Following complete evaporation, 1 mL of 60% methanol was added to the microtube and vortexed. The solution was then transferred to a 1 mL glass shell high performance liquid chromatography (HPLC) vial for analysis.

In Vivo Elution

Two rabbits (PCL/TA 60:40 filaments) were used for analysis of in vivo drug elution. Rabbits were anesthetized prior to the collection of aqueous (~0.3 mL) and blood into lithium heparin tube (2 mL). Rabbits were then euthanized and the eyes enucleated. The implanted device and surrounding tissues (sclera, choroid, retina, lens, and vitreous) were dissected and separated into 2 mL micro tubes. Individual tissue was weighed and then homogenized in 0.5 mL BSS by sonication (1-2 pulse/sec at 50% power). Once completed, samples were enriched with 50 μL internal standard (prednisolone 2 mg/ml) and vortexed. TA was extracted from the tissue sample by adding ether (0.5 mL), vortexing and centrifuging at 10,000 rpm for 10 min. The top ether layer was removed and placed in a new 2 mL microtube for evaporation and substitution of the solvent for methanol as previously described in the in vivo study.

A Millennium high performance liquid chromatograph (Waters Corp., USA) equipped with a 515 pump, 2996 photodiode array detector and 717-plus autosampler injector was used in this study to process the in vitro and in vivo samples.

The Millennium software provided with the high performance liquid chromatograph (HPLC) was used for integration of chromatographic peaks. The solvents were linked to an in-line degasser. The samples were injected into reverse phase HPLC system consisting of stationary phase of Nova-Pak C18 column (3.9×150 mm) and Nova-Pack guard column (Waters Corp., USA); and an isocratic mobile phase of 60% methanol. The peaks of TA and prednisolone were eluted at a flow rate of 1 mL/min with detection at 245 nm. Parallel 50 µL of prednisolone was chromatogramed under the same HPLC condition to determine the extraction efficiency of TA. Further, the co-chromatography technique was adopted to validate the identification of both compounds. The calculation of TA concentration was based on the area peaks and percentage recovery of prednisolone. The HPLC condition separated the peaks of triamcinolone and prednisolone with good resolution. The retention time of prednisolone was 3.46 minutes while that of triamcinolone was 5.2 minutes.

Histology

The eyes of the four remaining rabbits (2 rabbits with PCL only filaments; 2 rabbits with PCL/TA 60:40 filaments) were enucleated and fixed in 4% paraformaldehyde for 24 hours and then Bouin's fixative for a further 24 hours. The specimens were then embedded in paraffin, sectioned, and hematoxylin and eosin (H & E) stained under standard histology laboratory conditions.

Results

Figure 21:
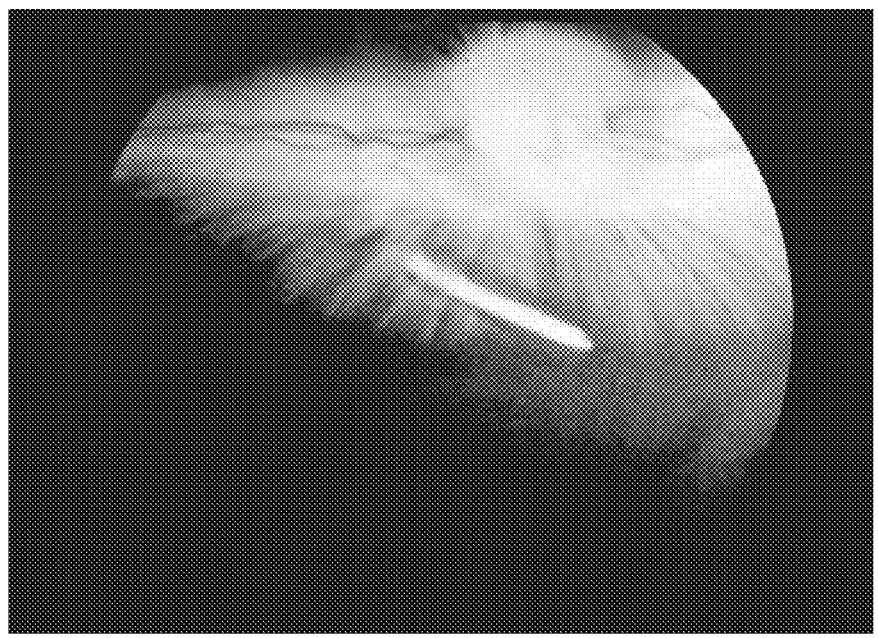
FIG. 21 shows fundus photography (Rabbit 4) of the implanted polycaprolactone/triamcinolone acetonide (PCL/TA) filament at 4 weeks post surgery.
Figure 22:
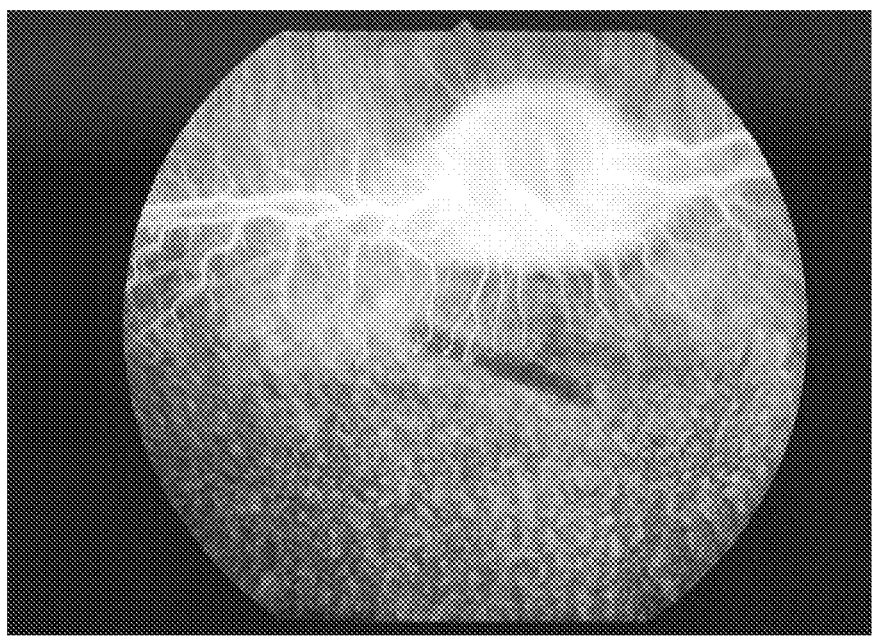
FIG. 22 shows fluorescein angiography (Rabbit 4) of the implanted PCL/TA filament at 4 weeks post surgery.

Clinical examination using slit-lamp and indirect ophthalmoscopy at 1, 2, 3 and 4 weeks showed that there was no detectable accumulation of subretinal fluid, exudates, hemorrhage or fibrosis surrounding the device at any of the follow up points. Fundus photography showed that the filament maintained its position without signs of inflammation or migration, as shown in FIG. 21 for a representative rabbit. Fluorescein angiography demonstrated the absence of vascular leakage, pooling, retinal pigmented epithelium (RPE) abnormalities, or fibrosis at any of the follow-up points for a representative rabbit, as shown in FIG. 22. Optical coherence tomography revealed the successful placement of the implant in the subretinal space of all the rabbit eyes, as shown in FIG. 23.

Figure 23:
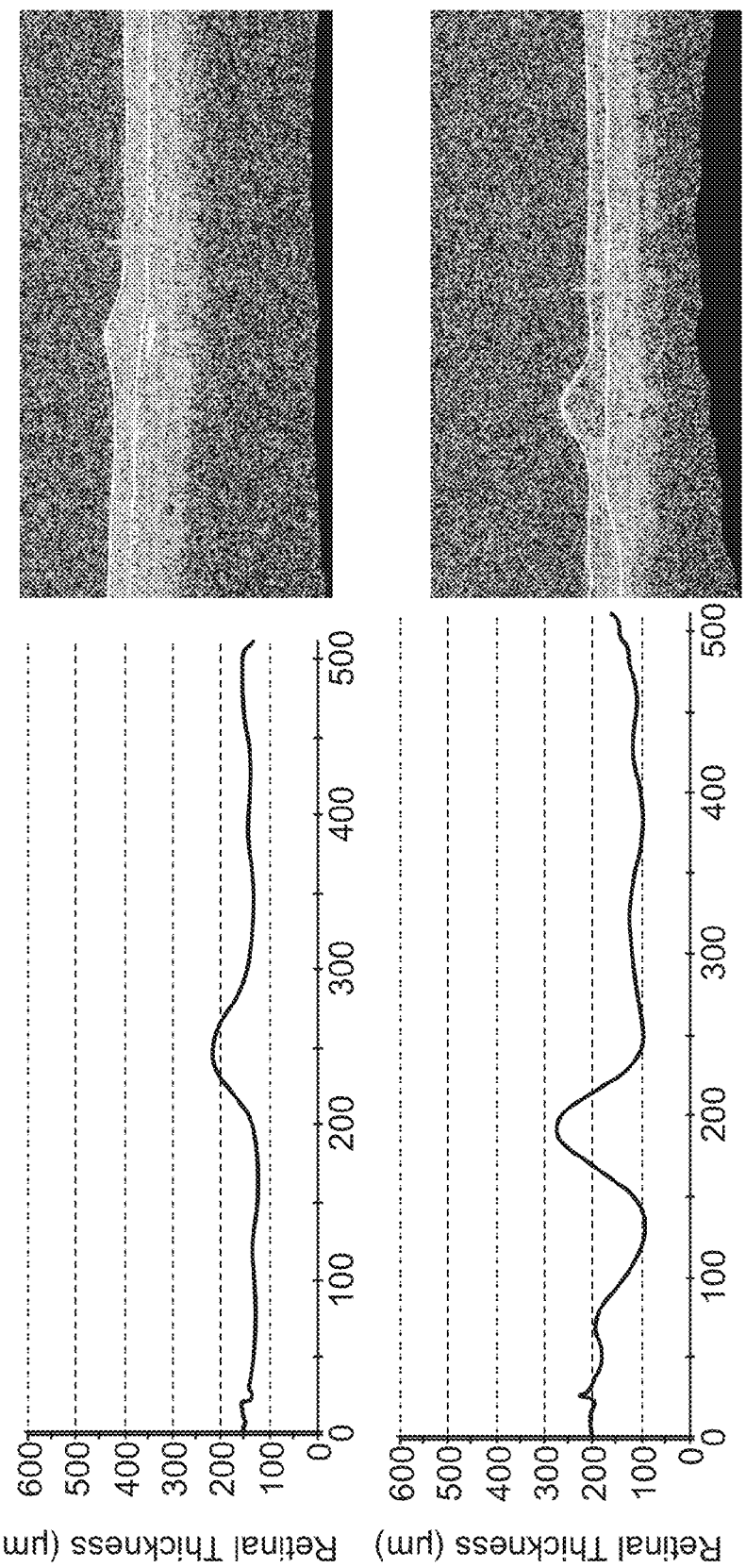
FIG. 23 shows optical coherence tomography of the retinal thickness surrounding the implant site for the polycaprolactone (PCL) filaments (Rabbit 1 and 2) at 4 weeks post surgery.

The topographical effect of using different filament diameters (150 µm vs. 320 µm) can also be seen in FIG. 23 by the comparative increase in retinal thickness at the site of the implant. No abnormalities were reported from increasing the filament diameter. An increase in the filament diameter merely resulted in a slightly more demanding surgical procedure and a larger area of cellular disruption.

Figure 24:
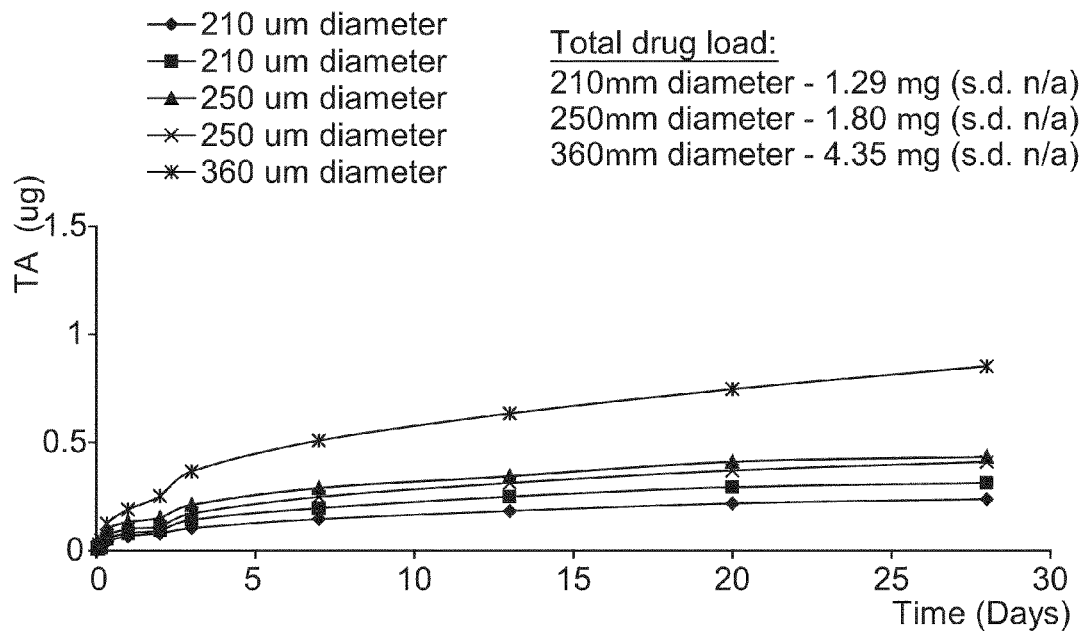
FIG. 24 shows in vitro cumulative elution data for a 70:30 PCL/TA filament.
Figure 25:
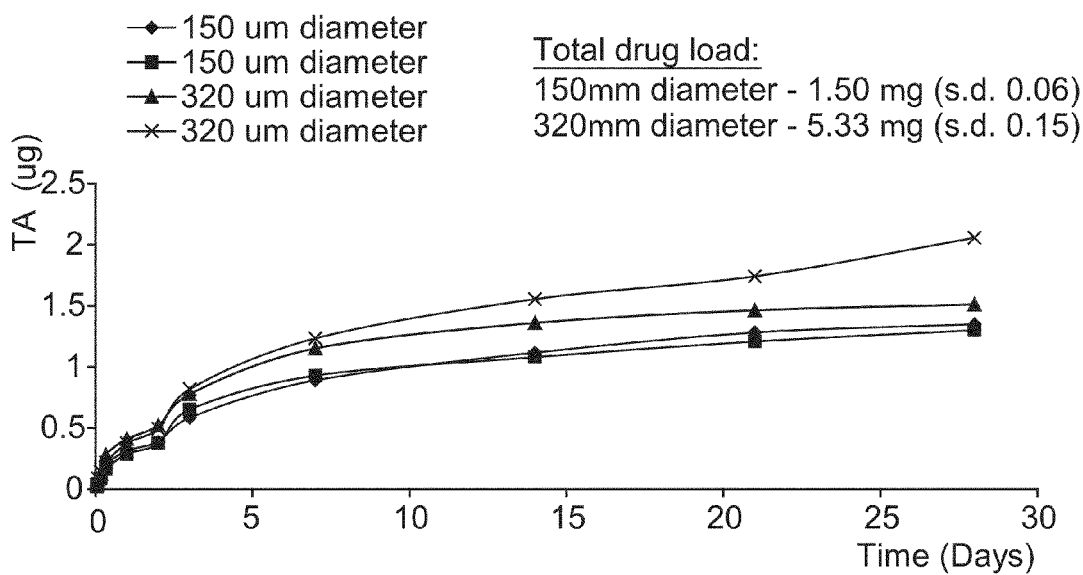
FIG. 25 shows in vitro cumulative elution data for a 60:40 PCL/TA filament.
Figure 26:
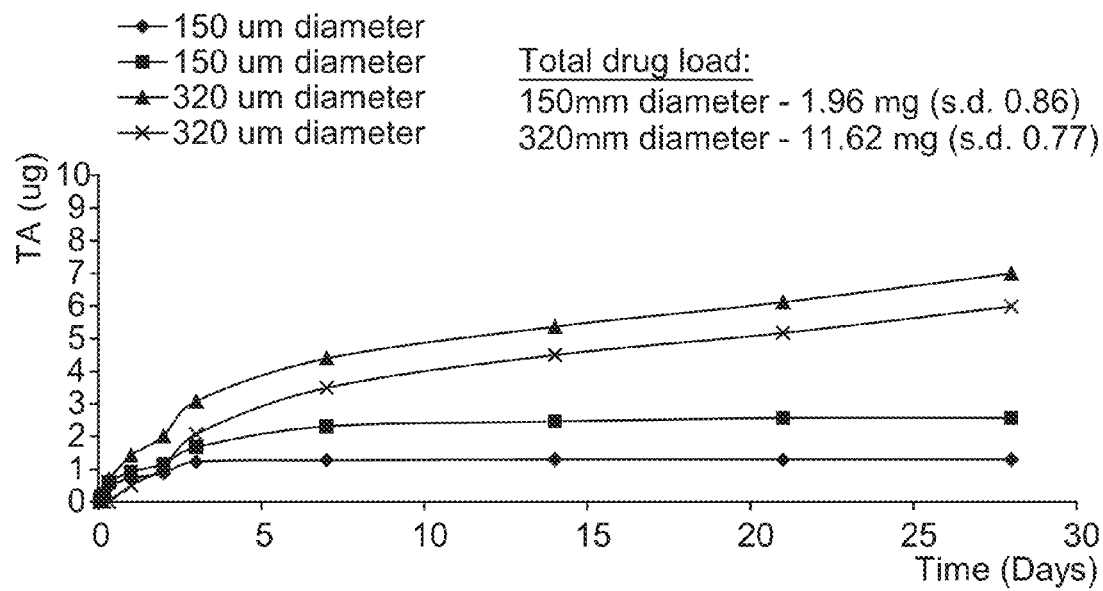
FIG. 26 shows in vitro cumulative elution data for a 50:50 PCL/TA filament.

The in vitro elution rates for the different polymer-drug ratios and geometries into a BSS/BSA (1%) solution are shown in FIGS. 24-26. In general, the elution rates showed an early burst phase followed by a late first order phase. Without being bound by a particular theory, it is believed that the initial early rapid-release phase is attributed to the absorption of drug crystals in the surface to subsurface region of the filament into the medium, preceding diffusion from the polymer core. This initial burst may be particularly useful if it is desired to rapidly achieve local therapeutic dosage. For each of the different polymer-drug ratios, increasing the filament diameter or drug:polymer ratio resulted in an increase in the amount of drug eluted. Without being bound by theory, it is believed that this change results from the increased drug content and/or eluting surface area. For the larger (~300 µm) filaments, increasing the ratio of drug in the formulation from PCL/TA 70:30 to 50:50 also increased the drug elution rate, while a drug dumping effect occurs if both the drug ratio is high (PCL/TA 50:50) and the filament diameter is small, as shown in FIG. 26. In this latter case, total drug release had occurred during the initial burst, and the rate of TA absorption by the subretinal tissue was most likely a limiting factor. The near superimposition of all the elution profiles during the first few hours of each study also indicated that it was the rate of TA absorption that was the limiting step during the first stage of elution. Polycaprolactone is hydrophobic and impermeable to enzyme diffusion; therefore swelling, bulk diffusion, or degradation is unlikely in a bodily environment. Without intending to be bound by a particular theory, the TA elution profile that occurs after the initial surface to subsurface event is believed to be the result of a microporous drug boundary layer being formed and moving deeper toward the core as the TA crystals are progressively absorbed by the body. As a result, the lower the drug loading, the smaller the polymer porosity formed during drug absorption and the lower the rate of TA elution.

Figure 27:
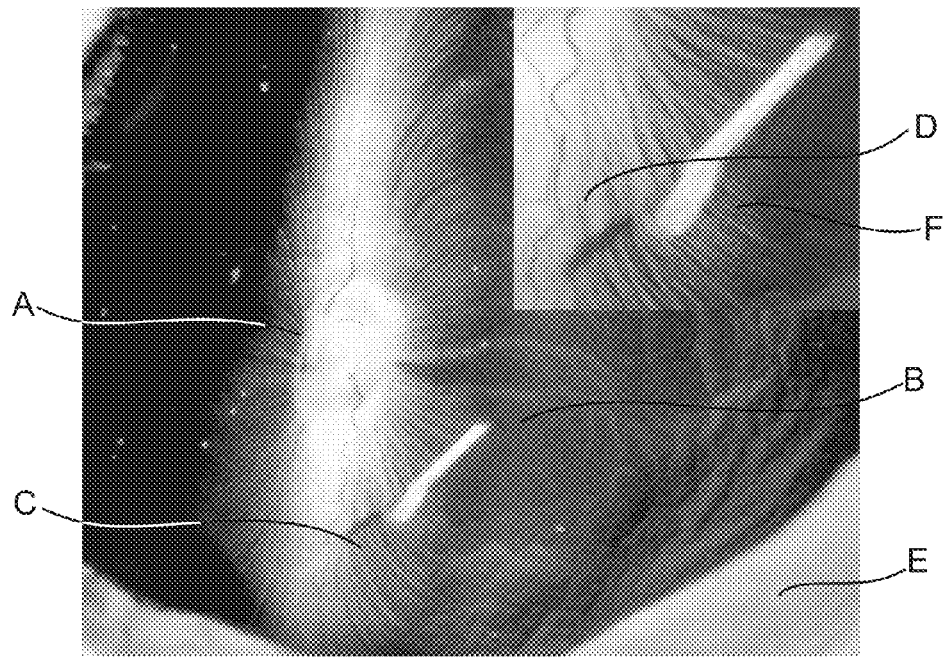
FIG. 27 shows optical image and magnification of the subretinal PCL/TA implant (Rabbit 5) following 4 weeks implantation where A) shows the optic nerve location, B) marks the implant location, C and D) shows the site of the retinotomy, E) is the outer sclera surface, and F) outlines the region of damage to the proximal end of the filament during micro forceps insertion.
Figure 28:
FIG. 28 shows histology (H&E staining) of a 150 μm PCL filament (no drug) following 4 weeks implantation (Rabbit 1) where A) marks the device location, B) shows the RPE, C) shows the nerve fiber layer, D) shows the choroid and E) shows the sclera.
Figure 29:
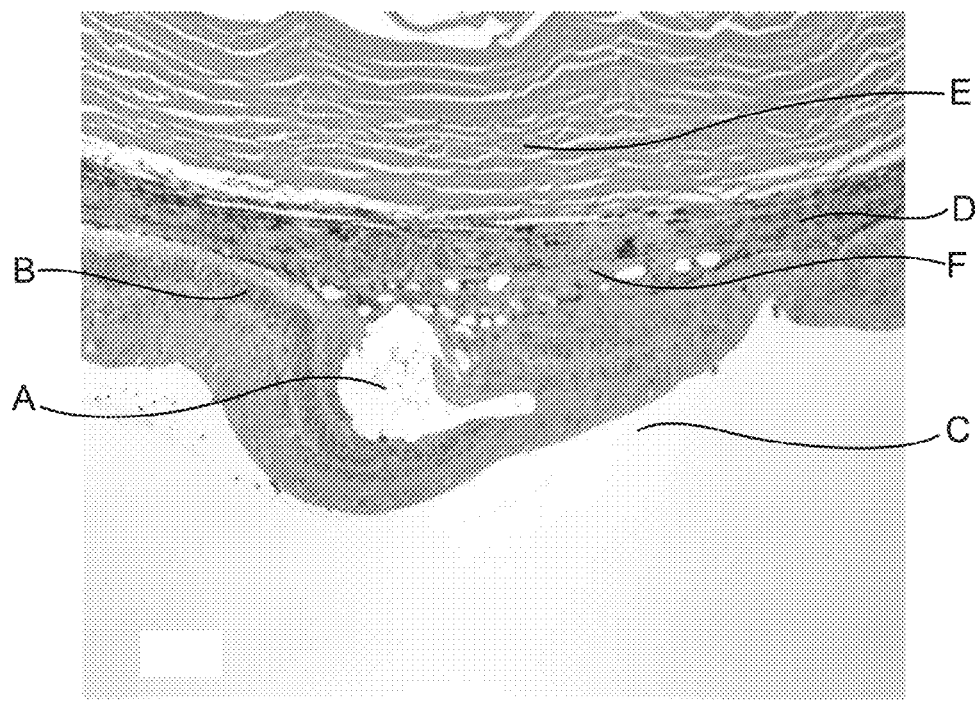
FIG. 29 shows histology (H&E staining) of a 150 μm PCL/TA filament subretinal delivery system following 4 weeks implantation (Rabbit 5) where A) marks the device location, B) shows the RPE, C) shows the nerve fiber layer, D) shows the choroid, E) shows the sclera and F) identifies the region of vacuolated spaces.

Illustrative images (optical and histology staining) of implanted filaments are shown in FIGS. 27 through 29. The size of the retinotomy shown in the optical images is approximately 500 µm. However, smaller sized retinotomies are possible with the use of custom implantation tools.

Figure 30:
FIG. 30 shows explanted PCL/TA filament.

Compared with the initial implant, the explanted filaments at four weeks post surgery had a somewhat more fibrous polymer microstructure, as shown in FIG. 30, than the initial implant. In some studies, only a flaky fibrous/porous polymer microstructure remained once the entire drug was extracted from the device during the in vitro elution studies. The molecular number selected for this polymer was at the high end ($M_w$ 80,000) of the commercially available range. PCL degrades by a reduction in $M_w$, so a longer degradation time is expected with this high $M_w$. There was no indication that polymer degradation had begun during the follow-up period.

Histology revealed that the implants, whether drug loaded or not, were encapsulated by one or two cell layers that did not appear fibrotic in nature, as shown in FIGS. 28 and 29. The nerve fiber layer (ganglion axles) above the filament appeared intact, while the support cells immediately over the filament location are clearly absent in the PCL only implant and somewhat disrupted and thinned in the TA/PCL implanted eye. The Bruch's membrane appeared intact but there was evidence of thinning and disruption of the outer nuclear and RPE layers adjacent to the filament. Due to the lack of inflammatory response, PCL demonstrated excellent compatibility with this tissue region and the bulk of the observed cellular changes were attributed to the mechanical damage during the implantation. Other factors such as the impact of interfering with the nutritional source of these outer cellular layers may also play a role in these cellular changes.

It has been found that PCL degrades by random hydrolytic chain scission in subdermally implanted rabbits. The degradation initially manifests by a progressive reduction in molecular weight as the chain scission reactions propagate. However, it has also been shown that the physical weight of PCL does not change until the molecular weight has fallen to 5000—that is, there is no weight loss during the first phase of the degradation (Pitt CG. Poly ε caprolactone and its copolymers, In Chassin M Langer R, editors, *Biodegradable polymers as drug delivery systems*, New York: Dekker; 1990. p 71-119). Thus, phagocytosis and metabolism of small PCL fragments will not begin until the final phase of the degradation process. Further, PCL has shown excellent biocompatibility during the one-month follow up period.

The PCL/TA drug delivery system showed less disruption to the RPE layer and less tissue layer thinning in the adjacent regions of the implant than the PCL only filament, as shown in FIGS. 28 and 29. However, it is difficult to conclude whether this could be attributed to the anti-inflammatory effect of the steroid or was simply due to variability in surgical procedure and positioning. The region of retinal cell layers disruption where the implant resides extends for approximately 300 μm in width and 2000 μm in length. It has been found that the nerve fiber layer remains intact over the implant, but is disrupted at the site of the retinotomy. Thus, only a very focal region of vision loss is expected and one that is certainly less invasive than laser photocoagulation therapy.

Figure 31:
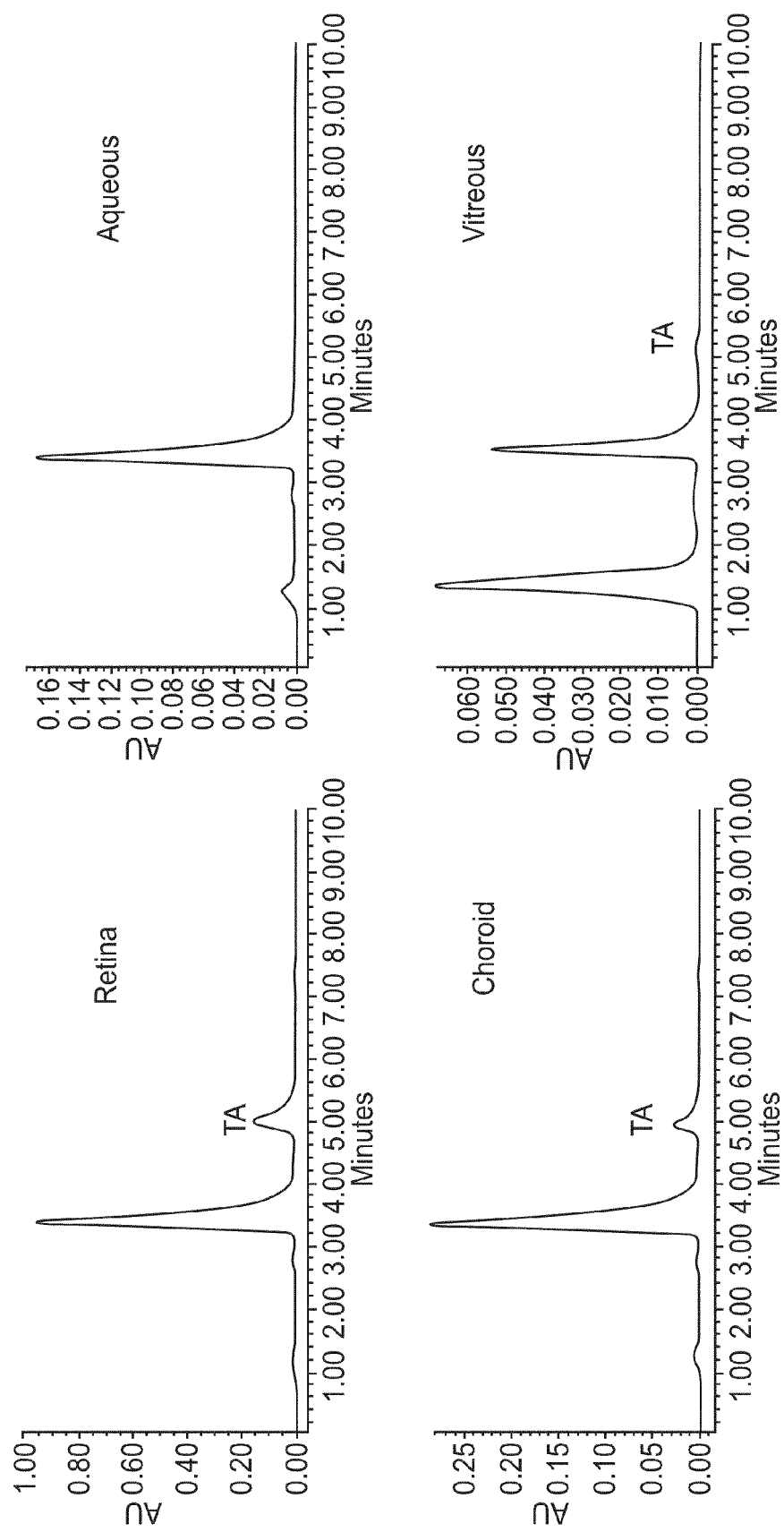
FIG. 31 shows in vivo detection of triamcinolone acetonide (TA) following a 4-week subretinal drug delivery implantation (PCL/TA 60:40) for rabbit 4.

HPLC confirmed the presence of TA four weeks after the implant in the posterior tissue samples (FIG. 31). TA was not detected in the anterior structures or the blood. HPLC peaks for TA are marked on the graphs shown in FIG. 31. The additional peaks present indicate the internal standard prednisolone.

Based upon this initial investigation, it has been demonstrated that PCL has at least a one month elution capability with TA. Drug levels in the tissue were shown to be localized to the posterior eye segment. Histology showed no indication of inflammatory response from the presence of PCL. Minor mechanical damage from the insert was observed and is believed to be the leading cause of changes in the cellular layers and structures PCL encapsulation was also evident and is expected for implanted materials.

Example 2

Materials Used and Abbreviations

Core:
NIT: 80 μm etched Nitinol wire, commercially available from Nitinol Devices and Components (Freemont Calif.).
Bioactive Agent:
RAP: Rapamycin, commercially available from LC Laboratories, Woburn Mass.
Polymers:
pEVA: polyethylene vinyl acetate copolymer (33% wt. vinyl acetate and 67% wt. polyethylene), commercially available from Aldrich Chemical Co.
pBMA: poly(n-butyl methacrylate), commercially available from Aldrich Chemical Co.
Solvent:
$CHCl_3$: chloroform solvent, commercially available from Burdick & Jackson.
Implant Preparation:
Coating Solution Preparation:

A coating solution was prepared by first adding 25.0 pails pEVA and 25.0 parts pBMA to an aliquot of $CHCl_3$ solvent. In order to dissolve the pEVA, the components were heated to 30° to 40° C. for approximately 1 hour. After the pEVA and pBMA had dissolved in the $CHCl_3$, the resulting polymer/solvent solution was allowed to cool to room temperature. Then, 50 parts of RAP was added to the polymer/solvent solution and the RAP was stirred into the polymer/solvent solution at room temperature for approximately 30 minutes to form a coating solution. The resulting coating solution was filtered using a 10 μm polypropylene filter (Gelman Sciences pall membrane Pail No. 61756). The final coating solution contained about 40 mg/ml of solids (i.e., pEVA, pBMA, and RAP).
Coating Procedure:

NIT wire was cut into lengths of approximately 1 cm each using a scissors. The wire lengths were cleaned with a wipe (Alpha Wipe from Tex Wipe) that had been dampened with isopropyl alcohol. Each wire length was then weighed to +/−0.003 μg using a microbalance (Type UMX2, from Metler-Toledo).

The coating solution was sprayed onto the NIT wire using ultrasonic coater equipment that consisted of an ultrasonic spray head (Sono-Tek, Milton, N.Y.) and syringe pump system for the coating solution. A cylindrical pin vise was used to hold the end of the NIT wire. The NIT wire was held perpendicular to the spray head at the focal point of the spray (i.e., about 2-3 mm from the spray head) and was rotated at about 200 rpm. The spray head was moved longitudinally over the NIT wire to apply the coating composition. A grid-like pattern as shown in FIGS. 11-12 was used for the coating with 0.1 mm longitudinal movements 144. The coating was dried by evaporation of the solvent at room temperature (approximately 20° C. to 22° C.) overnight. The resulting coating was about 3.0 mm in total length, comprising a center portion of about 2.0 mm in length having a uniform thickness of about 300 and two segments of about 0.5 mm in length with transitional thickness on each side of the center portion. After drying, the coated NIT wire was weighed to +/−0.003 μg using a microbalance (Type UMX2, from Metler-Toledo). The implant coating weight was calculated by subtracting the weight of the uncoated wire from the final weight of the coated wire. The total amount of RAP in each implant was calculated by multiplying the coating weight by 0.50, which represents the weight percent of RAP in the coating. The total amount of RAP in the polymer coating of the filament ranged from 26 to 89 μg (see, Table 2).

Prior to implanting in rabbits, the implants were trimmed to a length of between about 2.3 to 3.04 mm (see, Table 2).
Implantation:

Experimental protocols were approved by the Institutional Animal Care and Use Committee of the University of Southern California. Experiments were conducted in accordance with the ARVO Statement for the Use of Animals in Ophthalmic and Visual Research.

Six Dutch pigmented rabbits were given general anesthesia by an intramuscular injection of 1-1.5 mL of a 4:1 mixture of ketamine hydrochloride (100 mg/mL; Fort Dodge Labs, Fort Dodge, Iowa) and xylazine hydrochloride (100 mg/mL; Miles, Inc., Shawnee Mission, Kans.).

In all rabbits, surgery was performed on the right eye only. Pupillary dilation was achieved with topical 1% tropicamide and 2.5% phenylephrine. After limited conjunctival peritomy in the superior quadrant, stab incisions were made approximately 1 mm posterior to the limbus using a 20-gauge microvitreoretinal blade. In three rabbits (RS1, RS3 and RS4) no vitrectomy was performed. A vitreoretinal microforceps was used to grasp the end of a filament, and it was introduced into the posterior chamber through the sclerotomy. The tip of the filament was used to puncture the retina several millimeters inferior to the disc and the vascular arcades. The forceps were then used to slide the filament into the subretinal space through this retinotomy.

In three rabbits (RS3, RS5, and RS6), a vitrectomy was performed prior to filament insertion. In these eyes, one sclerotomy was created superiorly and another superonasally. An infusion cannula was inserted through the superonasal sclerotomy and sutured into place. A vitreous cutter (Bausch and Lomb Surgical, St. Louis, Mo.) was introduced through the superior sclerotomy. After completion of a core vitrectomy, the vitrector was removed from the eye. In two of the rabbits having a vitrectomy (RS5 and RS6), a 25-gauge needle was used to puncture the retina several millimeters inferior to the disc and the vascular arcades and raise a small subretinal bleb by injecting approximately 0.1 mL of balanced salt solution into the subretinal space. With the microforceps, the filament was then inserted through the retinotomy into the subretinal space in this location. In one of the rabbits (RS3) no subretinal bleb was raised; rather, the filament was inserted directly beneath the retina after vitrectomy in the manner described above.

In all rabbits, after the filament had been inserted, the instruments were removed from the eye, and the sclerotomies were closed with 7-0 Vicryl sutures (Johnson and Johnson, Piscataway, N.J.). The conjunctiva was left to close by secondary intention. Subconjunctival injection of gentamicin (0.2 mL of 40 mg/mL solution, American Pharmaceutical Partners, Schaumberg, Ill.) was performed.

Monitoring and Evaluation:

Indirect ophthalmoscopic examination, fundus photography, fluorescein angiography, and optical coherence tomography were performed on the right eye of each rabbit at 1, 2, and 4 weeks post-operatively. After the week 4 studies were completed, the rabbits were euthanized with an intracardiac injection of sodium pentobarbital (Anpro Pharmaceuticals, Arcadia, Calif.). The right eye of each rabbit was enucleated and placed in 4% paraformaldehyde for 24 hours. The eyes were then transferred to Dulbecco's phosphate buffered saline for storage at 4° C. until further dissection, at which time they were sectioned down to a 2 cm×2 cm block of the retina-choroid-sclera complex at the posterior pole. This was embedded in paraffin, sectioned, and stained with hematoxylin and eosin using standard techniques.

Implantation Results:

Filaments were implanted into the subretinal space in three rabbits and into the sub-RPE space in one rabbit. (see, Table 2) In four eyes (RS1-RS4), no bleb of subretinal fluid was raised prior to implantation of the filament. In these cases, there was one subretinal implantation (RS1), one sub-RPE implantation (RS3), and two unsuccessful attempts at implantation. In two cases (RS5 and RS6), a bleb of subretinal fluid was raised before filament placement. In both of these instances, the filament was inserted into the subretinal space without difficulty.

The presence or absence of the vitreous body over the area of implantation was found to be a factor determining the ease of the procedure. In one of the cases in which no vitrectomy was performed (RS1), the surgeon was able to insert the filament into the subretinal space, and the filament remained in place upon removal of the forceps. However, two rabbits (RS2 and RS4), both of which did not undergo vitrectomy prior to filament implantation, were sacrificed at the time of surgery because of the creation of multiple retinotomies during attempted implantation. In these two cases, the vitreous body prevented successful implantation by adhering to the filament and causing it to egress from the subretinal space when the implantation forceps were withdrawn. By contrast, when a vitrectomy had been performed prior to implantation (RS3, RS5, and RS6), it was possible to release the filament and withdraw the forceps without disturbing the position of the device.

Tolerance of Filament Implants in the Rabbit Eye:

All scheduled follow-up exams were completed over a one-month time period for three of the four rabbits that received implants (RS1, RS3, and RS5). In one rabbit (RS6), posterior synechiae developed between weeks 1 and 2, so adequate pupillary dilation could not be achieved on the follow-up exams at weeks 2 and 4. Consequently, fluorescein angiography (FA) and optical coherence tomography (OCT) studies could not be performed at these visits. No retinal detachment occurred in any of the four eyes that received implants.

Figure 32:
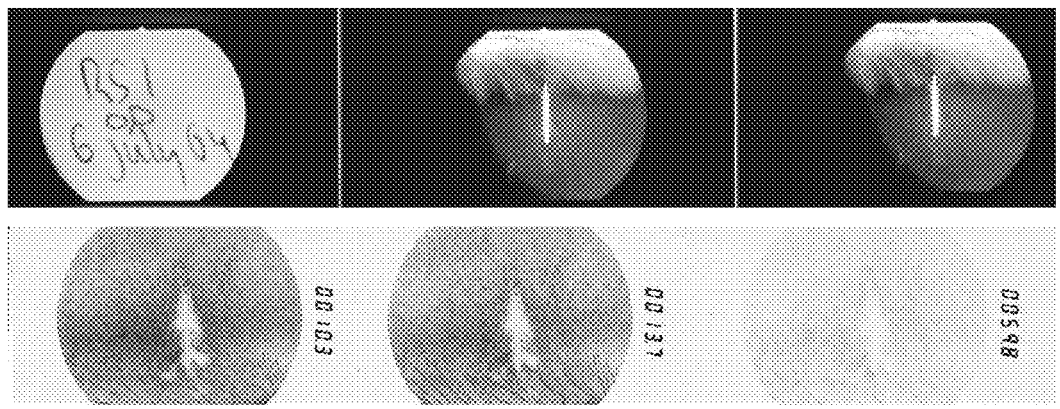
FIG. 32 shows a photo of RS1, one (1) week post surgery, photo and fluorescein angiography.
Figure 33:
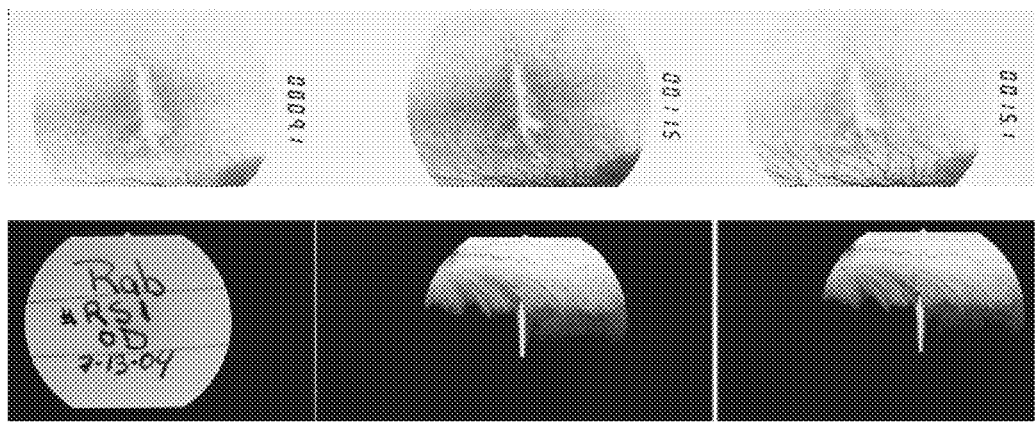
FIG. 33 shows a photo of RS1, two (2) weeks post surgery, photo and fluorescein angiography.
Figure 34:
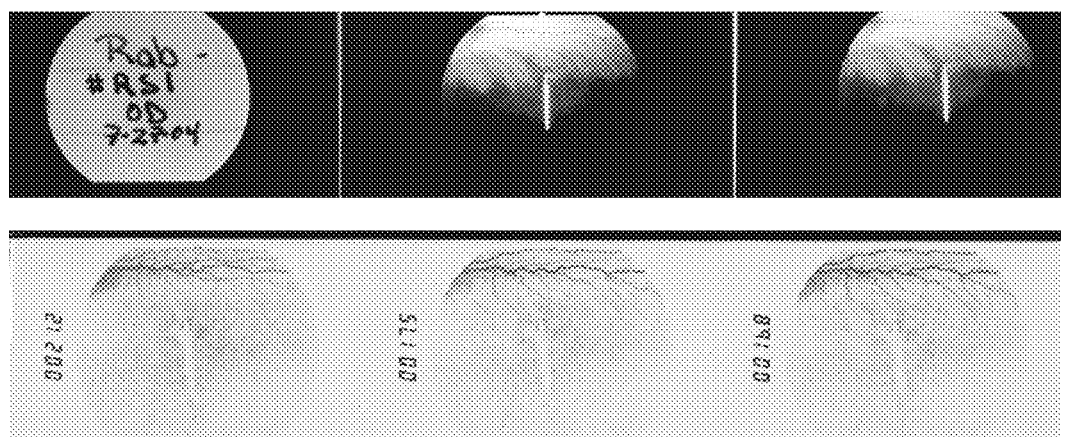
FIG. 34 shows a photo of RS1, four (4) weeks post surgery, photo and fluorescein angiography.
Figure 35:
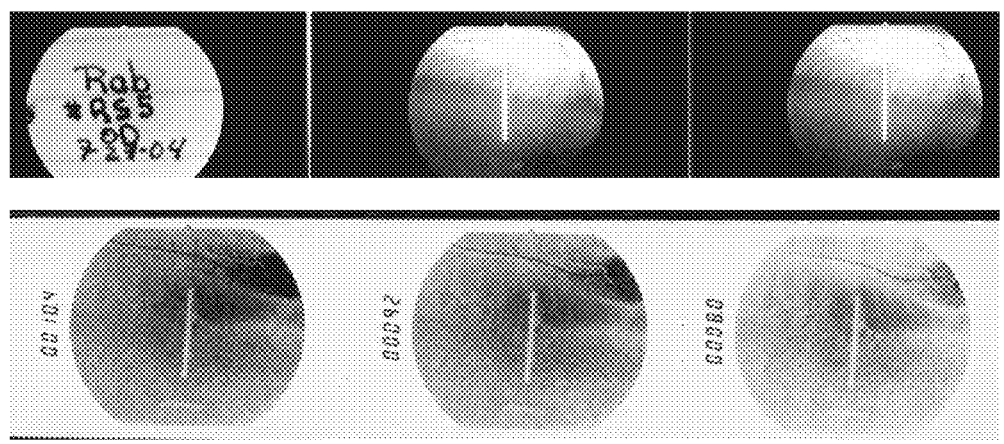
FIG. 35 shows a photo of RS5, four (4) weeks post surgery, photo and fluorescein angiography.

In three rabbits (RS1, RS3, and RS5), no signs of inflammation or toxicity were detected on follow-up examination. In addition, the filaments did not migrate from their initial implantation sites. In RS1, in which no bleb of subretinal fluid was raised prior to device insertion, at week 1 small amounts of residual subretinal hemorrhage from the procedure were still present adjacent to the filament, causing blockage on fluorescein angiography (FIG. 32). This resolved with time, so that less blockage from subretinal hemorrhage was noted at week 2 (FIG. 33) and none by week 4 (FIG. 34). The angiogram otherwise showed only blockage by the device. OCT also confirmed the subretinal location of the device (FIG. 34). There was no evidence of atrophy or damage to adjacent retina or RPE. In RS5, in which a bleb of subretinal fluid was raised to assist with correct subretinal device placement, there was no subretinal hemorrhage noted at any time point. Fluorescein angiography showed a linear hypofluorescent spot inferior to the device that was the site of instrument touch during surgery. In addition, mild hypopigmentation could be seen around the device, corresponding to the area in which the subretinal bleb had been raised. This circular area appeared mildly hyperfluorescent on angiography (FIG. 35). There was no indication of other damage to adjacent tissue by the implant.

In RS6, exams at weeks 1 and 2 showed that the filament remained stable at the site of implantation, and the adjacent tissue appeared normal. Mild anterior chamber inflammation and posterior synechiae developed by week 2, so pupillary dilation was impaired, making photography difficult. Indirect ophthalmoscopy showed no evidence of posterior chamber inflammation.

Figure 36:
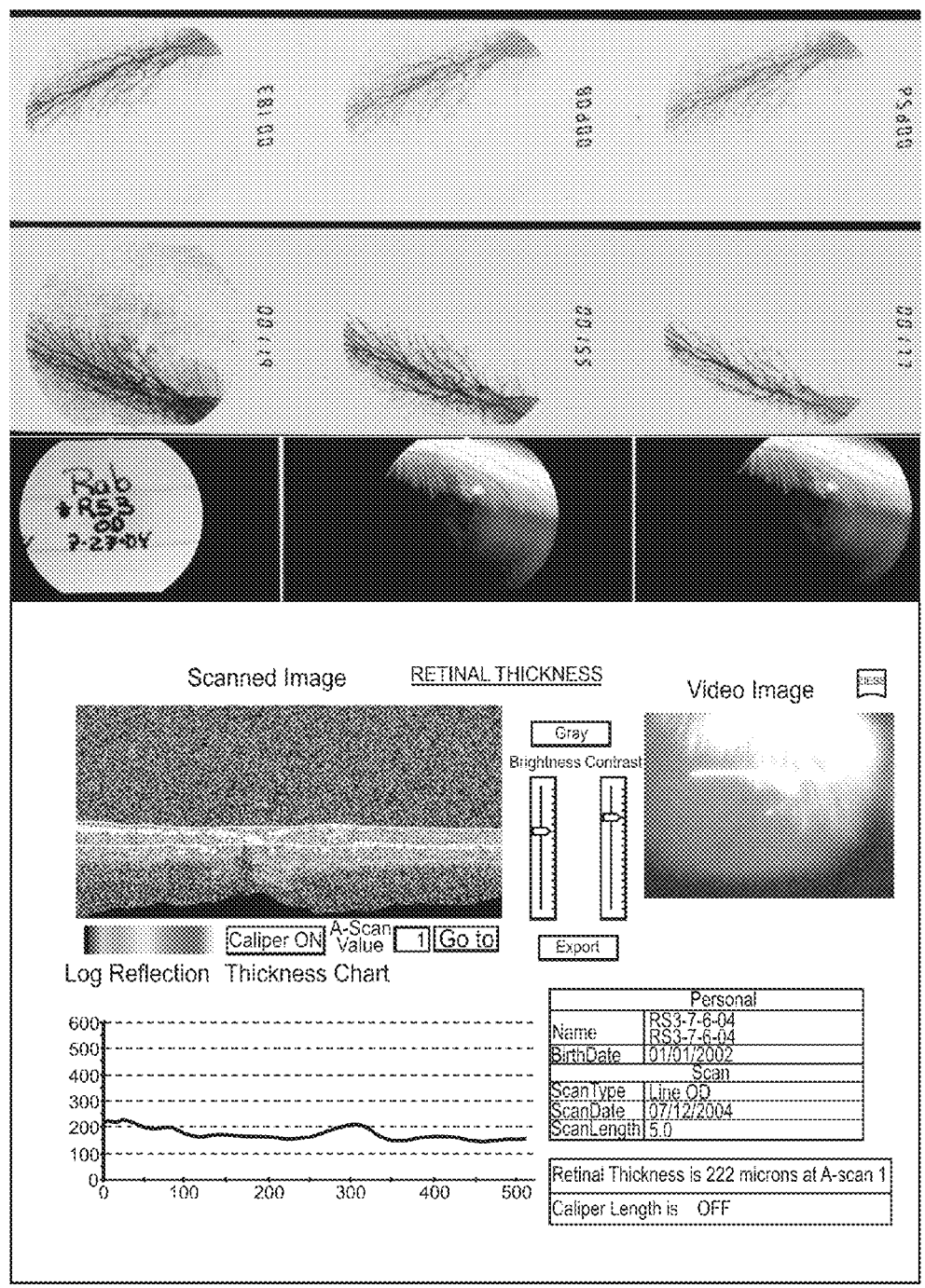
FIG. 36 shows a photo of RS3, 4 weeks post surgery, photo, fluorescein angiography and optical coherence tomography.

In RS3, in which the device was implanted beneath the RPE, the filament also remained in a stable position and did not cause any visible abnormalities of adjacent areas. The implant could not be directly visualized on examination, but angiography showed blockage by it, and OCT appeared to corroborate its location (FIG. 36).

Figure 37:
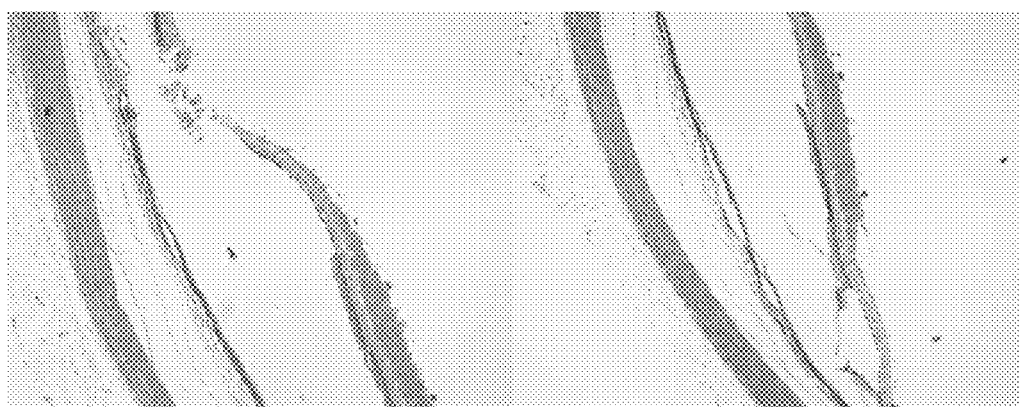
FIG. 37 shows a histology photo of RS1.

Histology Results:

In eyes in which the filament was implanted subretinally, sections of the posterior pole at the implantation site showed loss of photoreceptors overlying the device. Adjacent structures appeared normal. A histology photo of RS1 is shown in FIG. 37.

TABLE 2

Filament Characteristics and Implantation Results

| Rabbit No. | Vitrectomy | Bleb | Filament Length (mm) | Total RAP Content (ug) | Outcome |
|---|---|---|---|---|---|
| RS1 | No | No | 2.3 | 28 | Subretinal Implantation |
| RS2 | No | No | 3.04 | 61.5 | Sacrificed |
| RS3 | Yes | No | 2.54 | 88.5 | Sub-RPE Implantation |
| RS4 | No | No | 2.88 | 28 | Sacrificed |
| RS5 | Yes | Yes | 2.7 | 26 | Subretinal Implantation |
| RS6 | Yes | Yes | 2.46 | 89 | Subretinal Implantation |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A method for instilling one or more bioactive agents into ocular tissue within an eye of a patient for the treatment of an ocular condition, the method comprising concurrently using at least two of the bioactive agent delivery methods (A)-(C):
   (A) implanting a sustained release delivery device comprising one or more bioactive agents in a posterior region of the eye so that it delivers the one or more bioactive agents into a vitreous humor;
   (B) instilling one or more bioactive agents subretinally by direct injection or by implantation of a delivery device comprising one or more bioactive agents; and
   (C) instilling one or more bioactive agents into the vitreous humor by direct injection or by iontophoresis.

2. The method of claim 1, wherein method (A) is used concurrently with method (B).

3. The method of claim 1, wherein method (A) is used concurrently with method (C).

4. The method of claim 1, wherein method (B) is used concurrently with method (C).

5. The method of claim 1, wherein method (A) is used concurrently with method (B) and with method (C).

6. The method of claim 1, wherein method (B) comprises: (a) forming a localized retinal detachment to define a subretinal space; and (b) instilling one or more bioactive agents in the subretinal space formed by localized retinal detachment.

7. The method of claim 1 wherein the one or more bioactive agents are provided in a sustained release delivery device that is configured for implantation in the subretinal space.

8. The method of claim 7, wherein the sustained release delivery device of (B) is tapered at a proximal end, a distal end, or both the proximal and distal ends.

9. The method of claim 7, wherein the sustained release delivery device of (B) is a solid in the form of a capsule, pellet, rod, sheet, or film.

10. The method of claim 7, wherein the sustained release delivery device of (B) comprises a core having an outer surface; and a coating layer of a polymer matrix and at least one bioactive agent applied over at least a portion of the outer surface of the core.

11. The method of claim 10, wherein the coating layer is provided on a portion of the outer surface of the core.

12. The method of claim 10, wherein the coating layer is provided on an intermediate portion of the core.

13. The method of claim 10, wherein the core is selected from titanium alloys, nickel-cobalt base alloys, stainless steel, cobalt-chromium alloys, and biodegradable magnesium alloys.

14. The method of claim 10, wherein the polymer matrix comprises a first polymer and a second polymer wherein the first polymer is a poly(alkyl(meth)acrylate) or a poly(aromatic(meth)acrylate) and wherein the second polymer is poly(ethylene-co-vinyl acetate).

15. The method of claim 1, wherein the sustained release delivery device of (A) comprises:
   a nonlinear body member having a direction of extension, a longitudinal axis along the direction of extension, and a proximal end and a distal end,
   wherein at least a portion of the body member deviates from the direction of extension,
   and wherein the body member includes the one or more bioactive agents, and a polymer matrix.

16. The method of claim 15, wherein the body member is coil-shaped.

17. The method of claim 15, wherein the body member includes a lumen.

18. The method of claim 15, wherein the polymer matrix comprises a first polymer and a second polymer, wherein the first polymer is a poly(alkyl(meth)acrylate) or a poly(aromatic(meth)acrylate), and wherein the second polymer is poly(ethylene-co-vinyl acetate).

19. The method of claim 1, wherein method (C) comprises injecting one or more bioactive agents into the vitreous humor or comprises delivering one or more bioactive agents into the vitreous humor using iontophoresis.

20. The method of claim 1, wherein the one or more bioactive agents are selected from antiproliferative agents, anti-inflammatory agents, inhibitors of angiogenesis, antibiotics, hormonal agents, neurotropic factors, or combinations thereof.

* * * * *